(12) United States Patent
Nicotera et al.

(10) Patent No.: US 7,427,608 B2
(45) Date of Patent: Sep. 23, 2008

(54) PROTECTION AGAINST AND TREATMENT OF HEARING LOSS

(75) Inventors: Thomas Nicotera, Buffalo, NY (US); Donald Henderson, Williamsville, NY (US); David G. Hangauer, Jr., Amherst, NY (US)

(73) Assignees: The Research Foundation of State University of New York, Amherst, NY (US); Health Research, Inc., Buffalo, NY (US)

( * ) Notice: Subject to any disclaimer, the term of this patent is extended or adjusted under 35 U.S.C. 154(b) by 174 days.

(21) Appl. No.: 11/395,937

(22) Filed: Mar. 31, 2006

(65) Prior Publication Data

US 2006/0172971 A1 Aug. 3, 2006

Related U.S. Application Data

(62) Division of application No. 10/277,220, filed on Oct. 19, 2002, now Pat. No. 7,129,225.

(60) Provisional application No. 60/336,191, filed on Oct. 22, 2001, provisional application No. 60/410,726, filed on Sep. 13, 2002.

(51) Int. Cl.
  *A61K 31/69* (2006.01)
  *A61K 31/165* (2006.01)
(52) U.S. Cl. .................. 514/64; 514/114; 514/622
(58) Field of Classification Search .................. None
  See application file for complete search history.

(56) References Cited

U.S. PATENT DOCUMENTS

| | | | |
|---|---|---|---|
| 5,464,861 A | 11/1995 | Dobrusin et al. | |
| 5,532,167 A | 7/1996 | Cantley et al. | |
| 5,552,534 A | 9/1996 | Hirschmann et al. | |
| 5,648,378 A | 7/1997 | Huang | |
| 5,705,585 A | 1/1998 | Hogan, Jr. | |
| 5,736,412 A | 4/1998 | Zambias et al. | |
| 6,011,175 A | 1/2000 | Sebti et al. | |
| 6,420,338 B1 | 7/2002 | Schneider et al. | 514/12 |
| 6,552,066 B1 | 4/2003 | Sharpe et al. | 514/419 |
| 7,005,445 B2 * | 2/2006 | Hangauer et al. | 514/419 |
| 7,070,936 B1 | 7/2006 | Hangauer, Jr. et al. | 435/7.1 |
| 7,129,225 B2 | 10/2006 | Nicotera et al. | 514/64 |
| 2003/0016615 A1 | 1/2003 | Lee et al. | 369/112.24 |
| 2004/0019015 A1 | 1/2004 | Nicotera et al. | 514/64 |
| 2006/0030544 A1 | 2/2006 | Hangauer, Jr. et al. | 514/80 |
| 2006/0089401 A1 | 4/2006 | Hangauer, Jr. et al. | 514/419 |
| 2006/0172971 A1 | 8/2006 | Nicotera et al. | 514/64 |
| 2008/0004241 A1 | 1/2008 | Hangauer | 514/80 |

FOREIGN PATENT DOCUMENTS

| | | |
|---|---|---|
| DE | 43 07 883 A1 | 9/1993 |
| EP | 0 846 464 A2 | 6/1998 |
| WO | 0 370 381 A2 | 5/1990 |
| WO | WO 91/09849 | 7/1991 |
| WO | WO 96/35805 | 11/1996 |
| WO | WO 96/39384 | 12/1996 |
| WO | WO 96/39385 | 12/1996 |
| WO | WO 98/27108 | 6/1998 |
| WO | WO 00/42213 | 7/2000 |
| WO | WO 01/85726 A1 | 11/2001 |
| WO | WO 02/072548 A2 | 9/2002 |
| WO | WO 03/093297 A2 | 11/2003 |

OTHER PUBLICATIONS

Huang et al., "Polyhydroxylated 3-(N-Phenyl) Carbamoyl-2-Iminochromene Derivatives as Potent Inhibitors of Tyrosine Kinase $p60^{c-src}$," *Bioorganic & Medicinal Chemistry Letters*, 5(20):2423-2428 (1995).

Levitzki et al., "Tyrosine Kinase Inhibition: An Approach to Drug Development," *Science*, 267:1782-1788 (1995).

Lawrence et al., "Protein Kinase Inhibitors: The Tyrosine-Specific Protein Kinases," *Pharmacol. Ther.*, 77(2):81-114 (1998).

Lai, et al., "The Design, Synthesis and Activity of Pentapeptide $pp60^{c-src}$ Inhibitors Containing L-phosphotyrosine Mimics," *J. Peptide Res.*, 51:271-281 (1998).

Kennedy, "Role of Protein Tyrosine Phosphatase-1B in Diabetics and Obesity," *Biomedicine & Pharmacotherapy*, 53(10):466-470 (1999) (Abstract).

Biscardi, et al., "c-Src, Receptor Tyrosine Kinases and Human Cancer," *Advances in Cancer Research*, 61-119 (1999).

"Amersham Pharmacia Biotech to Market and Distribute BioFocus' SoftFocus(TM) Kinase Libraries in North America," News release: Nov. 23, 1999.

Ripka, "Chapter 21. Protein Tyrosine Phosphatase Inhibition," *Annual Reports in Medicinal Chemistry*, 35:231-250 (2000) (Abstract).

Pestell, et al., "Small Molecule Inhibitors of Dual Specificity Protein Phosphatases," *Oncogene*, 19(56):6607-6612 (2000) (Abstract).

Moller, et al, "Protein Tyrosine Phosphatases (PTPs) as Drug Targets: Inhibitors of PTP-1B for the Treatment of Diabetes," *Current Opinion in Drug Discovery & Development*, 3(5):527-540 (2000) (Abstract).

Irby et al., "Role of Src Expression and Activation in Human Cancer," *Oncogene*, 19:5636-5642 (2000).

(Continued)

*Primary Examiner*—Kamal A Saeed
(74) *Attorney, Agent, or Firm*—Ivor R. Elrifi; Heidi A. Erlacher; Mintz, Levin, Cohn, Ferris, Glovsky & Popeo, P.C.

(57) ABSTRACT

The present invention provides a method for protecting against or treating hearing loss in a subject. This method involves administering an effective amount of a protein tyrosine kinase inhibitor to the subject to protect against or to treat hearing loss.

25 Claims, 22 Drawing Sheets

OTHER PUBLICATIONS

Garcia-Echeverria, et al., "ATP Site-Directed Competitive and Irreversible Inhibitors of Protein Kinases," *Med. Res. Rev.*, 20(1):28-57 (2000).

Abram, et al., "Src Family Tyrosine Kinases and Growth Factor Signaling," *Experimental Cell Research*, 254:1-13 (2000).

Marsilje, et al., "The Design, Synthesis and Activity of Non-ATP Competitive Inhibitors of pp60$^{c-src}$ Tyrosine Kinase. Part 1: Hydroxynaphthalene Derivatives," *Bioorg. Med. Chem. Lett.*, 10:477-481 (2000).

Milkiewicz et al., "The Design, Synthesis and Activity of Non-ATP Competitive Inhibitors of pp60$^{c-src}$ Tyrosine Kinase. Part 2: Hydroxyindole Derivatives," *Bioorg. Med. Chem. Lett.*, 10:483-486 (2000).

Schelssinger, "New Roles for Src Kinases in Control of Cell Survival and Angiogenesis," *Cell*, 100:293-296 (2000).

Sedlacek, "Kinase Inhibitors in Cancer Therapy," *Drugs*, 59(3):435-476 (2000).

Susa et al., "Tyrosine Kinase Src Inhibitors: Potential Therapeutic Applications," *Drug News Perspect.*, 13(3):169-175 (2000).

Sridhar et al., "Protein Kinases as Therapeutic Targets," *Pharmaceutical Research*, 17(11):1345-1353 (2000).

Biscardi, et al., "Tyrosine Kinase Signaling in Breast Cancer: Epiderman Growth Factor Receptor and c-Src Interactions in Breast Cancer," *Breast Cancer Res.*, 2:203-210 (2000).

Súsa et al., "Src Inhibitors: Drugs for the Treatment of Osteoporosis, Cancer or Both?," *TiPS*, 21:489-495 (2000).

Hubbard et al., "Protein Tyrosine Kinase Structure and Function," *Annu. Rev. Biochem.*, 69:373-398 (2000).

Fretz et al., "Structure-based Design of Compounds Inhibiting Grb2-SH2 Mediated Protein-Protein Interactions in Signal Transduction Pathways," *Current Pharmaceutical Design*, 6(18):1777-1796 (2000) (Abstract).

Vu, "Recent Advances in the Design and Synthesis of SH2 Inhibitors of Src, Grb2 and ZAP-70," *Current Medicinal Chemistry*, 7(10):1081-1100 (2000) (Abstract).

Haskell, et al., "c-Src Tyrosine Phosphorylation of Epidermal Growth Factor Receptor, P190 RhoGAP, and Focal Adhesion Kinase Regulates Diverse Cellular Processes," *Chemical Reviews*, 101(8):2425-2440 (2001).

McCluskey et al., "Small Molecule Inhibitors of Serine/Threonine Protein Phosphatases," *Mini-Reviews in Medicinal Chemistry*, 1(1):43-55 (2001) (Abstract).

Zhang, "Protein Tyrosine Phosphatases: Prospects for Therapeutics," *Current Opinion in Chemical Biology* 5(4):416-423 (2001) (Abstract).

Bridges, "Chemical Inhibitors of Protein Kinases," *Chemical Reviews*, 101(8):2541-2571 (2001).

Park et al., "Metabolism of Fluorine-Containing Drugs," *Annu. Rev. Pharmacol, Toxicol.*, 41:443-470 (2001).

Sawyer et al., "Src Inhibitors: Genomics to Therapeutics," *Expert Opin. Investg. Drugs*, 10(7):1327-1344 (2001).

Blume-Jensen et al., "Oncogenic Kinase Signaling," *Nature*, 411:355-365 (2001).

Martin, "Timeline: The Hunting of the Src," *Nat. Rev. Mol. Cell Biol.*, 2:467-475 (2001).

Garcia-Echeverria, "Antagonists of the Src Homology 2 (SH2) Domains of Grb2, Src, Lck and ZAP-70," *Current Medicinal Research*, 8(13):1589-1604 (2001) (Abstract).

Muller, "Peptidomimetic SH2 Domain Antagonists for Targeting Signal Transduction," *Topics in Current Chemistry*, 211:17-59 (2001) (Abstract).

Zhang, "Protein Tyrosine Phosphatases: Structure and Function, Substrate Specificity, and Inhibitor Development," *Annual Review of Pharmacology and Toxicology*, 42:209-234 (2002) (Abstract).

McCluskey et al., "Serine-Threonine Protein Phosphatase Inhibitors: Development of Potential Therapeutic Strategies," *Journal of Medicinal Chemistry*, 45(6):1151-1175 (2002) (Abstract).

Johnson et al., "Protein Tyrosine Phosphatase 1B Inhibitors for Diabetes," *Nat. Rev. Drg Discov.*, 1(9):696-709 (2002) (Abstract).

Frame, "Src in Cancer: Deregulation and Consequences for Cell Behavior," *Biochemica et Biophysica Acta*, 1602:114-130 (2002).

Druker, "STI571 (Gleevec) as a Paradigm for Cancer Therapy," *Trends in Molecular Medicine*, 8(4 Suppl):S14-18 (2002) (Abstract).

Bakhtiar et al., "Quantification of the Anti-Leukemia Drug STI1571 (Gleevec) and its Metabolite (CGP 74588) in Monkey Plasma Using a Semi-Automated Solid Phase Extraction Procedure and Liquid Chromatography-Tandem Mass Spectrometry," *Journal of Pharmaceutical & Biomedical Analysis*, 28(6):1183-1194 (2002) (Abstract).

Burke et al., "Phosphotyrosyl Mimetics in the Development of Signal Transduction Inhibitors," *Acc. Chem. Res.*, 36:426-433 (2003).

Levitzki, "Protein Kinase Inhibitors as a Therapeutic Modality," *Acc. Chem. Res.*, 36(6):462-469 (2003).

Stein, "SH2 and SH3 Domains. Unraveling Signaling Networks with Peptide Antagonists," *Methods in Molecular Biology*, 88:187-195 (1998) (Abstract).

Sparks et al., "Identification and Characterization of Src SH3 Ligands from Phage-Displayed Random Peptide," *Journal of Biological Chemistry*, 269(39):23853-23856 (1994) (Abstract).

Milkiewicz, "Design, Synthesis and Biological Testing of Non-ATP Competitive Inhibitors of the pp60$^{c-src}$ Protein Tyrosine Kinase," A dissertation submitted to the Faculty of the Graduate School of State University of New York at Buffalo in Partial Fulfillment of the Requirements for the Degree of Doctor of Philosophy, Department of Medicinal Chemistry (Sep. 5, 2001).

Nicotera et al., "Novel Inhibition of Noise-Induced Apoptosis in Cochlear Hair Cell Using Inhibitors of pp60$^{c-src}$ Protein Tyrosine Kinase," Twenty-Sixth Annual Midwinter Research Meeting of the Association for Research in Otolaryngology, Daytona Beach, Florida (Feb. 22-27, 2003).

Alfaro-Lopez et al. *J. Med. Chem.*, 41:2252-2260 (1998).

Burke et al. *J. Med. Chem.*, 36(4):425-432 (1993).

Casnellie et al., *Adv. Enzyme Regul.*, 22:501-515 (1984).

Choi "Development of a Cellular Mimetic Protein Kinase Assay and a Novel Methodology for Determining the Mode of Inhibition for Multisubstrate" thesis, Bell & Howell Co., (1999).

Engström et al. *Meth. Enzymol.*, 107:130-154 (1984).

Faltynek et al. *Biochem.*, 34:12404-12410 (1995).

Fry et al. *Science*, 265:1093-1095 (1994).

Fukunaga et al. *Protein Phosphorylation*, Second Edition, Chapter 13, pp. 291-313 (1999).

Hanke et al. *J. Biol. Chem.*, 271(2):695-701 (1996).

Harris et al. *Hearing Res.*, 208:14-25 (2005).

Hsiao et al. *Synthesis*, pp. 1043-1046 (1998).

Hubbard *EMBO J.*, 16(18):5572-5581 (1997).

Kemp et al. *Meth. Enzymol.* 200:121-134 (1991).

Kemp et al. *TIBS*, 15:342-346 (1990).

Kim et al. *Int. J. Peptide Protein Res.*, 44:457-465 (1994).

Lai et al. *J. Org. Chem.* 61:1872-1874 (1996).

Lawrence et al. *Pharmacol. Ther.*, 77(2)81-114 (1998).

Lou et al. *Bioorg. Med. Chem.*, 4(5):677-682 (1996).

Metfalf III et al. *Curr. Pharm. Design*, 8:2049-2075 (2002).

Mohammadi et al. *cience*, 276:955-960 (1997).

Nair et al. *J. Med. Chem.*, 38:4276-4283 (1995).

Nair et al. *Synthesis*, pp. 810-814 (1995).

Patrick et al. *DDT*, 1(8):325-330 (1996).

Pearson et al. *Meth. Enzymol.*, 200:62-81 (1991).

Ramdas et al. *Arch. Biochem. Biophys.*, 323(2):237-242 (1995).

Rewcastle et al. *J. Med. Chem.*, 39:1823-1835 (1996).

Ruzzene et al. *Protein Phosphorylation*, Second Edition, Chapter 10, pp. 221-252 (1999).

Saperstein et al. *Biochem.*, 28:5694-5701 (1989).

Sawutz et al. *Biochem. Pharmacol.*, 51:1631-1638 (1996).

Sawyer *Expert Opin. Investig. Drugs*, 13(1):1-19 (2004).

Shoichet *Nature*, 432:862-765 (2004).

Showalter et al. *Pharmacol. Ther.*, 76(1-3):55-71 (1997).

Songyang et al. *Meth. Mol. Biol.*, 87:87-98 (1998).

Sparks et al. *Int. J. Biochem.*, 18(6):497-504 (1986).

Tegge et al. *Meth. Mol. Chem.*, 87:99-106.

Thakkar et al. *J. Med. Chem.*, 36:2950-2955 (1993).

Xu et al. *Nature*, 385:595-602 (1997).

Zheng et al. *Biochem.*, 32:2154-2161 (1993).

Chemical Abstracts vol. 67, No. 1 (1967) abstract No. 1850x (Chi-Ting Chou) p. 166 & Yao Hsueh Ao, vol. 13, No. 6 (1966).

Hoover et al. *J. Med. Chem.*, 41(16):2934-2938 (1998).

Patent Abstracts of Japan vol. 13, No. 384 (1989) & JP 01 132579 A (SS Pharmaceut. Co. Ltd.) abstract only (1989).
Poulain et al. *J. Med. Chem.*, 44(21):3378-3390 (2001).
Romero et al. *J. Med. Chem.*, 37(7):999-1014 (1994).

Supplementary Partial European Search Report for EP 02 77 3833, mailed Sep. 29, 2005.

* cited by examiner

Figure 2
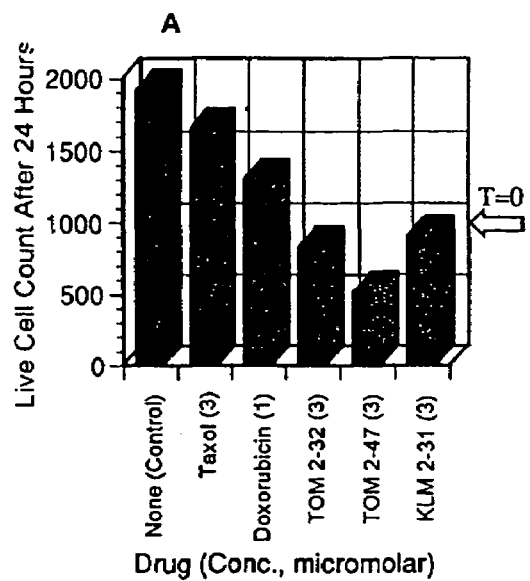
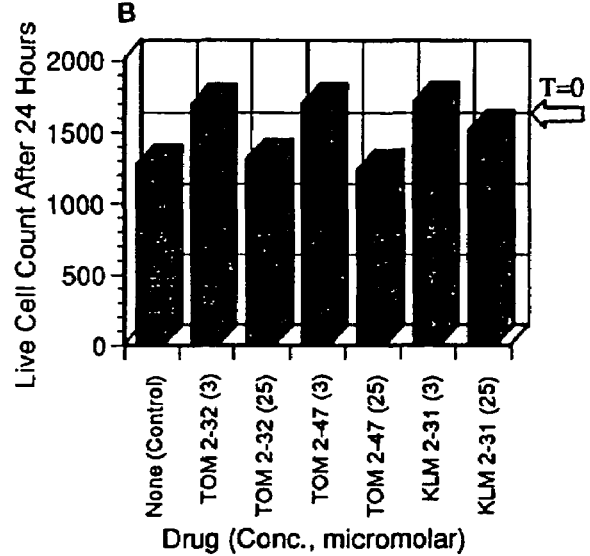
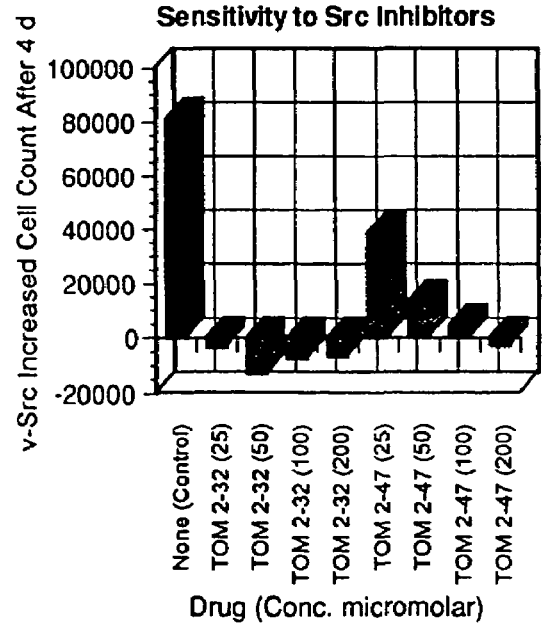
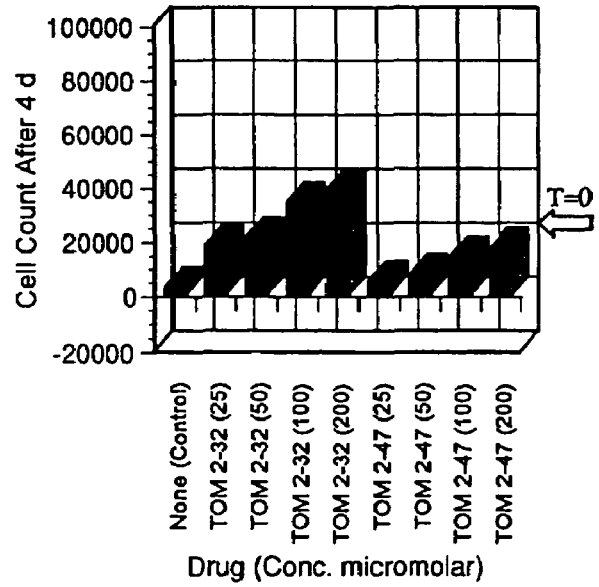

TOM 2-32   TOM 2-47   KLM 2-31

Figure 3
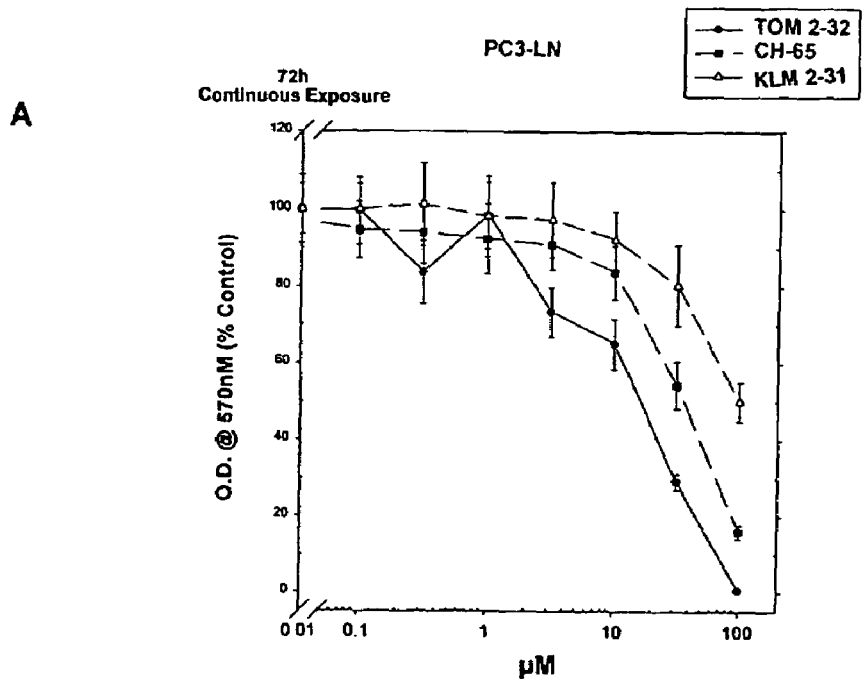
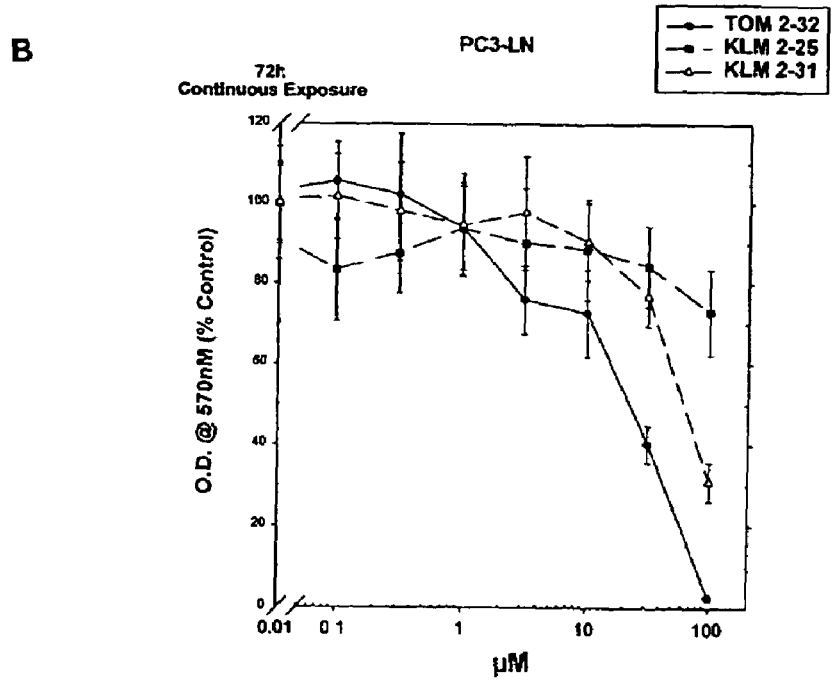

Figure 19
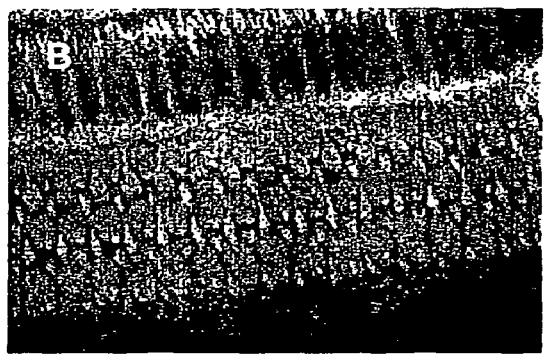
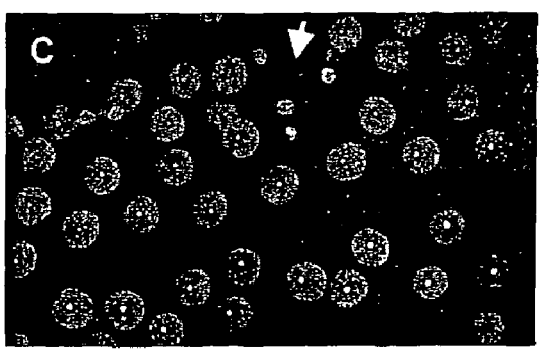
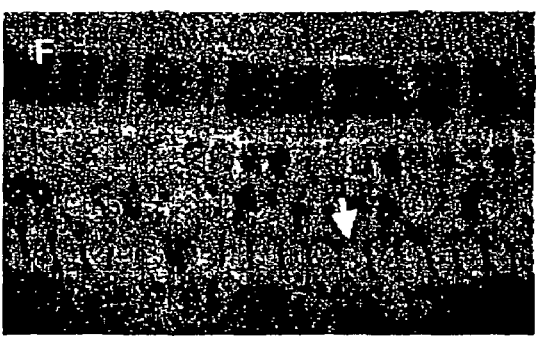

PROTECTION AGAINST AND TREATMENT OF HEARING LOSS

RELATED APPLICATIONS

This application is a Divisional of U.S. Non-provisional application Ser. No. 10/277,220 filed on Oct. 19, 2002, now U.S. Pat. No. 7,129,225, which claims the benefits to U.S. Provisional Application No. 60/336,191 filed Oct. 22, 2001 and U.S. Provisional Application No. 60/410,726, filed Sep. 13, 2002, which are hereby incorporated by reference in their entirety.

The subject matter of this application was made with support from NIH/NIDCD (Grant No(s). PO1-DC03600, 1R21DC04984-01). The U.S. Government may have certain rights in this invention.

BACKGROUND OF THE INVENTION

The effects of high level noise and ototoxic drugs, such as cisplatin or the class of aminoglycosides, share several common features in the inner ear. First, the noise and/or drugs alter the free radical/antioxidant levels in the cochlea (inner ear). The increase in free radicals has been shown to be a causative factor in the apoptotic death of the sensory cells.

This cell death can be prevented or limited by augmenting the inner ear's antioxidant response to stress. However, when the ear is being stressed by cisplatin, systemic administration of antioxidants can interfere with the therapeutic processes of the drug. Moreover, high concentration levels of antioxidants are required to achieve therapeutic benefits. The present invention provides a novel approach for protecting against or treating hearing loss.

SUMMARY OF THE INVENTION

The present invention relates to a method for protecting against or treating hearing loss in a subject. This method involves administering an effective amount of a protein tyrosine kinase inhibitor to the subject to protect against or to treat hearing loss.

In accordance with the method of the present invention, a low concentration of protein tyrosine kinase inhibitor can be administered to the subject to achieve the desired effect. In addition, the protein tyrosine kinase inhibitors disclosed herein exhibit low toxicity and, therefore, are suitable for treatment of hearing loss. Further, the protein tyrosine kinase inhibitors can be administered an amount effective to protect against or treat hearing loss, as well as to treat other disorders responsive to protein kinase inhibitors, such as cancer, psoriasis, artherosclerosis, or immune system activity. In particular, the protein tyrosine kinase inhibitors may provide a synergistic effect with certain cancer drugs. For example, promising inhibitors can be screened in primary human tumor tissue assays, particularly to look for synergy with other known anti-cancer drugs. In addition, the protein kinase inhibitors may reduce toxicity of certain cancer drugs (e.g., platinum-based drugs which are toxic to the cochlea and kidney), thereby allowing increased dosage.

BRIEF DESCRIPTION OF THE DRAWINGS

FIG. 2A shows a comparison of taxol and doxorubicin (they were more effective than etoposide and cisplatin in this tumor cell culture) with three Src inhibitors (see FIG. 2E) utilizing ovarian tumor cells from tumor N015. FIG. 2B shows the results from tests of the Src inhibitors for inhibition of normal human fibroblast cell growth. No inhibition of normal cell growth (both subconfluent and confluent; some enhanced growth was observed instead) was found, indicating that these inhibitors are not toxic to normal cells even at a 10-fold higher concentration. FIG. 2C shows the results from tests of two of the Src inhibitors for inhibition of ts v-Src stimulated LA25 cell growth. FIG. 2D shows the results from tests of two of the Src inhibitors for inhibition of normal rat kidney cell growth.

FIGS. 3A-B are graphs showing in vitro cytotoxicity of malignant prostate PC-3-LN cells with a range of each of four Src protein tyrosine kinase inhibitors and one inactive control (KLM 2-25).

FIGS. 19A-F are SEM images of chinchilla cochleas. FIG. 19A shows a split (marked by S) of the reticular lamina after exposure to an impulse noise. FIG. 19B shows focal adhesion kinase (FAK) staining in a cochlea exposed to an octave band noise centered at 4 kHz (OBN) at 105 dB (SPL). FIG. 19C shows a small lesion with a few apoptotic nuclei (marked with arrow) from a cochlea exposed to an OBN at 110 dB. FIG. 19D shows FAK staining for the lesion shown in FIG. 19C. FIG. 19E shows a confocal scanning level a few microns lower than in FIG. 19D, demonstrating that the lesion extends well below the cuticular plate and into the cell body (marked with arrow). FIG. 19F shows FAK staining in a cochlea exposed to impulse noise at 155 dB (SPL). In this figure, many outer hair cells have lost their cuticular plate integrity. The remaining outer hair cells show strong FAK fluorescence in the cuticular plates.

In FIG. 20A, the chinchilla cochlea was pre-treated with CH-65. In FIG. 20B, the chinchilla cochlea was left untreated.

DETAILED DESCRIPTION OF THE INVENTION

Figure 1:
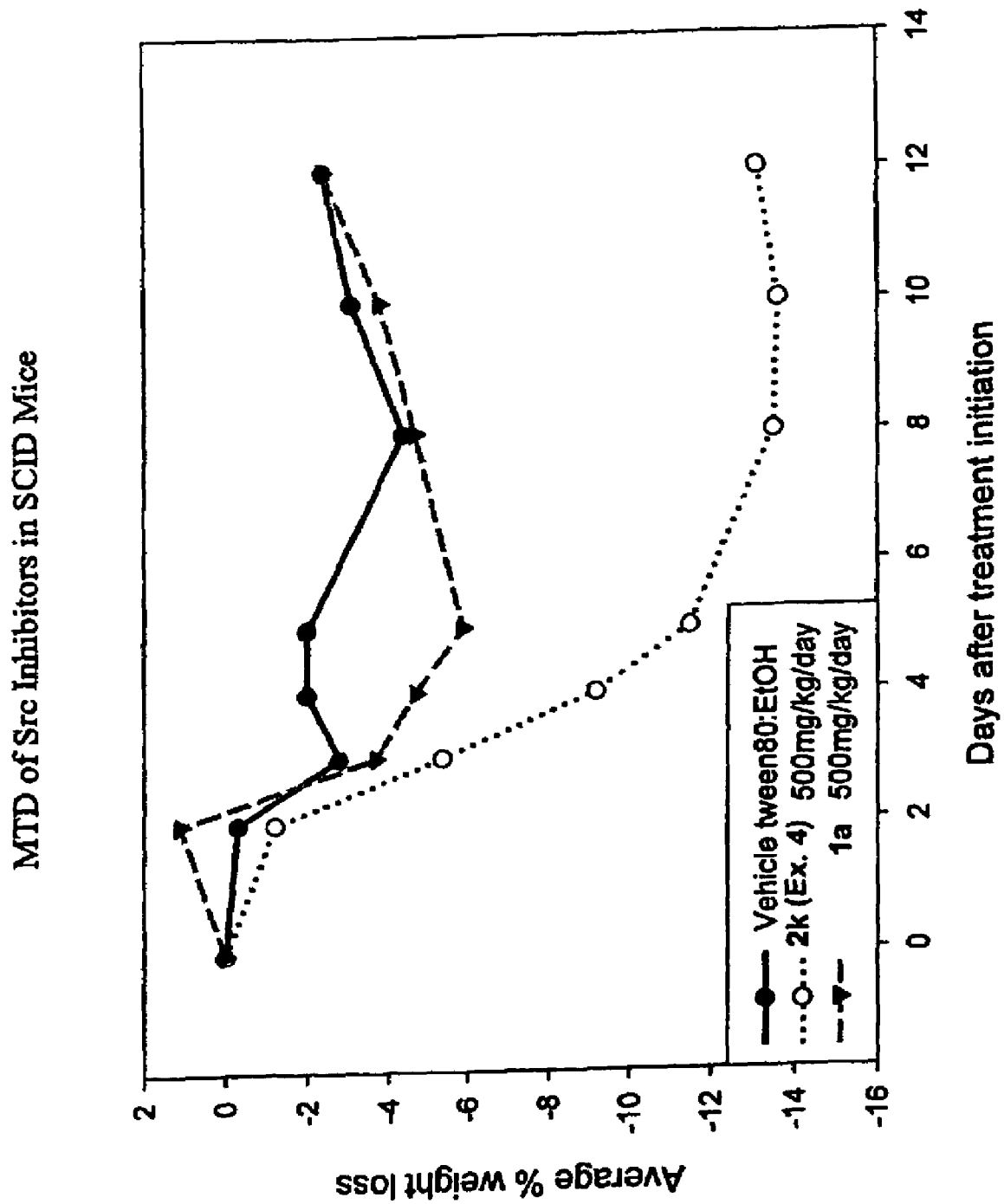
FIG. 1 is a graph showing the maximum tolerated dose (MTD) of two Src inhibitors (1a from Example 1 and 2k from Example 4) in SCID mice.

The present invention relates to a method for protecting against or treating hearing loss in a subject. This method involves administering an effective amount of a protein tyrosine kinase (PTK) inhibitor to the subject to protect against or to treat hearing loss.

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body (Hunter, 1987, 1994, Hanks & Hunter, 1995), and although each of these phosphorylate particular protein/peptide substrates, they all bind the same second substrate ATP in a highly conserved pocket.

Inhibitors of various known protein kinases could have a variety of therapeutic applications provided sufficient selectivity, and acceptable in vivo pharmacological properties, can be incorporated into such inhibitors (Levitzki, 1996a). Perhaps the most investigated potential therapeutic use for protein kinase inhibitors is as anti-cancer agents. This potential application for protein tyrosine kinase ("PTK") inhibitors has been highlighted in many recent reviews (e.g. Lawrence & Niu, 1998, Kolibaba & Druker, 1997, Showalter & Kraker, 1997, Patrick & Heimbrook, 1996, Groundwater et al., 1996, Levitzki, 1995). The foundation for this application is based partly upon the fact that about 50% of the known oncogene products are PTKs and their kinase activity has been shown to lead to cell transformation (Yamamoto, 1993).

The PTKs can be classified into two categories (Courtneidge, 1994), the membrane receptor PTKs (e.g. growth factor receptor PTKs) and the non-receptor PTKs (e.g. the Src family of proto-oncogene products and focal adhesion kinase (FAK)) (Hubbard et al., 2000). There are at least 9 members of the Src family of non-receptor PTK's with pp60$^{c\text{-}src}$ (hereafter referred to simply as "Src") being the prototype PTK of the family wherein the ca. 300 amino acid catalytic domains are highly conserved (Rudd et al., 1993, Courtneidge, 1994). The hyperactivation of Src has been reported in a number of human cancers, including those of the colon (Mao et al., 1997, Talamonti et al., 1993), breast (Luttrell et al., 1994), lung (Mazurenko et a, 1992), bladder (Fanning et al., 1992), and skin (Barnekow et al., 1987), as well as in gastric cancer (Takeshima et al., 1991), hairy cell leukemia (Lynch et al., 1993), and neuroblastoma (Bjelfman et al., 1990). Overstimulated cell proliferation signals from transmembrane receptors (e.g. EGFR and p185HER2/Neu) to the cell interior also appears to pass through Src (Mao et al., 1997, Parsons & Parsons, 1997, Bjorge et al., 1996, Taylor & Shalloway, 1996). Consequently, it has recently been proposed that Src is a universal target for cancer therapy (Levitzki, 1996), because its' hyperactivation (without mutation) is involved in tumor initiation, progression, and metastasis for many important human tumor types (Frame, 2002; Sawyer et al., 2001; Haskell et al., 2001, Martin, 2001; Bridges, 2001; Blume-Jensen et al., 2001; Biscardi et al., 2000; Susa & Teti, 2000; Susa et al., 2000; Irby et al., 2000; Schlessinger, 2000; Abram et al., 2000; Garcia-Echeverria et al., 2000; Sedlacek, 2000; Sridhar et al., 2000; Biscardi et al., 1999).

The PTK inhibitor in the method of the present invention may be a receptor tyrosine kinase inhibitor or a non-receptor tyrosine kinase inhibitor (see Hubbard et al., 2000). In a preferred embodiment of the present invention, the PTK inhibitor is a Src family PTK inhibitor. In this embodiment, the PTK inhibitor may inhibit the activity of any member of the Src family, including pp60$^{c\text{-}src}$ tyrosine kinase. In another preferred embodiment, the PTK inhibitor is a focal adhesion kinase inhibitor.

In one embodiment, the PTK inhibitor is a non-peptide PTK inhibitor. In a preferred embodiment, the non-peptide PTK inhibitor has at least one first module having one or more functional groups each capable of covalently or non-covalently binding to catalytic residues of the protein kinase and a second module which provides a non-peptide scaffold. The combination of the first and second modules inhibits protein kinase activity in the subject. As used herein, a module is a single molecular entity or a collection of functional groups. As used herein, a non-peptide scaffold is a molecule which may include peptide bonds, so long as a part of the molecule is not a peptide.

For example, suitable non-peptide PTK inhibitors have the following formula:

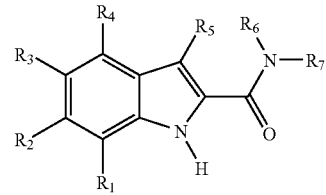

wherein $R_1$ through $R_7$ may be the same or different, and are selected from the group consisting of H, C(O)$R_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$R$_c$, SR$_a$, S(O)$R_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, aryl, heteroaryl, biaryl, heterobiaryl, heterocyclic compound, and alkyl (branched, cyclic, or unbranched), preferably having from one to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl, or $R_5$ and $R_6$ together form a heterocyclic compound. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions. Examples of suitable $R_6$ and $R_7$ groups are provided in Table 1, below. In a preferred embodiment, $R_3$ is a halogen, most preferably, fluorine.

In one embodiment, at least one of $R_6$ or $R_7$ is

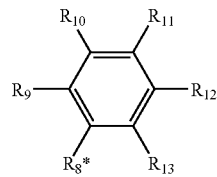

wherein $R_8*$ is the point of attachment and is $(CH_2)_x$, wherein X is from 0 to 10, $CH_2CHOH$, $CH(CH_3)R$, or $CH(CH_3)S$, and each of $R_9$ through $R_{13}$ may be the same or different and are selected from the group consisting of H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), preferably having from one to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that any of $R_9$ through $R_{13}$ and $R_a$ through $R_c$ may be substituted or unsubstituted. In a preferred embodiment, each of $R_9$ through $R_{13}$ may be selected from the group consisting of $OCH_3$, $OCH_2CH_3$, H, $CH_3$, OH, $CH_2OH$, $CF_3$, $OCF_3$, CFO, $C_6H_5$, $OC_6H_5$, $OCH_2C_6H_5$, $OCH_2CH_2CH_3$, CHO, $CO_2H$, $CO_2CH_3$, $CH_2CO_2H$, $CH_2CO_2CH_3$, $NO_2$, and halogen.

In another embodiment, at least one of $R_6$ or $R_7$ is

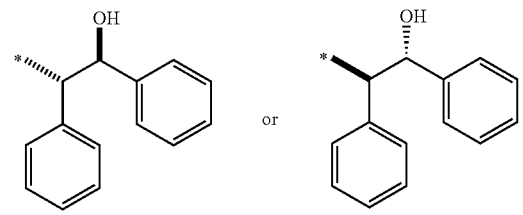

wherein the asterisk indicates the point of attachment to the nitrogen.

Another non-peptide PTK inhibitor useful in the method of the present invention has the following formula:

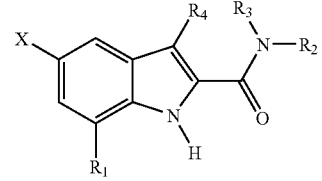

wherein X is a halogen, preferably, fluorine, and $R_1$ through $R_4$ are specificity elements. As used herein, specificity elements or specificity side chains are side chains which will bind in unique binding pockets for the individual PTKs. Thus, the side chains used will depend on the particular protein kinase to be inhibited. To identify suitable side chains, known peptide binding side chains may be used to identify analogues which are then used in combinatorial chemistry techniques to expand the library of possible side chains.

In one embodiment, $R_1$ is H, $R_2$ is

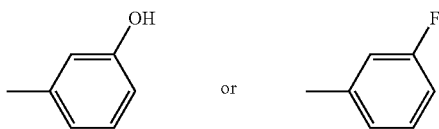

$R_3$ is H, and $R_4$ is H. The compound may also be substituted at any other position on the indole ring.

A further non-peptide PTK inhibitor has the formula

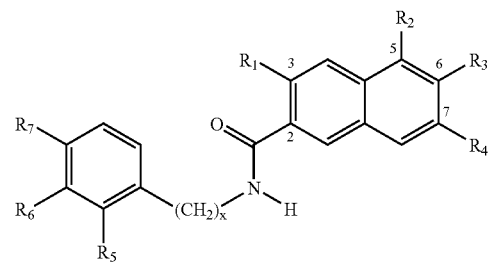

wherein $R_1$ through $R_7$ are each the same or different and are selected from the group consisting of H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), preferably having from one to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions. X is preferably 0 or 1.

Preferred first modules have a two or more functional groups, selected from the group consisting of a halogen, a boronic acid group, a hydroxyl group, phosphonic acid, sulfamic acid, a guanidino group, carboxylic acid, an aldehyde, an amide, and hydroxymethylphosphonic acid. More preferred functional groups are halogens, boronic acid groups, a hydroxyl group, or an amide group. An even more preferred amide group is a vicinal tricarbonyl amide.

Preferred second modules include indole, naphthalene, biphenyl, isoquinoline, benzofuran, and benzothiophene. More preferred second modules are an indole or naphthalene. In some embodiments of the invention more than one first module may be bound to the second module. In addition, the first module may have a linear chain comprising between one and three carbon atoms which links the first module to the second module. In alternative embodiments, one of the carbon atoms in the linear chain is substituted with a nitrogen, oxygen, or sulfur atom.

Examples of other suitable non-peptide PTKs include:

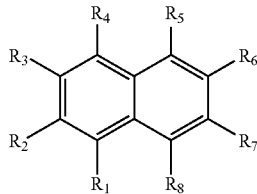

wherein any of the individual R's can be a first module $(M_1)$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

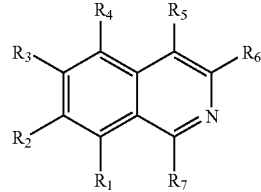

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

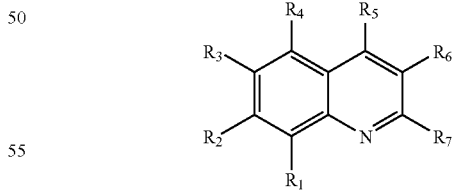

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

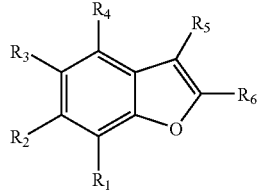

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

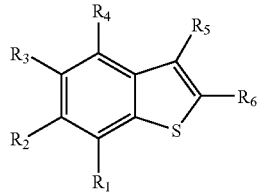

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

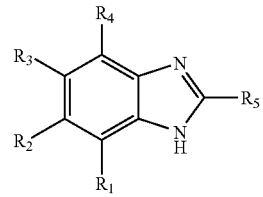

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

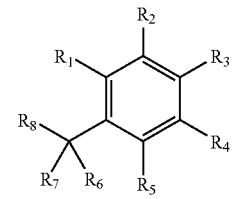

wherein any of the individual R's can be $M_1$, and the remaining R groups can be H, $C(O)R_a$, $C(O)NR_aR_b$, $C(O)$ OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$ OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

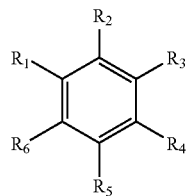

wherein any of the individual R's can be M$_1$, and the remaining R groups can be H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$ OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)N-R$_a$R$_b$, S(O)$_2$NR$_a$R$_b$, P(O)OR$_a$OR$_b$, B(OH)$_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

heterobiaryl. It is understood that all open substitution positions in the above side chains can contain further substitutions;

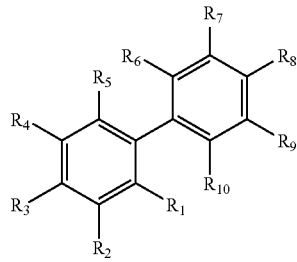

wherein any of the individual R's can be M$_1$, and the remaining R groups can be H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$ OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions.

In a preferred embodiment of the invention, the first module is produced by attaching the first module to a peptide scaffold. One or more functional groups are identified which preferentially bind to catalytic residues of the protein kinase. Further, the first module is combined with the second module so that the second module substitutes for the peptide scaffold. For a detailed description of a method for designing protein kinase inhibitors, see U.S. patent application Ser. No. 09/482,585, which is hereby incorporated by reference in its entirety.

The method of the present invention may further consist of adding one or more specificity side chain elements to the combination of the first and second modules, as described above. Specificity side chains can increase potency and specificity of the inhibitor.

Once a promising second module is identified it is not necessary to repeat all the steps of the method. Rather, the first module, specificity side chains, or a combination the two may be modified to improve the original inhibitor, i.e an inhibitor which has an increased ability to inhibit protein kinase activity when compared to the unmodified first inhibitor.

This method is designed to preferentially provide non-peptide protein kinase inhibitors which do not act by inhibiting ATP binding to the protein kinase. Inhibitors of protein kinases which act by inhibiting ATP binding may be potent, but often lack specificity. Therefore, protein kinase inhibitors which inhibit protein kinase activity but do not inhibit or only weakly inhibit ATP binding to the protein kinase are preferred.

The compounds can be tested for an ability to inhibit protein kinase activity, for example, by measuring the activity of the protein kinase in the presence of the inhibitor at the same temperature, pH, ionic strength, osmolarity, and free magnesium concentration as found in a cell which expresses the protein kinase. The level of protein kinase activity is compared to the level of activity from the protein kinase without the presence of the inhibitor. Such an assay system which mimics physiological conditions provides the most relevant inhibition data. The assay may be conducted in an automated assay system. Furthermore, the assay may be combined with a combinatorial chemistry method to rapidly screen numerous candidates.

In yet another embodiment, the PTK inhibitor is a peptide protein tyrosine kinase inhibitor. Suitable peptide PTK inhibitors are described, for example, in Lai et al., 1998.

In one embodiment, the PTK inhibitor in the method of the present invention is a peptide substrate directed inhibitor. As used herein, a peptide substrate directed inhibitor is an inhibitor which binds to the peptide substrate specificity sites of the active site of the tyrosine kinase and does not bind to ATP. The above-described non-peptide PTK inhibitors are examples of peptide substrate directed inhibitors.

In another embodiment, the PTK inhibitor is an ATP site directed inhibitor. As used herein, an ATP site directed inhibitor is an inhibitor that binds ATP to competitively inhibit a PTK. Examples of ATP site inhibitors include, but are not limited to, flavanoids, genistein, and lavendustin A. Examples of ATP site inhibitors (antagonists) are disclosed, for example, in Levitzki and Gazit, 1995.

In yet another embodiment, the PTK inhibitor is Src homology 2 (SH2) site inhibitor. An SH2 site inhibitor binds to the SH2 site to inhibit the activity of the PTK. Examples of suitable SH2 inhibitors are described, for example, in Garcia-Echeverria, 2001, Muller, 2001, Fretz et al., 2000, and Vu, 2000.

In a further embodiment, the PTK inhibitor is a Src homology 3 (SH3) site inhibitor. An SH3 site inhibitor binds to the SH3 site to inhibit the activity of the PTK. Examples of suitable SH3 inhibitors are described, for example, in Stein, 1998 and Sparks et al., 1994.

In another embodiment, the PTK inhibitor is an allosteric inhibitor. As used herein, an allosteric inhibitor binds to an allosteric site other than the active site of the PTK, thereby changing the conformation of the PTK and inhibiting activity of the PTK.

The above PTK inhibitors may bind covalently or non-covalently (reversibly or irreversibly) to their respective sites.

The PTK inhibitors can be administered orally (e.g., in food), parenterally, subcutaneously, intravenously, intramuscularly, intraperitoneally, by intranasal instillation, by intracavitary or intravesical instillation, intraauditorily, intraarterially, intralesionally, by metering pump, or by application to mucous membranes. They may be administered alone or with pharmaceutically or physiologically acceptable carriers, excipients, or stabilizers, and can be in solid or liquid form, such as tablets, capsules, powders, solutions, suspensions, or emulsions.

The solid unit dosage forms can be of the conventional type. The solid form can be a capsule, such as an ordinary gelatin type containing the PTK inhibitor and a carrier, for example, lubricants and inert fillers, such as lactose, sucrose, or cornstarch. In another embodiment, these PTK inhibitors can be tableted with conventional tablet bases, such as lactose, sucrose, or cornstarch, in combination with binders, like acacia, cornstarch, or gelatin, disintegrating agents, such as cornstarch, potato starch, or alginic acid, and lubricants, like stearic acid or magnesium stearate.

The PIK inhibitors may also be administered in injectable dosages by solution or suspension of these materials in a physiologically acceptable diluent with a pharmaceutical carrier. Such carriers include sterile liquids, such as water and oils, with or without the addition of a surfactants, adjuvants, excipients, or stabilizers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

For use as aerosols, the PTK inhibitor in solution or suspension may be packaged in a pressurized aerosol container together with suitable propellants, for example, hydrocarbon propellants like propane, butane, or isobutane, and with conventional adjuvants. The PTK inhibitor can also be administered in a non-pressurized form, such as in a nebulizer or atomizer.

Suitable dosages are determined based on a variety of factors, but may include from about 50 mg/kg to about 1000 mg/kg of PTK inhibitor, preferably from about 50 mg/kg to about 400 mg/kg of PTK inhibitor (see, e.g., Bakhtiar et al., 2002; Druker, 2002).

The PTK inhibitors described herein may be administered to any subject, such as any member of the class Mammalia including, without limitation, humans and non-human primates, such as chimpanzees and other apes and monkey species; farm animals including cattle, sheep, pigs, goats and horses; domestic animals including cats and dogs; laboratory animals including rodents, such as mice, rats, and guinea pigs, and the like. The term does not denote a particular age or sex.

As described herein, the PTK inhibitors may be used to protect against or prevent hearing loss in a subject. In order to protect against hearing loss, the PTK inhibitor may be administered prior to noise exposure or exposure to a drug which induces hearing loss. Such drugs may include chemotherapeutic drugs (e.g., platinum-based drugs which target hair cells) and aminoglycoside antibiotics.

Alternatively, the PTK inhibitors may be used to treat hearing loss in a subject. In this embodiment, the PTK inhibitor is administered to the subject subsequent to the initiation of hearing loss to reduce the level of hearing loss.

Although not wishing to be bound by theory, it is believed that the administration of PTK inhibitors prevents apoptosis of cochlear hair cells, thereby preventing hearing loss. In particular, following noise exposure, the tight cell junctures between the cochlear hair cells, as well as the cell-extracellular matrix interaction, are torn and stressed. The stressing of these tight cell junctures initiates apoptosis in the cells through a complex signaling pathway, in which the Src family of PTKs act as molecular switches, interacting with focal adhesion kinase to transduce signals of cell-matrix disruptions to the nucleus. It is believed that the administration of PTK inhibitors prevents the initiation of apoptosis in this cascade.

The 5-fluoro indoles described above provide activity against tyrosine kinases, such as $pp60^{c-src}$, and, in addition, are expected to improve the ability of the compound to inhibit tyrosine kinases in vivo, since one easily metabolized OH group has been removed. In particular, the 5-position on the indole ring has been substituted with a halogen. The halogen is a hydrogen bond acceptor, useful with catalytic residues which are hydrogen bond donors. In addition, the halogen is not metabolized in phase II metabolism and is electronegative, leading to in vivo benefits (see, e.g., Park et al., 2001). Some members of this class are also inhibitors of the opposing enzymes, i.e., phosphotyrosine phosphatases.

The inhibitors described above are inhibitors of pp60c-src, of highly metastatic prostate cancer cell growth, and are non-toxic in mice upon high dose acute i.p. administration, as described in Examples 1-4, 7, and 8, below. Some of these compounds may be found to have other biological activities upon broader testing (e.g., inhibit glycogen phosphorylase for Type II diabetes, HIV reverse transcriptase, or thromboxane synthase). Thus, these compounds may be used as tyrosine kinase inhibitors in combination therapeutic applications. For example, the PTK inhibitor may be administered to a subject in an amount and under conditions effective to treat or prevent hearing loss and to treat cancer (e.g., where a synergistic activity is found). Tyrosine kinase inhibitors have other potential therapeutic applications as well (e.g., immunosuppressants in the case of p56lck) and inhibitors of the tyrosine phosphatase PTP-1B may provide drugs for treating Type II diabetes. Therefore, the PTK inhibitors disclosed herein may be used in a variety of combination therapies.

EXAMPLES

Example 1

Synthesis and Activity of Indole Derivative Protein Kinase Inhibitors

The following results show the solution phase synthesis of 5-fluoroindole-2-carbaxamide libraries and testing of indole derived protein kinase inhibitors. These final products are examples of indole-based tyrosine kinase inhibitors wherein synthesis with a 5-fluoro group is illustrated.

A. Synthesis of Intermediates and Sample Reagents:

5-fluoro-3-phenylindole-2-carboxylic acid

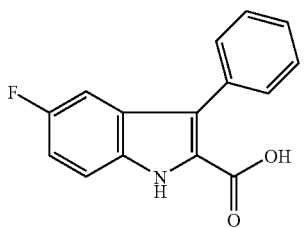

(a) Preparation of Methyl Ester

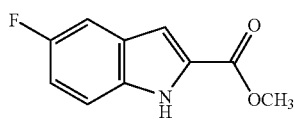

A mixture of 5-fluoroindole-2-carboxylic acid (6 g, 33.5 mmol) and a freshly prepared methanolic HCl (100 mL) was stirred overnight at room temperature. The precipitated ester was collected by filtration, washed with NaHCO$_3$ saturated solution, water, and MeOH. The filtrate was treated with saturated NaHCO$_3$ and extracted with EtOAc. The organic layer was washed with brine, dried (MgSO$_4$), and evaporated in vacuo. The product ester (6 g) was an off white solid and it was used for the next step without further purification: MP 200-201° C.; $^1$H NMR (CDCl$_3$, 500 MHz) δ 8.94 (br, 1H), 7.33 (dd, 1H, J=9.2 and 4.3 Hz), 7.30 (dd, 1H, J=2.2 and 9.2), 7.15 (d, 1H, J=2.1 Hz), 7.07 (ddd, 1H, J=2.5, 8.9 and 9.1 Hz), 3.92 (s, 3H)

(b) Preparation of the 3-Iodo Derivative

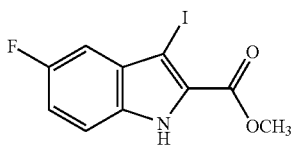

4.22 g (21.8 mmol) of the methyl ester was dissolved in DMF (25 mL). In another flask, a solution of iodine (6.09 g, 24 mmol) and KOH (4.65 g, 82.9 mmol) in DMF (25 mL) was stirred for 30 minutes and added dropwise to the ester solution over 5 minutes. After stirring for 10 minutes at room temperature, the reaction was quenched by pouring into a solution of NaHSO$_3$ (2.2 g), NH$_4$OH (25% solution in H$_2$O) in 300 mL water. The mixture was stirred for 30 minutes then the precipitated solid product was collected by filtration and washed with H$_2$O: $^1$H NMR (CDCl$_3$, 500 MHz) δ 9.17 (br, 1H), 7.33 (dd, 1H, J=9.0 and 4.2 Hz) 7.21 (dd, 1H J=9.0 and 2.0 Hz), 7.12 (dt, 1H, J=9.0 and 2.0 Hz), 3.81 (s, 3H).

(c) Suzuki Coupling

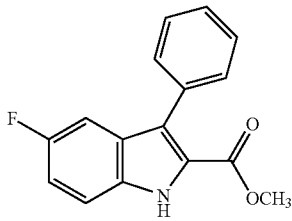

The iodo derivative was mixed with benzeneboronic acid (2.76 g, 22 mmol), PdCl$_2$(PPh$_3$)$_2$ (0.7 g, 1 mmol), and 50 mL of 2M Na$_2$CO$_3$ in dioxane (200 mL). The mixture was stirred at 90° C. overnight. The solvent was evaporated under vacuum. The product was extracted with EtOAc (3×200 mL). The combined extract was washed with brine, dried with MgSO$_4$, and purified by crystallization (CH$_2$Cl$_2$-hexane) and silica gel chromatography (Hexane-EtOAc 4:1): MP 189° C.; $^1$H NMR (CDCl$_3$, 500 MHz) δ 8.94 (br, 1H), 7.51 (dd, 2H, J=1.5 and 7.9 Hz), 7.45 (ddd, 2H, J=1.8, 7.3 and 7.8), 7.39-7.34 (complex, 2H), 7.25 (dd, 1H, J=2.5 and 8.7 Hz), 7.10 (ddd, 1H, J=2.5, 8.9 and 9.1 Hz), 3.80 (s, 3H).

(d) Saponification of Methyl Ester

The ester described above (2.5 g, 9.28 mmol) was dissolved in THF (30 mL).

A solution of LiOH (2.4 g, 100 mmol) in water (20 ml) was added and the mixture was heated at reflux for 1 hour. The mixture was cooled to room temperature and THF was removed by vacuum evaporation. The mixture was treated with 2M HCl until it became acidic. The product was extracted with EtOAc. The organic layer was washed, dried (brine, Na$_2$SO$_4$), and concentrated under vacuum. The crude solid product was redissolved in NaHCO$_3$ (saturated solution) and washed several times with CH$_2$Cl$_2$. The aqueous layer was acidified with ice and 2M HCl and extracted with EtOAc. After washing, drying, and rotavaping, the product was collected as white solid (yield 2.3 g, 97%): MP 195-196° C.; $^1$H NMR (CDCl$_3$, 500 MHz) δ 8.94 (br, 1H), 7.52 (dd, 2H, J=1.8 and 7.9 Hz), 7.46 (ddd, 2H, J=1.8, 7.3 and 7.6), 7.40 (ddd, 1H, J=1.8, 7.4 and 7.8 Hz), 7.37 (dd, 1H, J=9.0 and 4.2 Hz), 7.25 (dd, 1H, J=2.5 and 8.7 Hz), 7.12 (ddd, 1H, J=2.4, 8.8 and 8.9. Hz).

3-benzyloxy-5-hydroxybenzonitrile

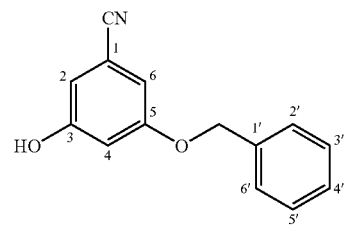

To a mixture of 3,5-dihydroxybenzonitrile (1.08 g, 8 mmol) and K$_2$CO$_3$ (1.104 g, 8 mmol) and in CH$_3$CN (50 mL) benzyl bromide (1.438 g, 8 mmol) was added. The mixture was heated to reflux for 2 hours. Solvent was evaporated under vacuum. The residue was treated with EtOAc (200 mL) and 1M HCl (200 mL). The organic layer was washed, dried, and evaporated in vacuo. The residue was chromatographed (gradient, Hexanes-CH$_2$Cl$_2$-MeOH) to give 3-benzyloxy-5-hydroxybenzonitrile (529 mg, 29%), 3,5-dibenzyloxybenzonitryl (784 mg, 31%) and 256 mg (23.7 mg, 24%) of the starting material. The product 3-benzyloxy-5-hydroxybenzonitrile had: MP 144-145° C.; $^1$H NMR δ 9.15 (s, 1H, <u>OH</u>), 7.47 (d, 2H, J=7.0 Hz, <u>2'and6'</u>), 7.40 (ddd, 2H, J=7.0, 7.0, 2.0 Hz, <u>3'and5'</u>), 7.34 (dd, 1H, J=7.7 and 2.1 Hz, <u>4'</u>), 6.89 (dd, 1H, J=1.5 Hz, <u>4</u>), 6.78 (d, 2H, J=1.8 Hz), 5.16 (s, 2H).

3,5-dibenzyloxybenzonitryl

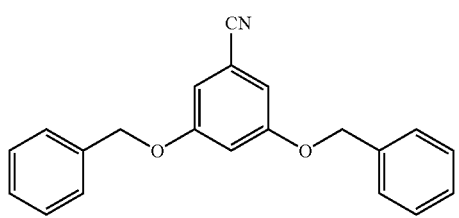

This compound had MP 106° C.; $^1$H NMR (CDCl$_3$, 500 MHz) δ 7.38 (complex, 10H), 6.83 (d, 2H, J=2.1 Hz), 6.79 (d, 1H, J=2.1 Hz).

4-benzyloxy-3-hydroxybenzonitrile

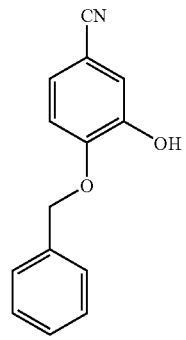

A mixture of 3,4-dihydroxybenzonitrile (540 mg, 4 mmol), K$_2$CO$_3$ (552 mg, 4 mmol) and benzyl bromide (476 mg, 4 mmol) in acetone (20 mL) was stirred at room temperature for 3 days. The mixture was evaporated under vacuum and subjected to flash column chromatography (2% MeOH in toluene-hexane, 2:1) to give the desired product (224 mg, 25%): MP 101° C.; $^1$H NMR (Acetone-d$_6$, 500 MHz) δ 8.55 (s, 1H), 7.50 (d, 2H, J=7.3 Hz), 7.39 (dd, 2H, J=7.0 and 7.3), 7.34 (dd, 1H, J=7.0 and 7.3), 7.2 (m, complex, 3H), 5.25 (s, 2H).

3-hydroxy-4-propyloxybenzonitrile

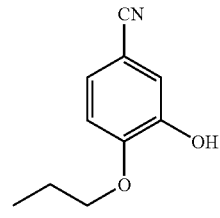

This compound was prepared following a similar procedure used to prepare 4-benzyloxy-3-hydroxybenzonitrile in 27% yield: MP 99° C.; $^1$H NMR (Acetone-d$_6$, 500 MHz) δ 8.33 (s, 1H), 7.21 (dd, 1H, J=8.2 and 1.8 Hz), 7.13 (d, 1H, J=1.8 Hz), 7.08 (d, 1H, J=8.3 Hz), 4.07 (t, 2H, J=6.4 Hz), 1.80 (m, 2H), 1.01 (t, 3H, J=7.3 Hz).

3-benzyloxy-5-hydroxybenzylamine

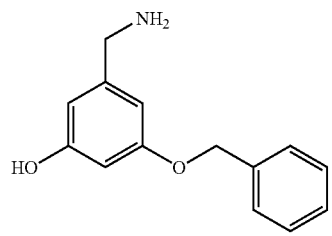

3-benzyloxy-5-hydroxybenzonitrile (225 mg, 1 mmol) was dissolved in 2 mL THF. 2 mL of BH$_3$-THF (1.5 M in THF and ether) was added dropwise, then the mixture was heated at reflux temperature for 3 hours. After cooling, the mixture was carefully poured to 3M HCl (ice cooled) and allowed to stir for 20 hours at room temperature. The mixture was neutralized with solid NaHCO$_3$, thus the product precipitated as a white solid. The product was collected by filtration, washed with water, and dried (140 mg, 61%): MP 164-166° C. (dec); $^1$H NMR (DMSO-d$_6$, 400 MHz) δ 9.28 (br, 1H), 7.41 (d, 2H, J=6.9 Hz), 7.36 (dd, 2H, J=7.0 and 7.6 Hz), 7.30 (dd, 1H, J=7.0 and 6.6 Hz), 6.43 (s, 1H), 6.32 (s, 1H), 6.21 (dd, 1H, J=2.2 and 2.0 Hz), 4.99 (S, 2H), 3.57 (S, 2H).

3,5-dibenzyloxybenzylamine

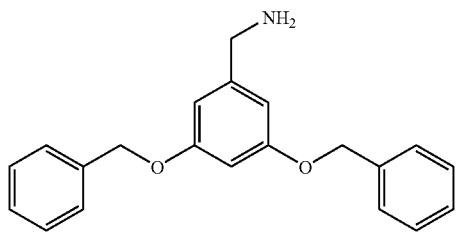

This compound was prepared according to the procedure used in preparation of 3-benzyloxy-5-hydroxybenzylamine. The reaction was quenched via addition of MeOH and the mixture was left to stir overnight. The solvent was removed and the product was obtained by flash column chromatography (CH$_2$Cl$_2$-Hexanes containing 5% MeOH) as clear thick oil (90%): $^1$H NMR (Acetone-d$_6$, 500 MHz) δ 7.46 (d, 4H, J=7.6), 7.37 (dd, 4H, J=7.3 and 7.6), 7.31 (dd, 2H, J=7.3 and 7.0), 6.65 (d, 1H, J=2.1 Hz), 6.64 (d, 1H, J=2.0 Hz), 6.52 (dd, 1H, J=2.0 and 2.2 Hz), 5.07 (s, 4H), 4.35 (s, 2H), 1.97 (br, 1H), 1.85 (br, 1H).

4-benzyloxy-3-hydroxybenzylamine

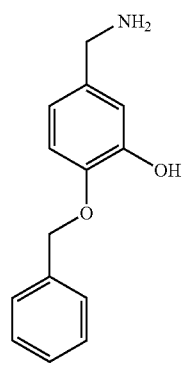

This compound was prepared according to procedure used in preparation of 3,5-dibenzyloxybenzylamine, starting from 4-benzyloxy-3-hydroxybenzonitrile. Yield was 33%. MP 122-125° C.; $^1$H NMR (DMSO-d$_6$, 400 MHz) δ 8.9 (br, 1H), 7.44 (d, 2H, J=7.4 Hz), 7.35 (dd, 2H, J=7.0 and 7.7 Hz), 7.28 (dd, 1H, J=7.0 and 7.3), 6.85 (d, 1H, J=7.6 Hz), 6.77 (d, 1H, J=2.1 Hz), 6.61 (dd, 1H, J=7.4 and 2.2 Hz), 5.05 (s, 2H), 3.55 (s, 1H), 2.50 (br, 2H).

3-hydroxy-4-propyloxybenzylamine

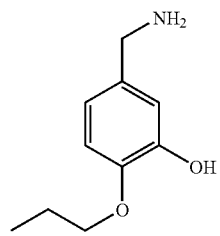

This compound was prepared by reduction of 3-hydroxy-4-propyloxybenzonitrile according to procedure described in preparation of 3,5-dibenzyloxybenzylamine. Yield was 48%: MP 110-113° C. (dec.); $^1$H NMR (CDCl$_3$, 400 MHz) δ 6.86 (s, 1H), 6.77 (d, 1H, J=8.4 Hz), 6.74 (d, 1H, J=8.1 Hz), 3.95 (t, 1H, J=6.6 Hz), 3.74 (s, 2H), 2.01 (br, 2H), 1.82 (m, 2H), 1.02 (t, 3H, J=7.4 Hz).

4-hydroxymethylbenzylamine

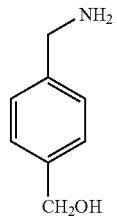

This compound was prepared by reduction of 4-cyanobenzaldehyde according to the procedure described in preparation of 3,5-dibenzyloxybenzylamine. Yield was 46%: MP 102-123° C.; $^1$H NMR (Acetone-d$_6$, 500 MHz) 7.27 (m, complex 4H), 4.58 (s, 2H), 3.72 (s, 2H), 3.69 (s, 1H) 2.77 (br, 1H), 2.45 (br, 1H);

3-hydroxymethylbenzylamine

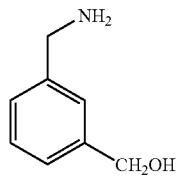

This compound was prepared by reduction of 3-cyanobenzaldehyde according to the procedure described in preparation of 3,5-dibenzyloxybenzylamine. Yield was 66%: $^1$H NMR (Acetone-d$_6$, 500 MHz) δ 7.32 (s, 1H), 7.23 (dd, 1H, J=7.6 and 7.0), 7.19, complex, 2H), 4.59 (s, 2H), 4.40 (s, 2H), 4.10 (br, 1H), 1.96 (br, 1H), 1.88 (br, 1H).

2-methoxy-5-nitrobenzaldehyde methyl hemiacetal

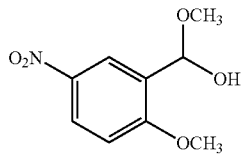

2-hydroxy-5-nitrobenzaldehyde (3.34 g, 20 mmol) was dissolved in acetone (70 mL). $K_2CO_3$ (5.53 g, 40 mmol) and iodomethane (14.19 g, 100 mmol) was added and the solution was heated to reflux overnight. Solvent was removed in vacuo and residue was dissolved in EtOAc. The resulting product was washed with 2M NaOH, water, and brine and dried. Removal of solvent resulted in a solid product (2.5 g, 69%) of 2-methoxy-5-nitrobenzaldehyde methyl hemiacetal: MP 147-148° C. (89° C. reported for the aldehyde); $^1$H NMR (CDCl$_3$, 400 MHz) δ 8.43 (d, 1H, J=2.9 Hz), 8.24 (dd, 1H, J=2.6 and 9.1 Hz), 7.78 (d, 1H, 16.5 Hz), 6.99 (d, 1H, J=9.1 Hz), 6.83 (d, 1H, J=16.4 Hz). NOTE: This NMR was taken after about 10 months and the hemiacetal was still existing and pure.

5-nitro-2-propyloxybenzaldehyde

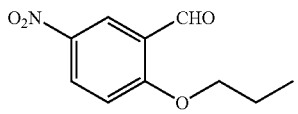

This compound was prepared by the reaction of 2-hydroxy-5-nitrobenzaldehyde and 1-iodopropane using a similar procedure as described in the preparation of 2-methoxy-5-nitrobenzaldehyde methyl hemiacetal. Yield was 72%: MP 51-52° C.; $^1$H NMR (500 MHz, CDCl$_3$) δ 10.46 (s, 1H), 8.68 (d, 1H, J=2.9 Hz), 8.39 (dd, 1H, J=2.7 and 9.1 Hz), 7.08 (d, 1H, J=9.1 Hz), 4.16 (t, 2H, J=6.2), 1.93 (m, 2H), 1.98 (t, 3H, J=7.37).

2-hydroxymethyl-4-nitrophenol

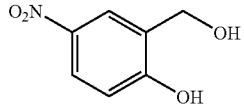

A solution of 2-hydroxy-5-nitrobenzaldehyde (5.01 g, 30 mmol) in a mixture of 60 mL 1M NaOH and 30 mL MeOH was cooled to 0° C. NaBH$_4$ (1.13 g, 30 mmol) solution in 15 ml 1M NaOH and 5 mL MeOH was added slowly. The reaction mixture was stirred for 24 hours at room temperature. The mixture was poured into ice cooled 2M HCl and extracted with EtOAc. The organic layer was washed, dried, and evaporated in vacuo to give the alcohol as a yellow solid (5.1 g, 100%): MP 112-114° C.; $^1$H NMR (DMSO-d$_6$, 400 MHz) δ 11.08 (s, 1H), 8.18 (d, 1H, J=2.5 Hz), 8.00 (dd, 1H, J=2.5 and 8.7 Hz), 6.92 (d, 1H, J=8.8 Hz), 5.20 (br, 1H), 4.49 (s, 2H).

2-methoxy-5-nitrobenzylalcohol

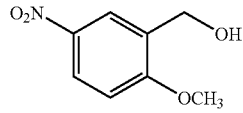

This compound was prepared by reduction of 2-methoxy-5-nitrobenzaldehyde methyl hemiacetal using a method similar to that described for preparing 2-hydroxymethyl-4-nitrophenol in 76% yield: MP 121-122° C.; $^1$H NMR (DMSO-d$_6$, 500 MHz) δ 8.22 (d, 1H, J=1.22 Hz), 8.16 (dd, 1H, J=2.7 and 9.1), 7.16 (d, 1H, J=8.9 Hz), 4.50 (s, 2H), 3.90 (s, 3H).

5-nitro-2-propyloxy-benzylalcohol

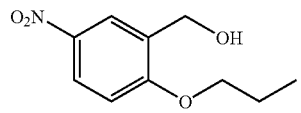

This compound was prepared by reduction of 5-nitro-2-propyloxybenzaldehyde using a method similar to that described for preparing 2-hydroxymethyl-4-nitrophenol in 93% yield: MP (No Sample left for MP); $^1$H NMR (400 MHz, DMSO-d$_6$) 8.22 (d, 1H, J=2.6 Hz), 8.13 (dd, 1H, J=2.9 and 9.2 Hz), 7.14 (d, 1H, J=9.2 Hz), 5.41 (t, 1H, J=5.5 Hz), 4.52 (d, 2H, J=5.8 Hz), 4.08 (t, 2H, J=6.2), 1.75 (m, 2H), 0.98 (t, 3H, J=7.6 Hz).

2-benzyloxy-5-nitrobenzylalcohol

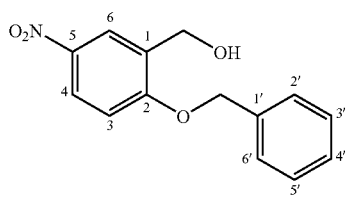

This intermediate was prepared by alkylation of 2-hydroxymethyl-4-nitrophenol with benzyl bromide following the method described for preparation of 2-methoxy-5-nitrobenzaldehyde methyl hemiacetal in a yield of 84%: MP 81-83° C.; $^1$H NMR (DMSO-d$_6$, 500 MHz) 8.26 (d, 1H, J=2.9 Hz H-6), 8.15 (dd, 1H, J=2.9 and 9.1 Hz, H-4), 7.46 (d, 2H, J=7.0, 2',6'-Hs) 7.41 (dd, 2H, J=7.0 and 7.7, 3',5'Hs), 7.34 (d, 1H, J=7 Hz, 4'-H), 7.25 (d, 1H, J=9.1 Hz, 3-H), 5.4 (br, 1H, OH), 5.29 (s, 2H, CH$_2$), 4.57 (s, 2H, CH$_2$).

3-hydroxymethyl-4-methoxyaniline

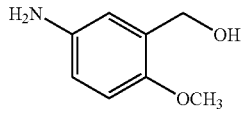

A mixture of 2-methoxy-5-nitrobenzylalcohol (1.02 g, 6.03 mmol) and SnCl$_2$.H$_2$O (6.8 g, 30.15 mmol) in EtOH (20 mL) was heated at 70° C. for 1 hour. After cooling, the mixture was treated with 2M NaOH and extracted with ether. The organic layer was washed with water, dried, and evaporated under vacuum to provide 2.18 g (84%) of the aniline 3-hydroxymethyl-4-methoxyaniline: $^1$H NMR (DMSO-d$_6$, 500 MHz) δ 6.66 (d, 1H, J=2.2 Hz), 6.61 (d, 1H, J=8.6 Hz), 6.38 (dd, 1H, J=2.4 and 8.2 Hz), 4.81 (t, 1H, J=5.5 Hz), 4.54 (br, 2H), 4.37 (d, 2H, J=5.8 Hz), 3.61 (s, 3H).

3-hydroxymethyl-4-propyloxyaniline

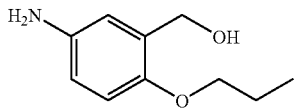

This compound was prepared by reduction of 5-nitro-2-propyloxy-benzylalcohol using the method described for the preparation of 3-hydroxymethyl-4-methoxyaniline in 37% yield: $^1$H NMR (DMSO-d$_6$, 500 MHz) δ 6.66 (d, 1H, J=2.5 Hz), 6.60 (d, 1H, J=8.6 Hz), 6.35 (dd, 1H, J=2.7 and 8.5 Hz), 4.79 (t, 1H, J=5.8 Hz), 4.54 (br, 2H), 4.37 (d, 2H, J=6.1 Hz), 3.74 (t, 2H, J=6.4 Hz), 1.65 (m, 2H), 0.94 (t, 3H, J=7.4 Hz).

4-benzyloxy-3-hydroxymethylaniline

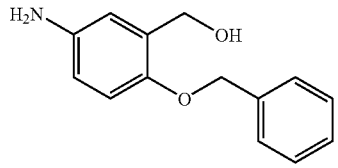

This compound was prepared by reduction of 2-benzyloxy-5-nitrobenzylalcohol using the method described for preparation of 3-hydroxymethyl-4-methoxyaniline in 86% yield: $^1$H NMR (DMSO-d$_6$, 500 MHz) δ 7.40 (d, 2H, J=7.3 Hz), 7.36 (dd, 2H, J=7.3 and 7.6 Hz), 7.28 (dd, 1H, J=7.0 and 7.4), 6.70 (d, 1H, J=8.5 Hz), 6.68 (d, 1H, J=2.4 Hz), 6.35 (dd, 1H, J=2.8 and 8.3 Hz), 4.92 (s, 2H), 4.84 (t, 1H, J=5.8 Hz), 4.59 (br, 2H), 4.44 (d, 2H, J=6.4 Hz).

B. Formation of Libraries

General Structure

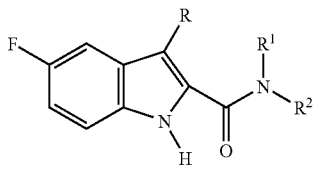

R = H, Ph
R$^1$, R$^2$ = H, alkyl, aryl, aralkyl, heterocyclic

1. General Procedures for Amide Coupling a. Method A

To a cold mixture (at 0° C.) of an amine (see Table 1 below for amines) (0.15 mL of 1M solution in CH$_2$Cl$_2$, 0.15 mmol), an acid (5-fluoroindole-2-carboxylic acid or 5-fluoro-3-phenylindole-2-carboxylic acid) (0.15 mmol as 0.15 mL of 1M solution in THF) in CH$_2$Cl$_2$ (0.5 mL) was added and cooled to 0° C. Subsequently, a mixture of 1-(3-dimethylaminopropyl)-3-ethylcarbodiimide hydrochloride (EDCI) (0.15 mmol) and Et$_3$N (0.06 mmol) in CH$_2$Cl$_2$ (0.5 mL) was added and the reaction was shaken in a Bohdan orbital shaker (Mettler-Toledo Bohdan, Vernon Hills, Ill.) at 0° C. for 30 minutes then at room temperature for 18 hours. After adding 0.5 mL of CH$_2$Cl$_2$ and 0.5 mL MeOH, the mixture was passed through a cartridge charged with a cationic exchange resin (Dowex 50wX4-200, Aldrich Chemical Co., Milwaukee, Wis., pre-washed with 1M HCl, H$_2$O, H$_2$O-MeOH, MeOH, MeOH—CH$_2$Cl$_2$). The eluent was directly passed through a chromatography cartridge containing silica gel mixed with 10% Na$_2$CO$_3$. The product was eluted with 2 mL CH$_2$Cl$_2$-MeOH (2 mL), CH$_2$Cl$_2$ (2 mL), and CH$_2$Cl$_2$-MeOH (2 mL). The fraction(s) containing pure product was identified by TLC (EtOAc-Hexane, 1:1). The compounds were characterized and their relative purity was estimated using $^1$H NMR.

b. Method B

A mixture of an amine (see Table 1 below for amines) (0.1 mmol), an acid (5-fluoroindole-2-carboxylic acid or 5-fluoro-3-phenylindole-2-carboxylic acid) (0.1 mmol as 0.1 mL of 1M solution in DMF), and diisopropylethylamine (DIEA) (0.05 mL, 0.3 mmol) was cooled to 0° C. (benzotriazol-1-yloxy)tripyrrolidino-phosphonium-hexafluorophosphate (PyBOP) (0.1 mmol as 0.1 mL of 1M solution in DMF) was added. The reaction mixture was shaken using an orbital shaker at 0° C. for 30 minutes then at room temperature for 18 hours. EtOAc was added to the mixture and the organic solution was washed with 1M HCl (2×1 mL), brine (1 mL) NaHCO$_3$ (2×1 mL), and brine (1 mL). The organic layer was passed through a silica gel cartridge containing a top layer of anhydrous MgSO$_4$ and moistened with hexane. The product amide was eluted with hexane (1×1 mL), hexane-EtOAc 2:1 (3×1 mL), hexane-EtOAc 1:1 (2×2 mL), and hexane-EtOAc 1:2 (1×2 mL). The fraction(s) containing pure product was identified by TLC (EtOAc-hexane 1:1 and EtOAc-hexane 1:2 in the case of 5-fluoro-3-phenylindole-2-carboxylic acid amide derivatives). The compounds were characterized and their relative purity was estimated using $^1$H NMR.

c. Method C

A mixture of an amine (see Table 1 below for amines) (0.1 mmol), an acid (5-fluoroindole-2-carboxylic acid or 5-fluoro-3-phenylindole-2-carboxylic acid) (0.1 mmol as 0.1 mL of 1M solution in THF), and DIEA (0.05 mL, 0.3 mmol) in 0.4 mL of CH$_2$Cl$_2$-THF (3:1) was cooled to 0° C. PyBrOP (0.1 mmol) was added. The reaction mixture was shaken using an orbital shaker at 0° C. for 30 minutes then at room temperature for 48 hours (0.1 mL THF and 0.2 mL CH$_2$Cl$_2$ were added after 24 hours). EtOAc was added to the mixture and the organic solution was washed with 1M HCl (2×1 mL), brine (1 mL) NaHCO$_3$ (2×1 mL), and brine (1 mL). The organic layer was passed through a silica gel cartridge containing a top layer of anhydrous MgSO$_4$ and moistened with hexane. The product amide was eluted with hexane (1×1 mL), hexane-EtOAc 2:1 (3×1 mL), hexane-EtOAc 1:1 (2×2 mL), and hexane-EtOAc 1:2 (1×2 mL). The fraction(s) containing pure product was identified by TLC (EtOAc-hexane 1:1 and EtOAc-hexane 1:2 in the case of 5-fluoro-3-phenylindole-2- carboxylic acid amide derivatives). The compounds were characterized by $^1$H NMR.

d. Method D

Preparation of 5-fluoroindole-2-carboxylic acid chloride 5-fluoroindole-2-carboxylic acid (537 mg, 3 mmol) was dissolved in DME (8 mL). 0.6 mL triethylamine was added and the mixture cooled to 0° C. Thionyl chloride (0.44 mL, 6 mmol) mixed with 4 mL DME was added cautiously using addition funnel over 10 minutes while stirring. The mixture was left to stir for 30 minutes. The formed precipitate was filtered off, and the solvent was evaporated under reduced pressure to give yellow solid of the acid chloride.

e. Representative Examples of Amide Coupling Methods

Synthesis of Compound 1z

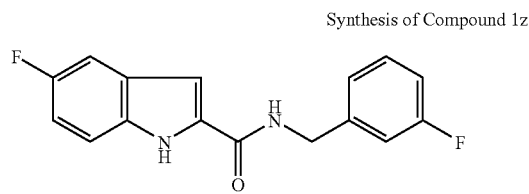

To a mixture of 3-fluorobenzylamine (2.03 g, 20 mmol) and 5-fluoroindole-2-carboxylic acid (3.58 g, 20 mmol) in DMF (50 mL), was added a solution of DIEA (6.98 mL, 40 mmol) in 15 mL CH$_2$Cl$_2$. The mixture was cooled to 0° C. and PyBOP (10.41 g, 20 mmol) was added portion wise. The reaction mixture was stirred at 0° C. for 30 minutes, then at room temperature for 4 hours. EtOAc (400 mL) was added to the mixture and the organic solution was washed with 2M HCl (4×200 mL), brine (200 mL), NaHCO$_3$ (4×200 mL), and brine (2×200 mL). The organic layer was dried (MgSO$_4$) and concentrated in vacuo to furnish the crude product as off-white solid. Recrystallization from MeOH and CH$_2$Cl$_2$ provided 5.36 g (93%) of 1z as white crystals: MP 239-241° C.; $^1$H NMR (DMSO-d$_6$, 500 MHz) δ 11.73 (s, 1H), 9.12 (t, 1H, J=6.1 Hz), 7.39 (complex, 3H), 7.17 (complex, 2H), 7.07 (dd, 1H, J=2.2 and 9.5 Hz), 7.07 (dd, 1H, J=2.2 and 9.0 Hz), 7.03 (ddd, 1H, J=2.4, 9.1 and 9.2 Hz), 4.52 (d, 2H, J=6.1 Hz); Anal. (C$_{16}$H$_{12}$F$_2$N$_2$O)C, 67.13; H, 4.23; N, 9.79; Found; C, 66.91; H, 4.31; N, 9.81.

Synthesis of Compound 1a

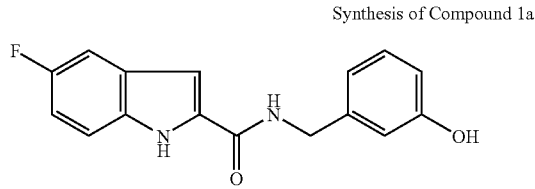

(a) Preparation of Methoxy Intermediate

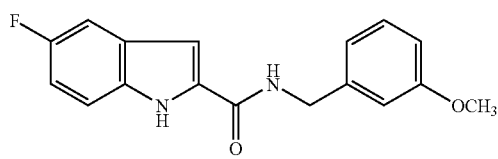

Following same procedure mentioned above for the synthesis of 1z, this compound was prepared starting from 20 mmol of amine and acid. Purification with flash column chromatography afforded 5.43 g (91%) of the methoxy intermediate as off-white crystalline solid: MP 192° C.

(b) Demethylation

A mixture of the methoxy intermediate (5 g, 16.7 mmol) and CH$_2$Cl$_2$ (80 mL) was placed in a multi neck flask equipped with a dropping funnel and a thermometer. The flask was cooled to 0° C. in an ice/salt bath. A solution of BBr$_3$ in CH$_2$Cl$_2$ (80 mL) was added dropwise while keeping the temperature less than 5° C. The mixture was stirred at room temperature for 3 hours. After addition of ice and 3M HCl (200 mL), the mixture was left to stir overnight. The precipitated solid product was collected by filtration, washed with water, and dried. Crystallization from CH$_2$Cl$_2$ and MeOH furnished 4.2 g (88%) of compound 1a: MP 213° C.; $^1$H NMR (DMSO-d$_6$, 400 MHz) δ 11.68 (br, 1H), 9.31 (br, 1H), 9.01 (t, 1H, J=6.0 Hz), 7.39 (complex, 2H), 7.14 (s, 1H), 7.09 (dd, 1H, J=8.0 and 7.7 Hz), 7.02 (ddd, 1H, J=9.2, 8.9 and 2.5 Hz), 6.72 (d, 2H, J=7.3 Hz), 6.61 (d, 1H, J=8.4 Hz), 4.41 (d, 2H, J=5.9 Hz), HRMS (EI): Required M$^+$ for C$_{16}$H$_{13}$FN$_2$O$_2$, 284.0956; Found, 284.0960; Anal. (C$_{16}$H$_{13}$FN$_2$O$_2$) C, 67.60; H, 4.61; F, N, 9.85; Found C, 67.50; H, 4.65; F, N, 9.76.

f. Other Representative Compounds Obtained and Relative Purity Data

The following are examples of compounds obtained using the above methods and their relative purity data. Table 1, below, lists all compounds obtained.

Compound 1bb

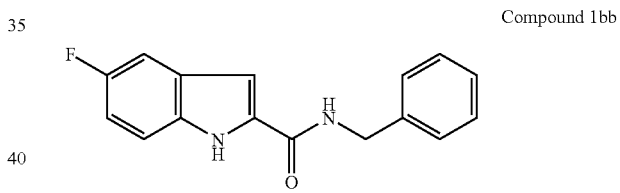

$^1$H NMR (acetone-d$_6$, 400 MHz) δ 10.85 (br, 1H), 8.29 (br, 1H), 7.53 (dd, 1H, J=9.9 and 4.6 Hz), 7.36 (d, 1H, J=7.4), 7.30 (complex, 3H), 7.22 (dd, 1H, J=7.3 and 7.0 Hz), 7.12 (s, 1H) 7.02 (ddd, 1H, J=2.6 and 9.2 and 9.1), 4.60 (d, 2H, J=6.3 Hz).

Compound 1cc

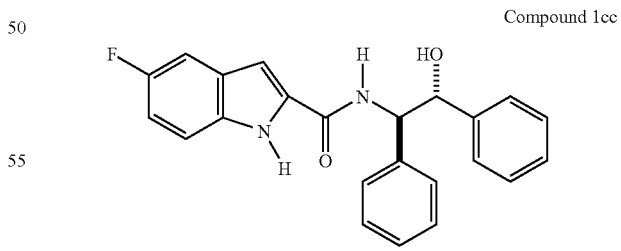

$^1$H NMR (Acetone-d$_6$, 500 MHz) δ 10.74 (br, 2H) 8.01 (d, br, 1H, J=9.0 Hz), 7.45 (dd, 1H, J=9.0 and 4.6 Hz), 7.37 (d, 2H, J=7.4 Hz), 7.34 (d, 2H, J=7.4 Hz), 7.28 (dd, 1H, J=9.5 and 2.5 Hz), 7.24 to 7.10 (complex. m, 7H), 6.99 (ddd, 1H, J=9.3, 9.2 and 2.6 Hz), 5.40 (dd, 1H, J=9.0 and 6.4 Hz), 5.20 (dd, 1H, J=6.2 and 4.6 Hz), 4.71 (d, 1H, J=4.6 Hz); LRMS (EI), m/z 356.1 (M$^+$-H$_2$O).

Compound 1dd

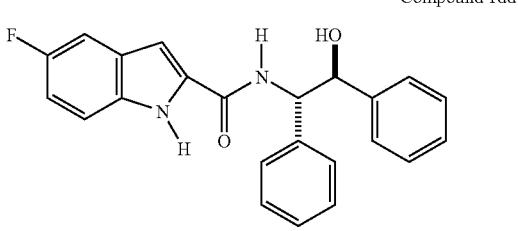

¹H NMR (Acetone-d₆, 500 MHz) δ 10.80 (br, 2H) 8.04 (d, br, 1H, J=8.7 Hz), 7.43 (dd, 1H, J=9.0 and 4.8 Hz), 7.38 (dd, 2H, J=8.0 and 1.4 Hz), 7.34 (dd, 2H, J=8.0 and 1.4 Hz), 7.28 (dd, 1H, J=9.6 and 2.4 Hz), 7.25 to 7.11 (complex. m, 7H), 6.98 (ddd, 1H, J=9.2, 9.1 and 2.5 Hz), 5.41 (dd, 1H, J=8.8d 6.6 Hz), 5.21 (dd, 1H, J=6.2 and 4.8 Hz), 4.71 (d, 1H, J=4.6 Hz).

Compound 1bbb

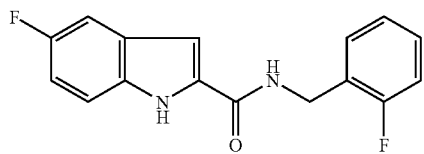

¹H NMR (acetone-d₆, 500 MHz) δ 10.89 (br, 1H), 8.31 (br, 1H), 7.54 (dd, 1H, J=9.1 and 4.6 Hz), 7.45 (dd, 1H, J=7.7 and 7.7 Hz), 7.29 (complex, 2H), 7.17-7.08 (complex, 3H), 7.03 (ddd, 1H, J=9.2, 9.1 and 2.6 Hz), 4.66 (d, 2H, J=5.8 Hz).

Compound 1yyy

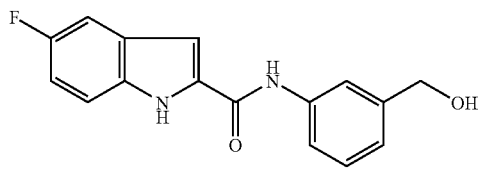

¹H NMR (Acetone-d₆, 500 MHz) δ 10.99 (br, 1H), 9.57 (br, 1H), 7.80 (s, 1H), 7.76 (d, 1H, J=8.3 MHz), 7.57 (dd, 1H, J=9.0 and 4.4 Hz), 7.35 (dd, 1H, 9.2 and 2.4 Hz), 3.34 (s, 1H), 7.29 (dd, 1H, J=7.7 and 7.8 Hz), 7.09 (d, 1H, J=8.8 Hz), 7.06 (ddd, 1H, J=9.2, 8.9 and 2.4 Hz), 4.63 (d, 2H, J=5.8 Hz), 4.24 (t, 1H, J=5.8 Hz); LRMS (EI) m/z 284.1 (74%, M⁺).

Compound 1ccc

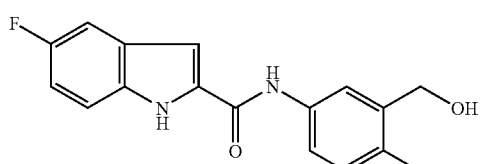

¹H NMR (acetone-d₆, 500 MHz) δ 10.96 (br, 1H), 9.49 (br, 1H), 7.79 (complex, 2H), 7.56 (dd, 1H, J=8.9 and 4.5 Hz), 7.34 (complex, 2H), 7.05 (ddd, 1H, J=9.2, 9.1 and 2.4 Hz), 6.92 (d, 1H, J=8.6 Hz), 4.65 (d, 1H, J=7.0 Hz), 4.06 (t, 1H, J=5.8), 3.81 (s, 1H); LRMS (EI) m/z 314.12 (51%, M⁺).

Compound 1oooo

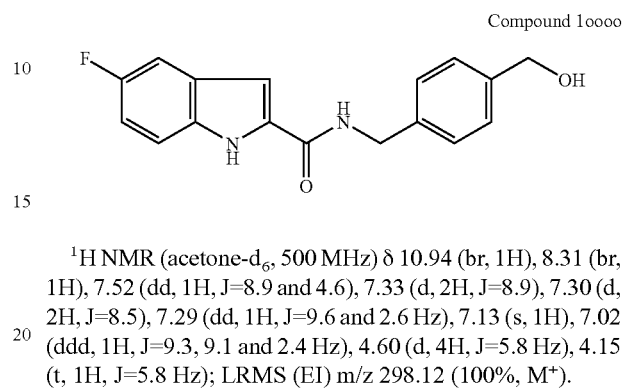

¹H NMR (acetone-d₆, 500 MHz) δ 10.94 (br, 1H), 8.31 (br, 1H), 7.52 (dd, 1H, J=8.9 and 4.6), 7.33 (d, 2H, J=8.9), 7.30 (d, 2H, J=8.5), 7.29 (dd, 1H, J=9.6 and 2.6 Hz), 7.13 (s, 1H), 7.02 (ddd, 1H, J=9.3, 9.1 and 2.4 Hz), 4.60 (d, 4H, J=5.8 Hz), 4.15 (t, 1H, J=5.8 Hz); LRMS (EI) m/z 298.12 (100%, M⁺).

Compound 2f

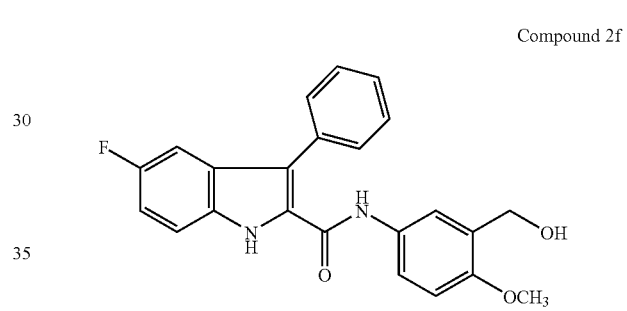

¹H NMR (acetone-d₆, 500 MHz) δ 11.12 (br, 1H), 8.07 (br, 1H), 7.66-77.60 (m, complex, 5H), 7.52 (m, 1H), 7.36 (d, 1H, J=2.2 Hz), 7.30 (dd, 1H, J=8.7 and 2.6), 7.15-7.09 (m, complex, 2H), 6.84 (d, 1H, J=8.8 Hz), 4.56 (d, 2H, J=6.1 Hz), 4.04 (t, 1 h, J=5.8 Hz), 3.77 (s, 3H).

Compound 2g

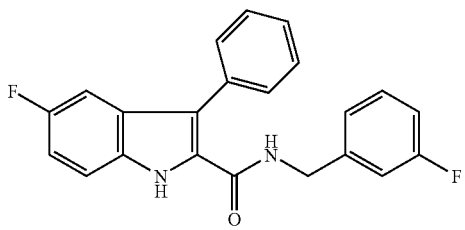

¹H NMR (Acetone-d₆, 500 MHz) δ 11.02 (br, 1H), 7.59 (dd, 1H, J=9.7 and 4.6 Hz), 7.53 (d, 1H, J=9.8 Hz), 7.47 (dd, 2H, J=7.9 and 7.4 Hz), 7.40 (m, 1H), 7.31 (dd, 1H. J=7.0 and 6.5 Hz), 7.08 (complex, 2H), 7.03 (d, 1H, J=7.7 Hz), 6.99 (complex, 2H), 6.91 (br, 1H), 4.48 (d, 2H, J=5.8 Hz); LRMS (EI) m/z 362.14 (85%, M⁺).

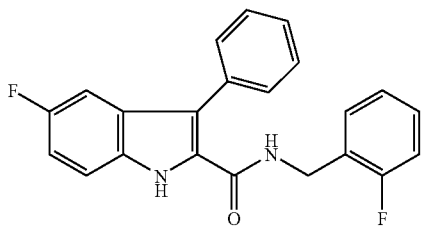

Compound 2s $^1$H NMR (Acetone-$d_6$, 500 MHz) δ 11.03 (br, 1H), 7.57-7.45 (complex, 4H), 7.544 (m, 1H), 7.31-7.24 (complex, 2H), 7.13-7.055 (complex, 4H), 6.76 (br, 1H), 4.50 (d, 2H, J=5.2 Hz); LRMS (EI) m/z 362.1 (95%, M$^+$).

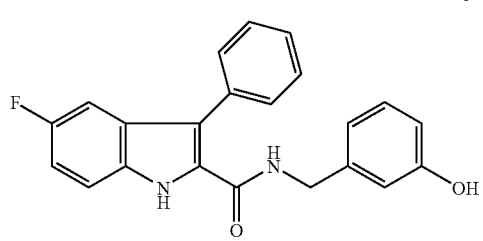

Compound 3q $^1$H NMR (Acetone-$d_6$, 500 MHz) δ 10.99 (br, 1H), 8.26 (s, 1H), 7.58 (dd, 1H, J=9.5 and 4.6 Hz), 7.51 (dd, 2H, J=8.2 and 1.4 Hz), 7.46 (dd, 2H, J=7.7 and 7.3 Hz), 7.38 (m, 1H), 7.10-7.05 (complex, 3H), 6.72 (br, 1H), 6.67 (complex, 2H), 6.62 (d, 1H, J=7.6 Hz), 4.38 (d, 2H, J=6.2 Hz); LRMS (EI) m/z 360.12 (100%, M$^+$).

2. General Procedure for Oxidation of Benzyl Alcohol Amide Derivatives to Benzaldehyde: Preparation Of Compounds 3b, 3d, 3e, 3f, 3g, and 3h The starting benzyl alcohol amide derivative was dissolved in a 1:1 mixture of $CH_2Cl_2$ and THF (5 ml/mmol), pyridinium chlorochromate (2 molar equivalent) was added, and the mixture was stirred at room temperature for 3.5 hours. EtOAc and water were added. The brown solid was removed by filtration. The organic phase was washed several times with $NaHCO_3$, brine, dried, and concentrated. Product aldehyde was purified by crystallization and confirmed by $^1$H NMR (disappearance of the methylene of benzyl alcohol and appearance of aldehyde peak).

The following table sets forth the structures made by the above methods:

TABLE 1

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1a | 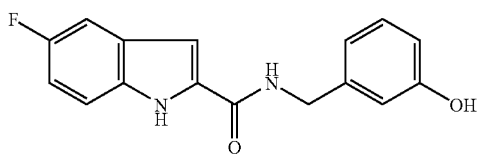 | 284.29 | See Example 1 |
| 1b | 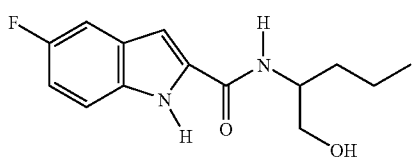 | 264.3 | Amide Coupling Method A |
| 1c | 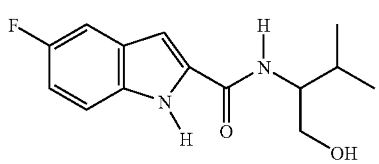 | 264.3 | Amide Coupling Method A |
| 1d | 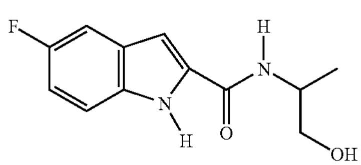 | 236.24 | Amide Coupling Method A |

TABLE 1-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 1e | 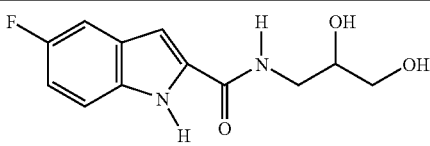 | 252.24 | Amide Coupling Method A |
| 1f | 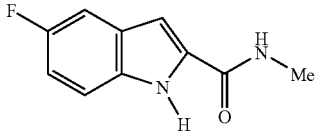 | 192.19 | Amide Coupling Method A |
| 1g | 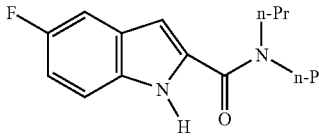 | 262.32 | Amide Coupling Method A |
| 1h | 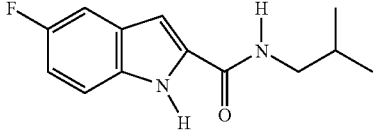 | 234.27 | Amide Coupling Method A |
| 1i | 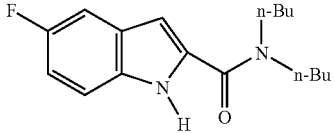 | 290.38 | Amide Coupling Method A |
| 1j | 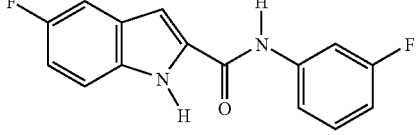 | 272.25 | Amide Coupling Method A |
| 1k | 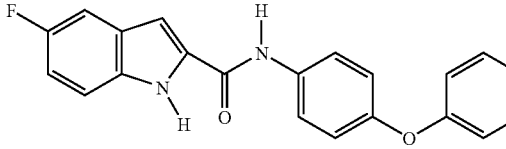 | 346.35 | Amide Coupling Method A |
| 1l | 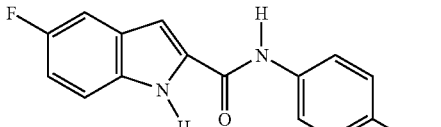 | 284.29 | Amide Coupling Method A |
| 1m | 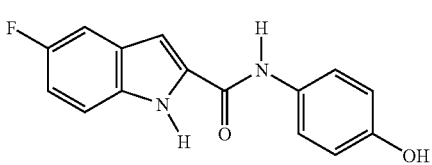 | 270.26 | Amide Coupling Method A |

TABLE 1-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1n | 5-fluoro-N-(2-hydroxyphenyl)-1H-indole-2-carboxamide | 270.26 | Amide Coupling Method A |
| 1o | 5-fluoro-N-(3,5-dimethoxyphenyl)-1H-indole-2-carboxamide | 314.31 | Amide Coupling Method A |
| 1p | 5-fluoro-N-phenyl-1H-indole-2-carboxamide | 254.26 | Amide Coupling Method A |
| 1q | 5-fluoro-N-(naphthalen-2-yl)-1H-indole-2-carboxamide | 304.32 | Amide Coupling Method A |
| 1r | 5-fluoro-N-(3,5-dihydroxyphenyl)-1H-indole-2-carboxamide | 286.26 | Amide Coupling Method A |
| 1s | 5-fluoro-N-(2-(trifluoromethyl)phenyl)-1H-indole-2-carboxamide | 322.26 | Amide Coupling Method A |
| 1t | 5-fluoro-N-(3,5-dimethylphenyl)-1H-indole-2-carboxamide | 282.31 | Amide Coupling Method A |
| 1u | 5-fluoro-N-(2-(1H-indol-3-yl)ethyl)-1H-indole-2-carboxamide | 321.35 | Amide Coupling Method A |

TABLE 1-continued
LIBRARY OF 5-FLUOROINDOLE-2-CARBAXAMIDE COMPOUNDS AND METHOD OF PREPARATION
| Cmpd Code | Structure | M. Wt. | Method of Preparation |
|---|---|---|---|
| 1v | 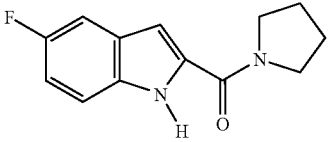 | 232.25 | Amide Coupling Method A |
| 1w | 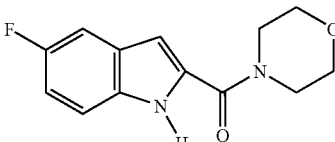 | 248.25 | Amide Coupling Method A |
| 1x | 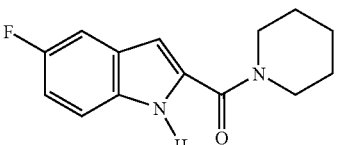 | 246.28 | Amide Coupling Method A |
| 1y | 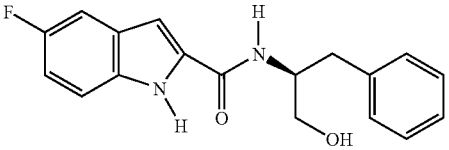 | 312.34 | Amide Coupling Method A |
| 1z | 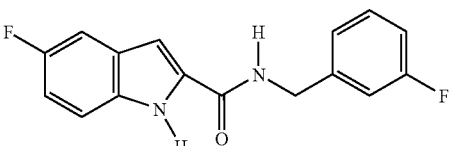 | 286.28 | Amide Coupling Method A |
| 1aa | 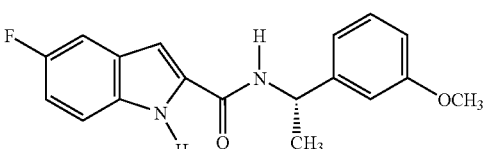 | 312.34 | Amide Coupling Method A |
| 1bb | 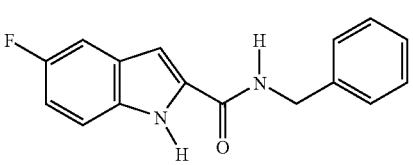 | 268.29 | Amide Coupling Method A |
| 1cc | 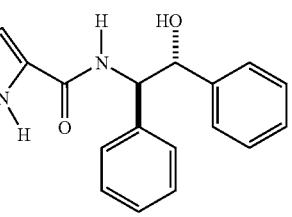 | 374.41 | Amide Coupling Method A |

TABLE 1-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1dd | 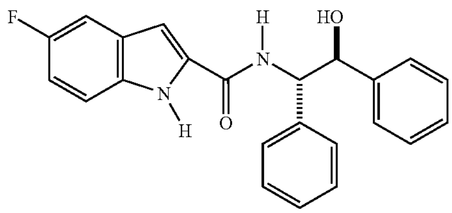 | 374.41 | Amide Coupling Method A |
| 1ee | 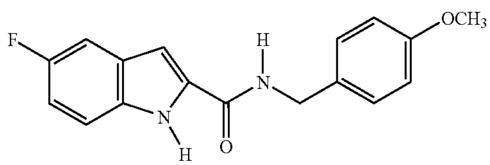 | 298.31 | Amide Coupling Method A |
| 1ff | 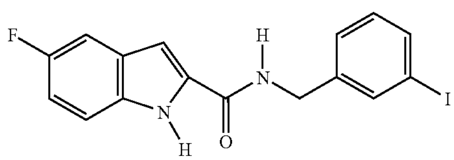 | 394.18 | Amide Coupling Method A |
| 1gg | 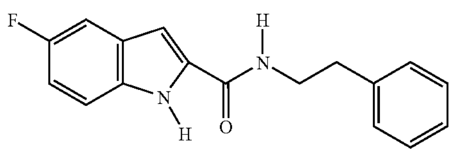 | 282.31 | Amide Coupling Method A |
| 1hh | 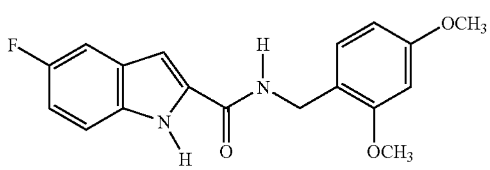 | 328.34 | Amide Coupling Method A |
| 1ii | 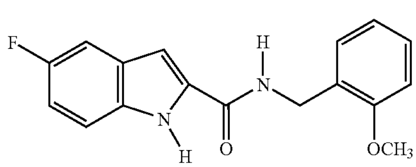 | 298.31 | Amide Coupling Method A |
| 1jj | 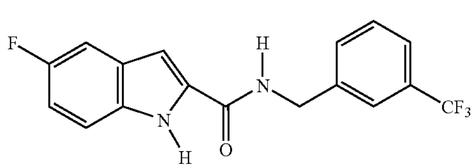 | 336.28 | Amide Coupling Method A |
| 1kk | 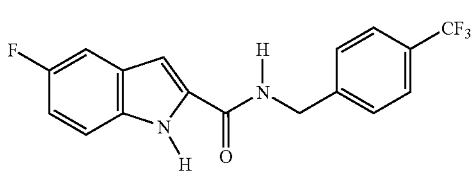 | 336.28 | Amide Coupling Method A |

TABLE 1-continued
LIBRARY OF 5-FLUOROINDOLE-2-CARBAXAMIDE
COMPOUNDS AND METHOD OF PREPARATION
| Cmpd Code | Structure | M. Wt. | Method of Preparation |
|---|---|---|---|
| 1ll | 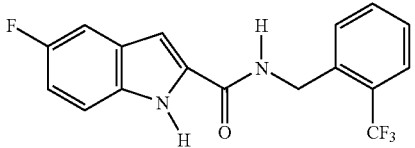 | 336.28 | Amide Coupling Method A |
| 1mm | 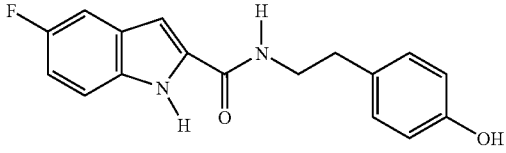 | 298.31 | Amide Coupling Method A |
| 1nn | 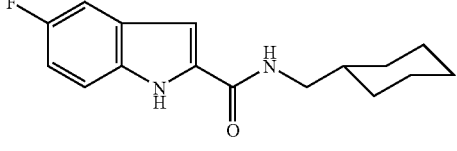 | 274.33 | Amide Coupling Method A |
| 1oo | 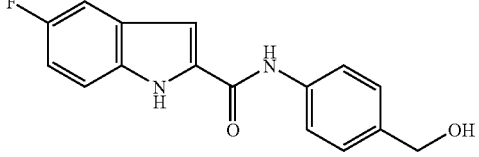 | 284.29 | Amide Coupling Method A |
| 1pp | 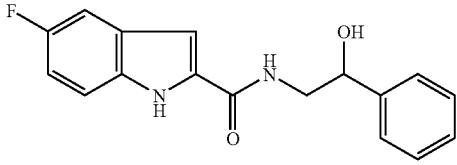 | 298.31 | Amide Coupling Method A |
| 1qq | 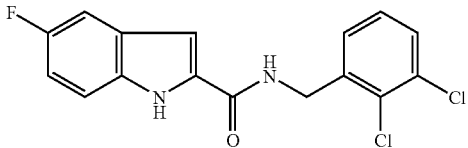 | 337.18 | Amide Coupling Method A |
| 1rr | 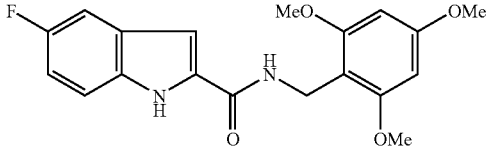 | 358.36 | Amide Coupling Method A |
| 1ss | 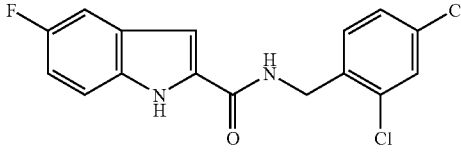 | 337.18 | Amide Coupling Method A |

TABLE 1-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1tt | 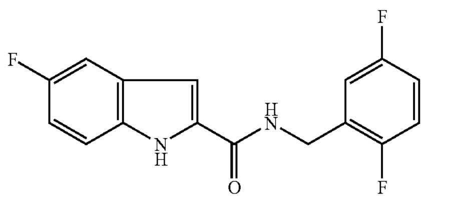 | 304.27 | Amide Coupling Method A |
| 1uu | 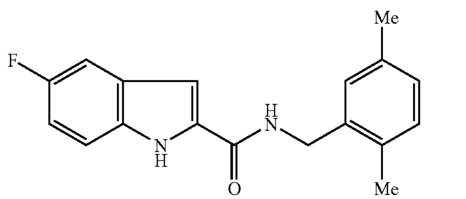 | 296.34 | Amide Coupling Method A |
| 1vv | 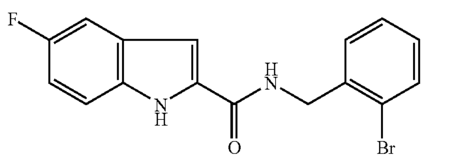 | 347.18 | Amide Coupling Method A |
| 1ww | 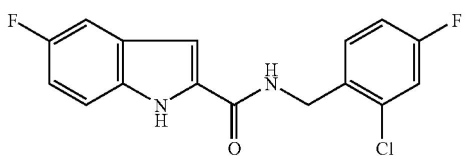 | 320.72 | Amide Coupling Method A |
| 1xx | 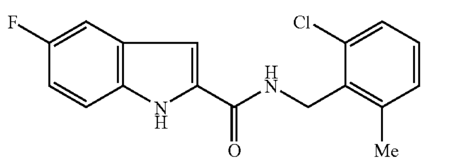 | 316.76 | Amide Coupling Method A |
| 1yy | 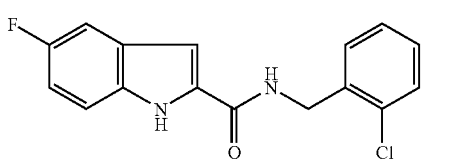 | 302.73 | Amide Coupling Method A |
| 1zz | 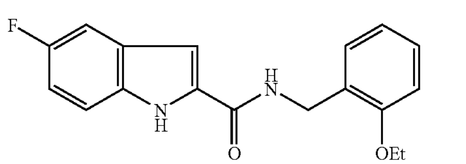 | 312.34 | Amide Coupling Method A |
| 1aaa | 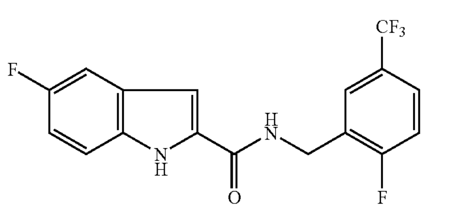 | 354.27 | Amide Coupling Method A |

TABLE 1-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1bbb | 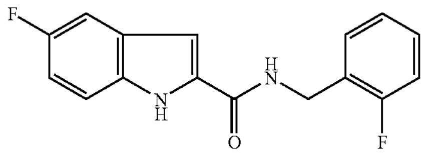 | 286.28 | Amide Coupling Method A |
| 1ccc | 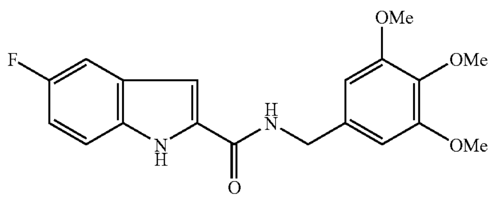 | 358.36 | Amide Coupling Method A |
| 1ddd | 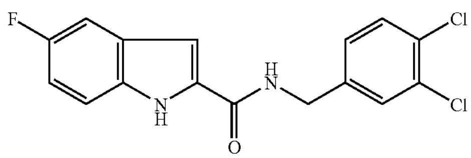 | 337.18 | Amide Coupling Method A |
| 1eee | 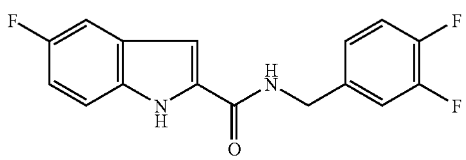 | 304.27 | Amide Coupling Method A |
| 1fff | 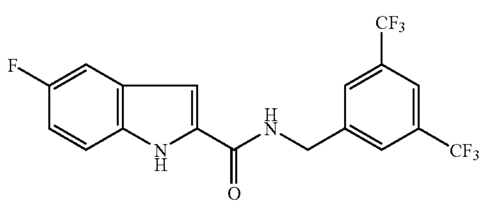 | 404.28 | Amide Coupling Method A |
| 1ggg | 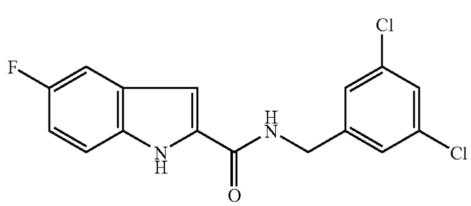 | 337.18 | Amide Coupling Method A |
| 1hhh | 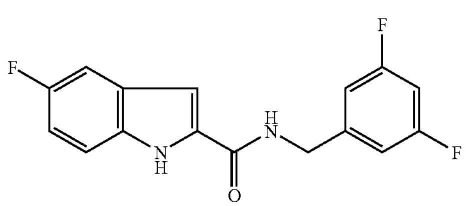 | 304.27 | Amide Coupling Method A |
| 1iii | 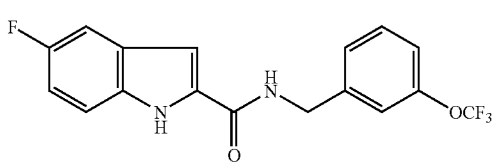 | 352.28 | Amide Coupling Method A |

TABLE 1-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 1jjj | 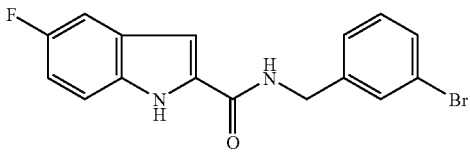 | 347.18 | Amide Coupling Method A |
| 1kkk | 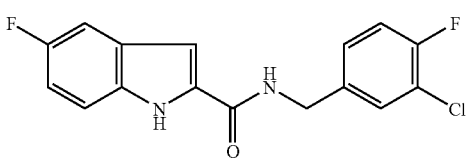 | 320.72 | Amide Coupling Method A |
| 1lll | 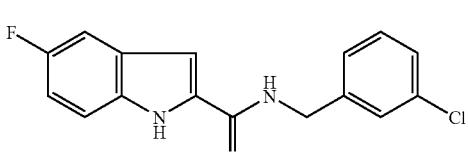 | 302.73 | Amide Coupling Method A |
| 1mmm | 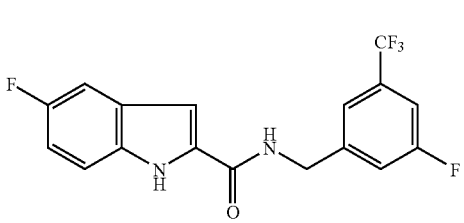 | 354.27 | Amide Coupling Method A |
| 1nnn | 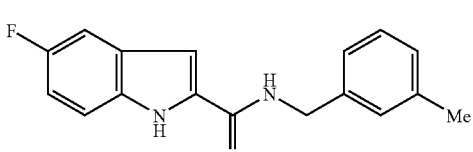 | 282.31 | Amide Coupling Method A |
| 1ooo | 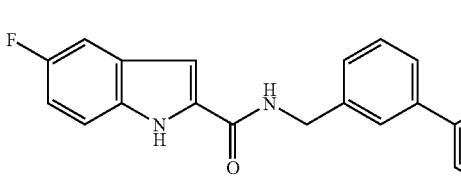 | 344.38 | Amide Coupling Method A |
| 1ppp | 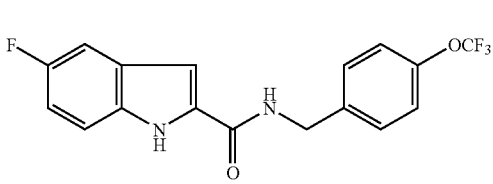 | 352.28 | Amide Coupling Method A |
| 1qqq | 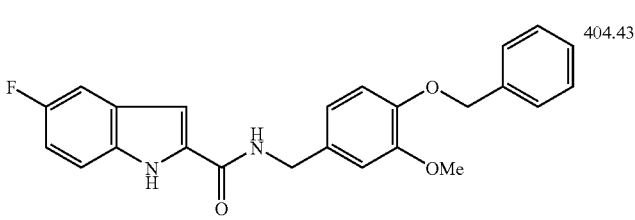 | 404.43 | Amide Coupling Method A |

TABLE 1-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 1rrr | 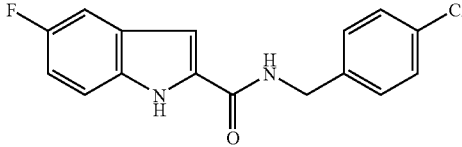 | 302.73 | Amide Coupling Method A |
| 1sss | 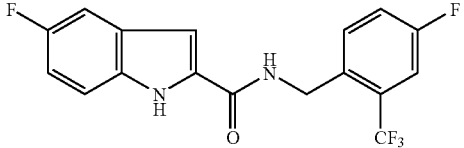 | 354.27 | Amide Coupling Method A |
| 1ttt | 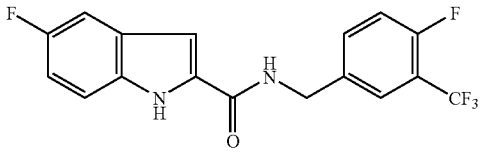 | 354.27 | Amide Coupling Method A |
| 1uuu | 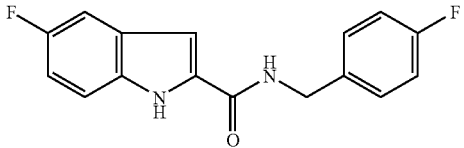 | 286.28 | Amide Coupling Method A |
| 1vvv | 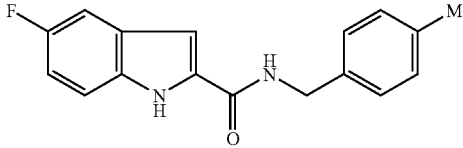 | 282.31 | Amide Coupling Method A |
| 1www | 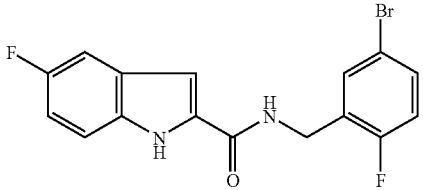 | 265.17 | Amide Coupling Method A |
| 1xxx | 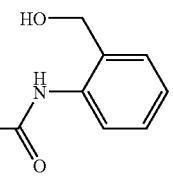 | 284.29 | Amide Coupling Method C |
| 1yyy | 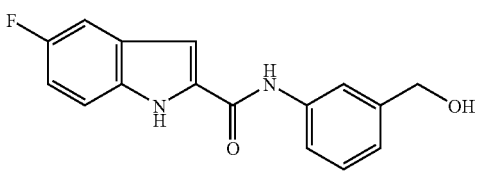 | 284.29 | Amide Coupling Method B |

TABLE 1-continued
LIBRARY OF 5-FLUOROINDOLE-2-CARBAXAMIDE
COMPOUNDS AND METHOD OF PREPARATION
| Cmpd Code | Structure | M. Wt. | Method of Preparation |
|---|---|---|---|
| 1zzz | 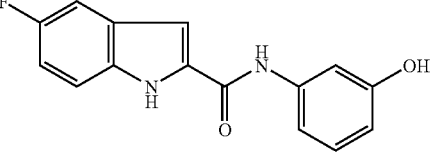 | 270.26 | Amide Coupling Method C |
| 1aaaa | 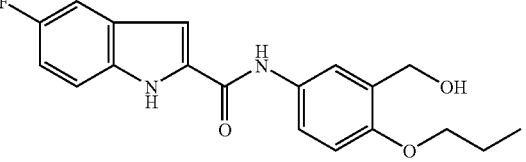 | 342.36 | Amide Coupling Method C |
| 1bbbb | 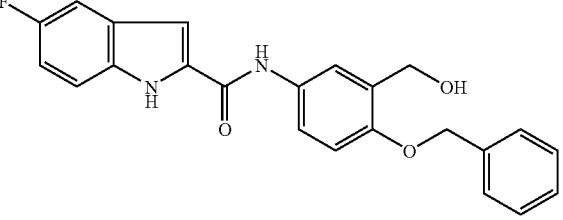 | 390.41 | Amide Coupling Method C |
| 1cccc | 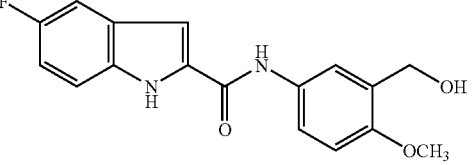 | 314.31 | Amide Coupling Method C |
| 1dddd | 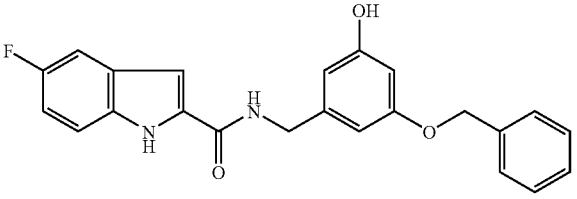 | 390.41 | Amide Coupling Method B |
| 1eeee | 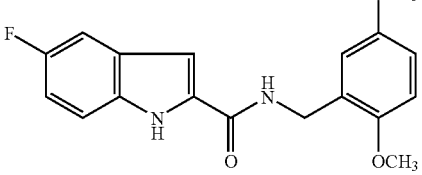 | 328.34 | Amide Coupling Method B |
| 1ffff | 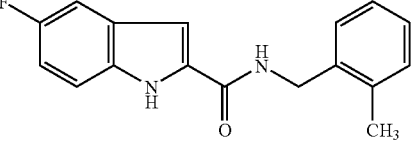 | 282.31 | Amide Coupling Method B |

TABLE 1-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 1gggg | 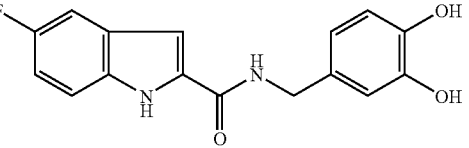 | 300.28 | Amide Coupling Method B |
| 1hhhh | 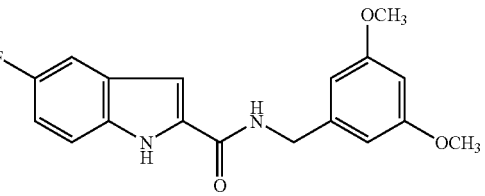 | 328.34 | Amide Coupling Method B |
| 1iiii | 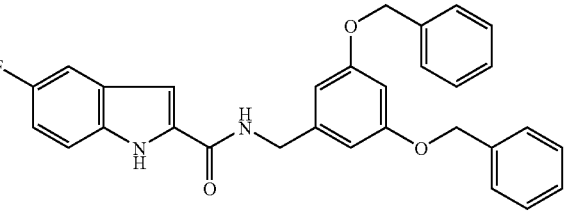 | 480.53 | Amide Coupling Method B |
| 1jjjj | 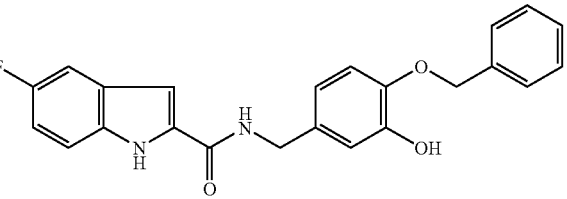 | 390.41 | Amide Coupling Method B |
| 1kkkk | 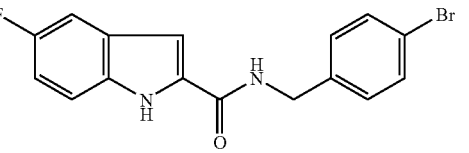 | 347.18 | Amide Coupling Method B |
| 1llll | 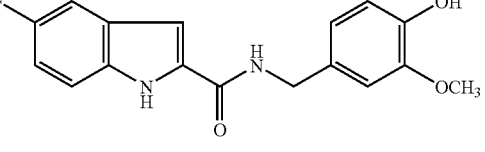 | 314.31 | Amide Coupling Method B |
| 1mmmm | 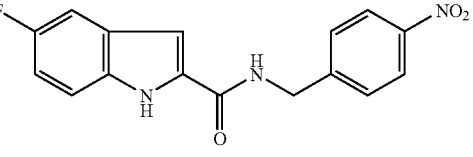 | 313.28 | Amide Coupling Method B |
| 1nnnn | 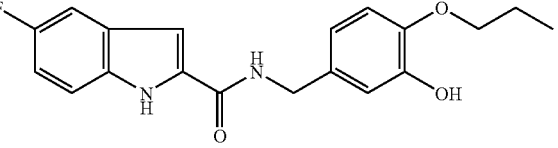 | 342.36 | Amide Coupling Method B |

TABLE 1-continued
LIBRARY OF 5-FLUOROINDOLE-2-CARBAXAMIDE COMPOUNDS AND METHOD OF PREPARATION
| Cmpd Code | Structure | M. Wt. | Method of Preparation |
|---|---|---|---|
| 1oooo | 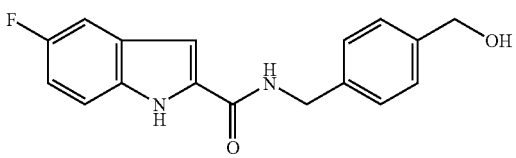 | 298.31 | Amide Coupling Method B |
| 1pppp | 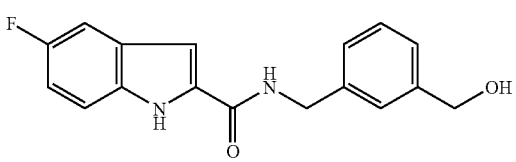 | 298.31 | Amide Coupling Method B |
| 1qqqq | 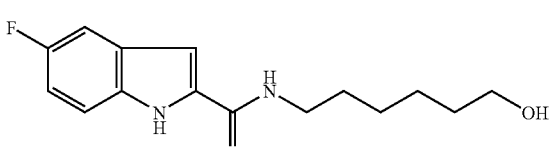 | 278.32 | Amide Coupling Method B |
| 2a | 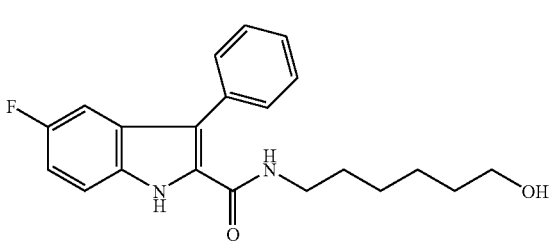 | 354.42 | Amide Coupling Method B |
| 2b | 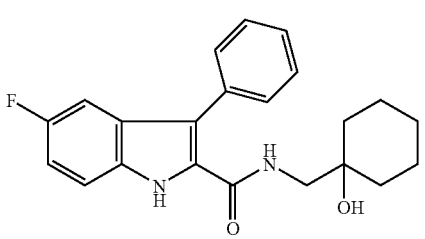 | 366.43 | Amide Coupling Method B |
| 2c | 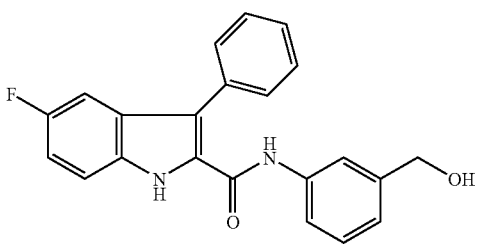 | 360.38 | Amide Coupling Method B |
| 2d | 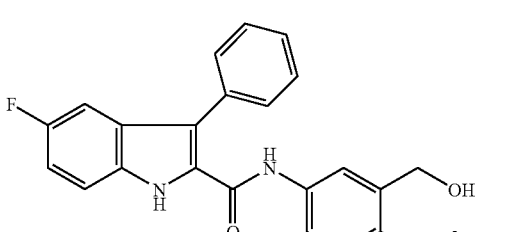 | 418.46 | Amide Coupling Method B |

TABLE 1-continued
LIBRARY OF 5-FLUOROINDOLE-2-CARBAXAMIDE
COMPOUNDS AND METHOD OF PREPARATION
| Cmpd Code | Structure | M. Wt. | Method of Preparation |
|---|---|---|---|
| 2e | 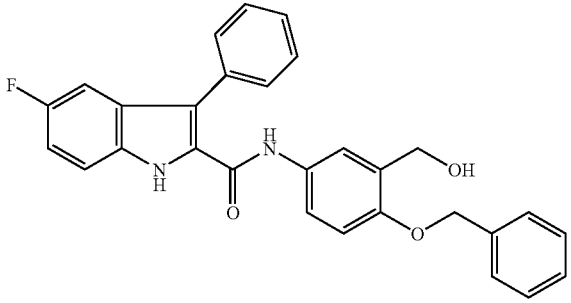 | 466.5 | Amide Coupling Method B |
| 2f | 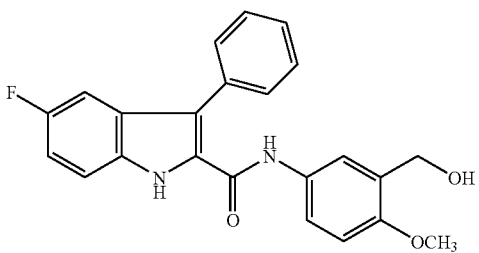 | 390.41 | Amide Coupling Method B |
| 2g | 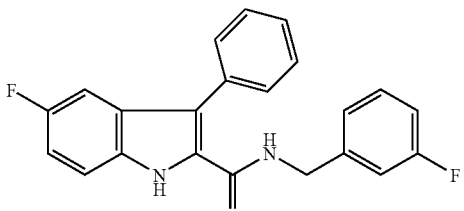 | 362.37 | Amide Coupling Method B |
| 2h | 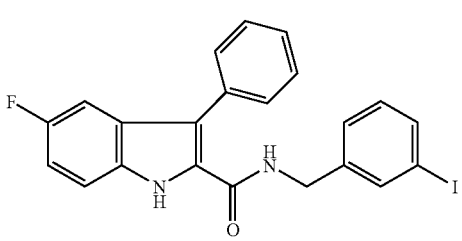 | 470.28 | Amide Coupling Method B |
| 2i | 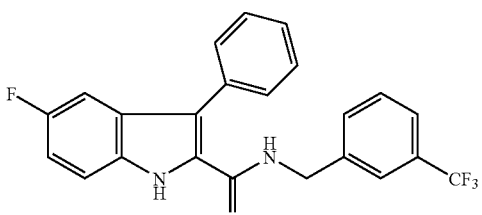 | 412.38 | Amide Coupling Method B |
| 2j | 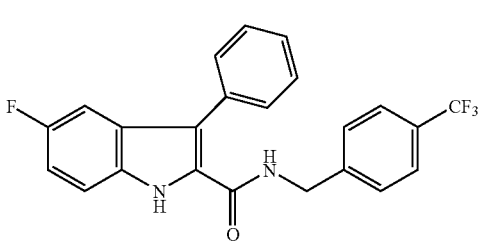 | 412.38 | Amide Coupling Method B |

TABLE 1-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 2k | 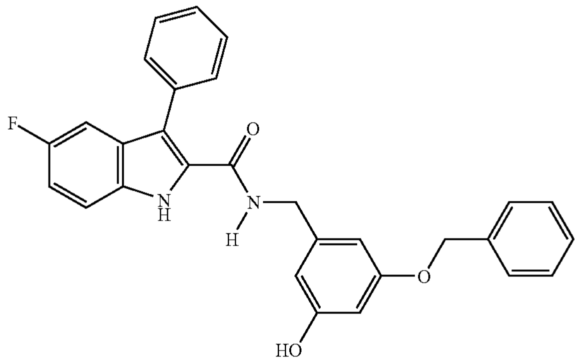 | 466.5 | Amide Coupling Method B |
| 2l | 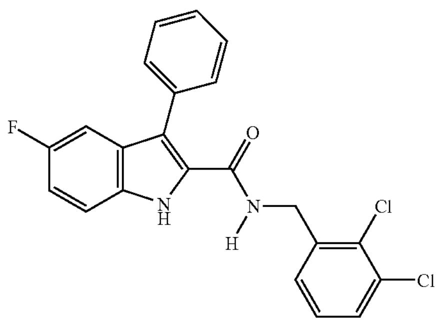 | 413.27 | Amide Coupling Method B |
| 2m | 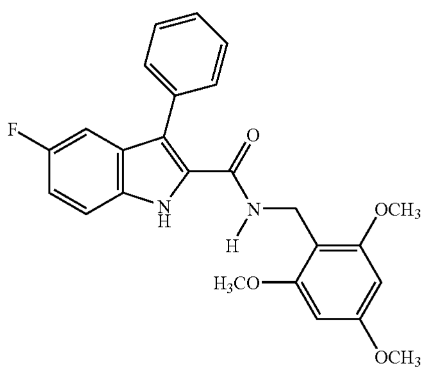 | 434.46 | Amide Coupling Method B |
| 2n | 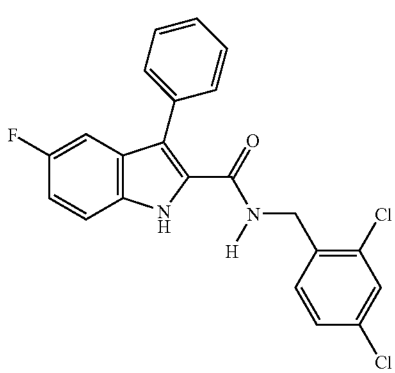 | 413.27 | Amide Coupling Method B |

TABLE 1-continued
LIBRARY OF 5-FLUOROINDOLE-2-CARBAXAMIDE
COMPOUNDS AND METHOD OF PREPARATION
| Cmpd Code | Structure | M. Wt. | Method of Preparation |
|---|---|---|---|
| 2o | 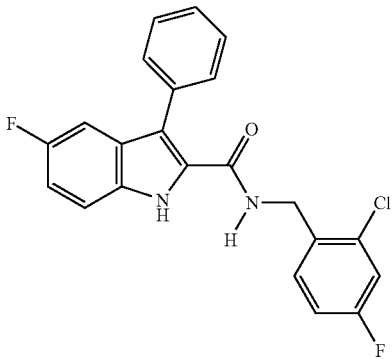 | 396.82 | Amide Coupling Method B |
| 2p | 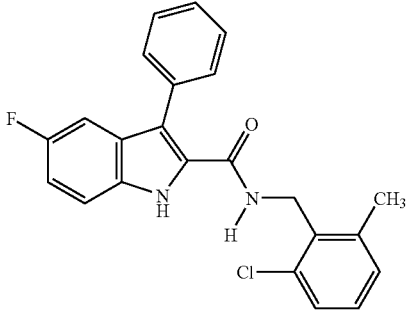 | 392.85 | Amide Coupling Method B |
| 2q | 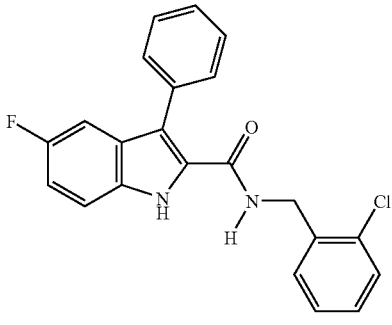 | 378.83 | Amide Coupling Method B |
| 2r | 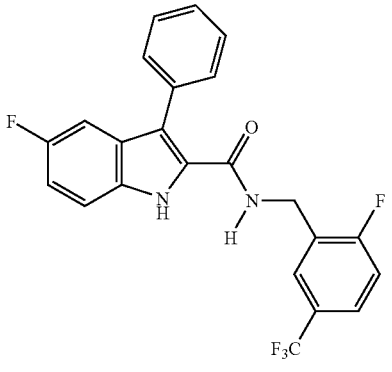 | 430.37 | Amide Coupling Method B |

TABLE 1-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 2s | 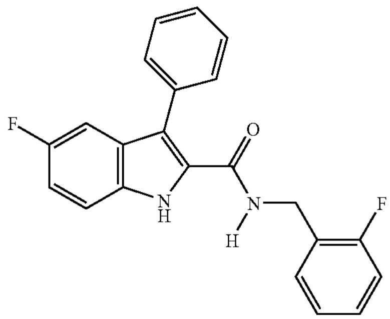 | 362.37 | Amide Coupling Method B |
| 2t | 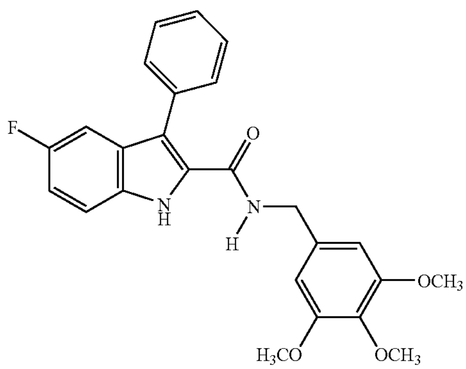 | 434.46 | Amide Coupling Method B |
| 2u | 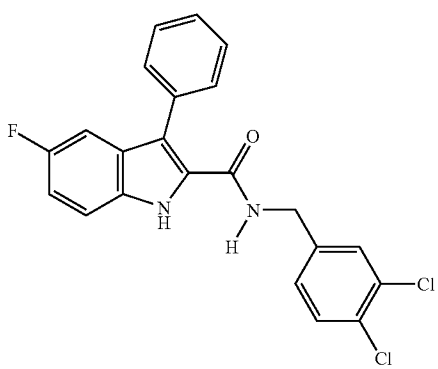 | 413.27 | Amide Coupling Method B |
| 2v | 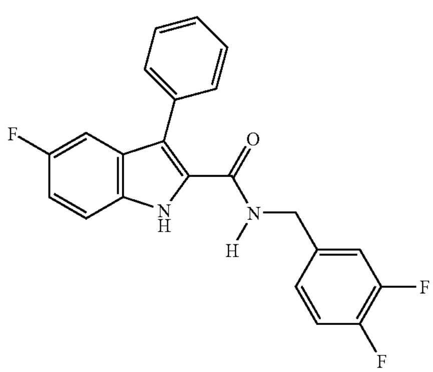 | 380.36 | Amide Coupling Method B |

TABLE 1-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 2w | 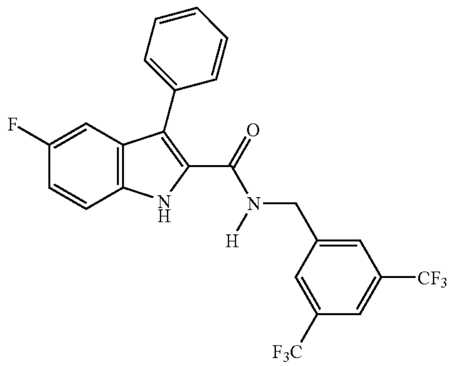 | 480.38 | Amide Coupling Method B |
| 2x | 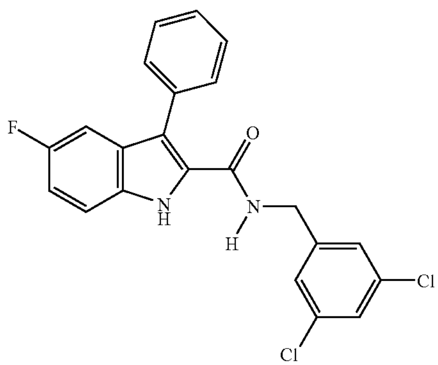 | 413.27 | Amide Coupling Method B |
| 2y | 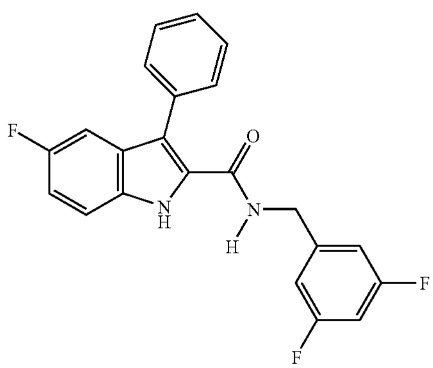 | 380.36 | Amide Coupling Method B |
| 2z | 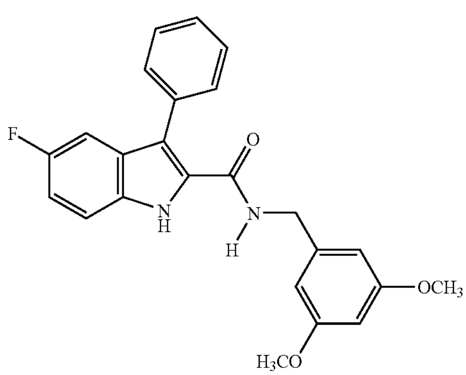 | 404.43 | Amide Coupling Method B |

TABLE 1-continued
LIBRARY OF 5-FLUOROINDOLE-2-CARBAXAMIDE
COMPOUNDS AND METHOD OF PREPARATION
| Cmpd Code | Structure | M. Wt. | Method of Preparation |
|---|---|---|---|
| 2aa | 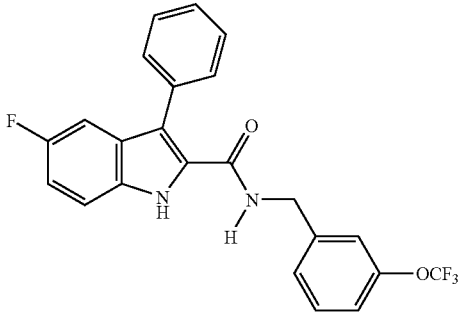 | 428.38 | Amide Coupling Method B |
| 2bb | 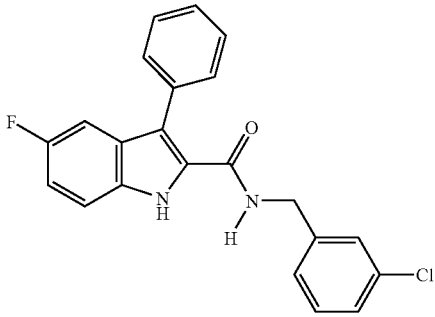 | 378.83 | Amide Coupling Method B |
| 2cc | 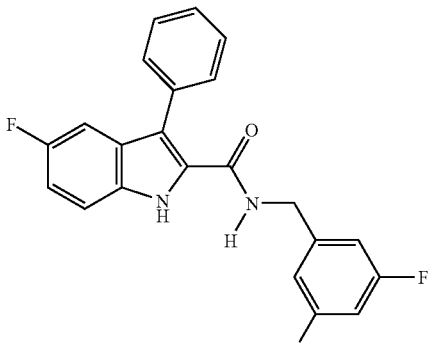 | 430.37 | Amide Coupling Method B |
| 2dd | 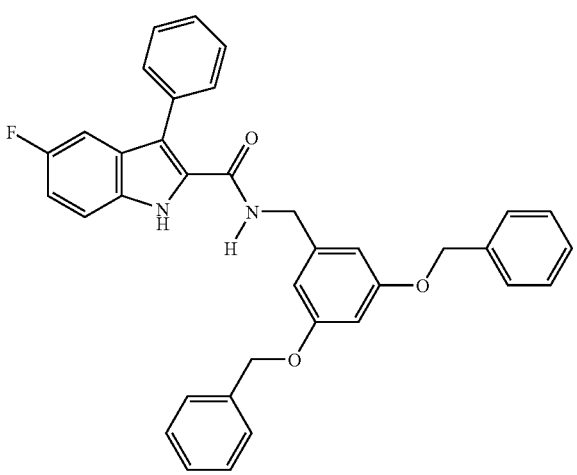 | 556.63 | Amide Coupling Method B |

TABLE 1-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 2ee | 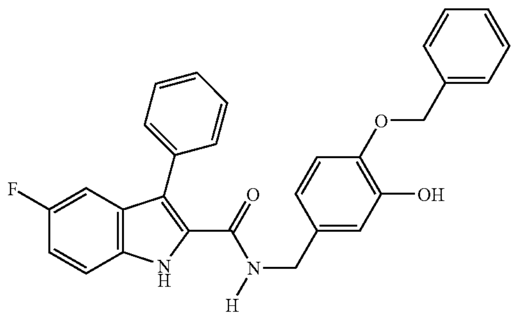 | 466.5 | Amide Coupling Method B |
| 2ff | 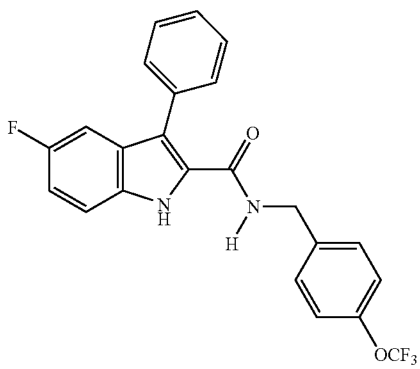 | 428.38 | Amide Coupling Method B |
| 2gg | 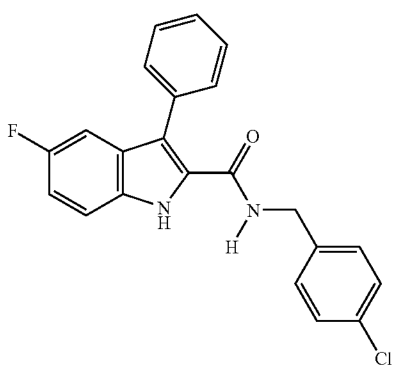 | 378.83 | Amide Coupling Method B |
| 2hh | 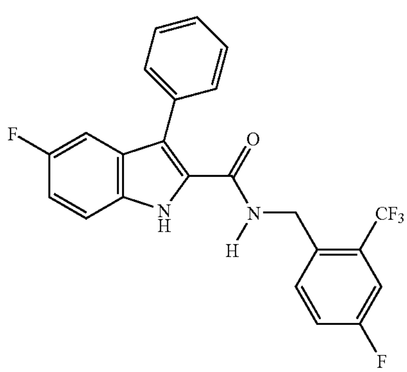 | 430.37 | Amide Coupling Method B |

TABLE 1-continued
LIBRARY OF 5-FLUOROINDOLE-2-CARBAXAMIDE
COMPOUNDS AND METHOD OF PREPARATION
| Cmpd Code | Structure | M. Wt. | Method of Preparation |
|---|---|---|---|
| 2ii | 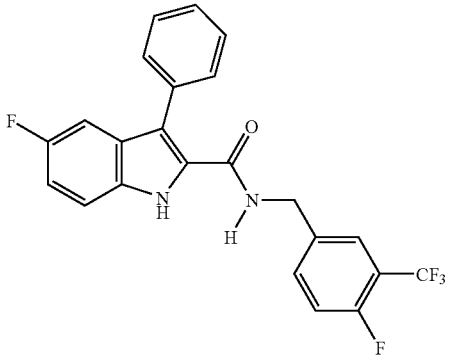 | 431.37 | Amide Coupling Method B |
| 2jj | 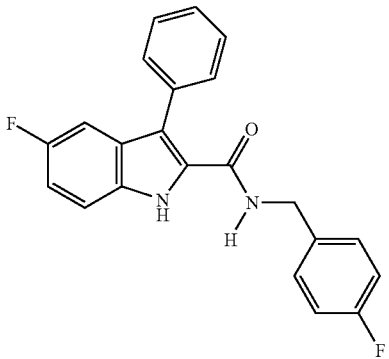 | 362.37 | Amide Coupling Method B |
| 2kk | 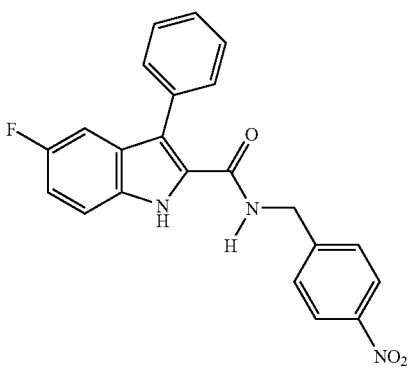 | 389.38 | Amide Coupling Method B |
| 2ll | 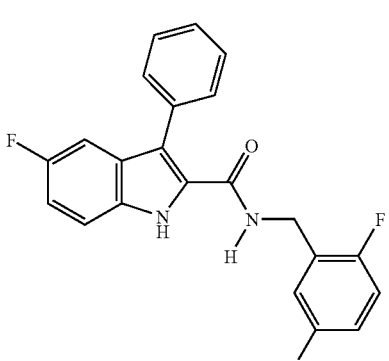 | 441.27 | Amide Coupling Method B |

…
TABLE 1-continued
LIBRARY OF 5-FLUOROINDOLE-2-CARBAXAMIDE COMPOUNDS AND METHOD OF PREPARATION
| Cmpd Code | Structure | M. Wt. | Method of Preparation |
|---|---|---|---|
| 2mm | 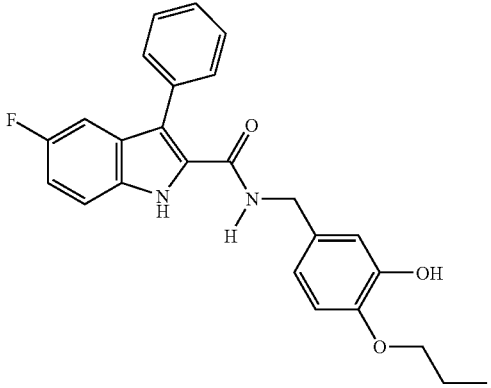 | 418.46 | Amide Coupling Method B |
| 2nn | 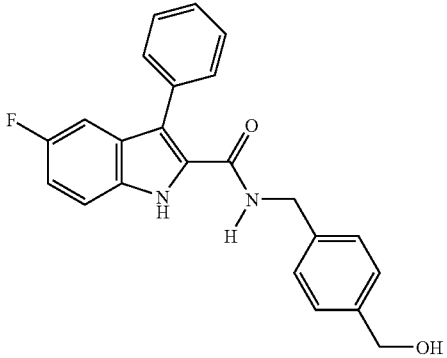 | 374.41 | Amide Coupling Method B |
| 2oo | 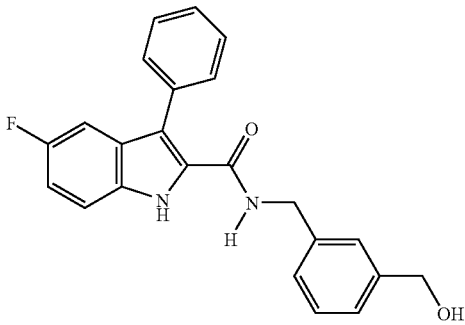 | 375.41 | Amide Coupling Method B |
| 3a | 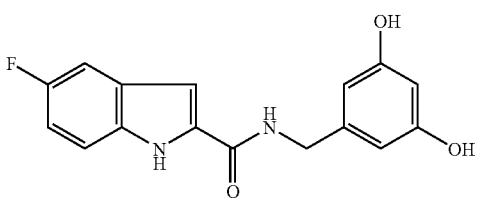 | 300.28 | Demethylation of compound 1hh using $BBr_3$ method in Example 1 |
| 3b | 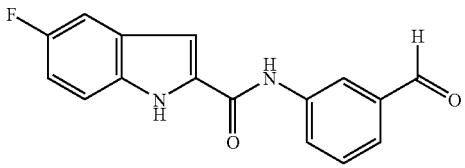 | 282.27 | Oxidation of 1yyy |

TABLE 1-continued
LIBRARY OF 5-FLUOROINDOLE-2-CARBAXAMIDE
COMPOUNDS AND METHOD OF PREPARATION
| Cmpd Code | Structure | M. Wt. | Method of Preparation |
|---|---|---|---|
| 3c | 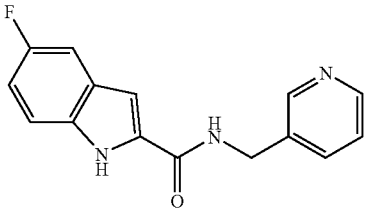 | 269.29 | Amide Coupling Method C |
| 3d | 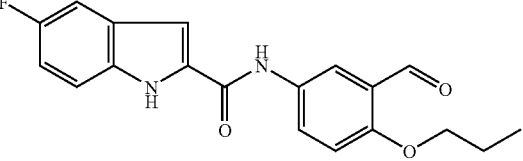 | 340.35 | Oxidation of 1aaaa |
| 3e | 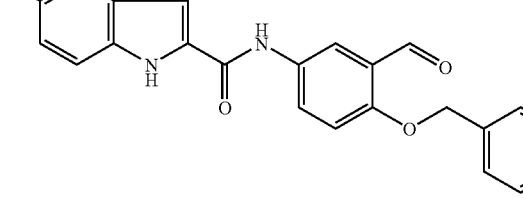 | 388.39 | Oxidation of 1bbbb |
| 3f | 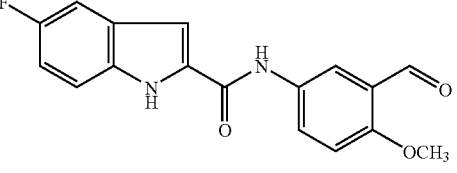 | 312.3 | Oxidation of 1cccc |
| 3g | 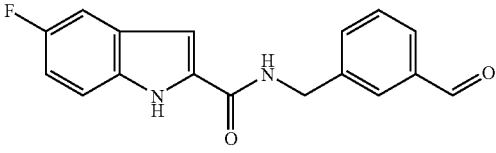 | 296.3 | Oxidation of 1pppp |
| 3h | 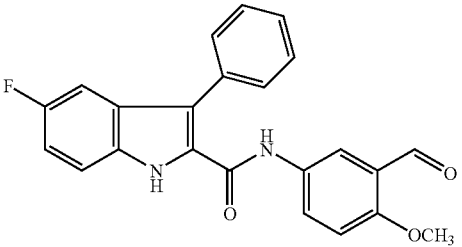 | 388.39 | Oxidation of 2f |

TABLE 1-continued
LIBRARY OF 5-FLUOROINDOLE-2-CARBAXAMIDE
COMPOUNDS AND METHOD OF PREPARATION
| Cmpd Code | Structure | M. Wt. | Method of Preparation |
|---|---|---|---|
| 3i | 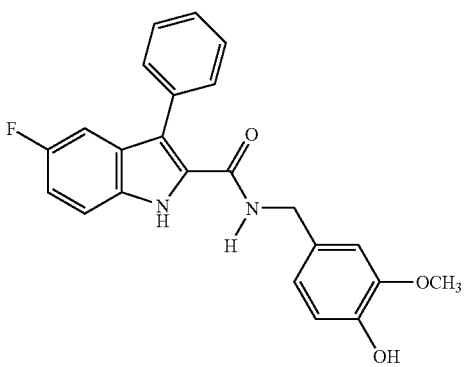 | 390.41 | Amide Coupling Method B |
| 3j | 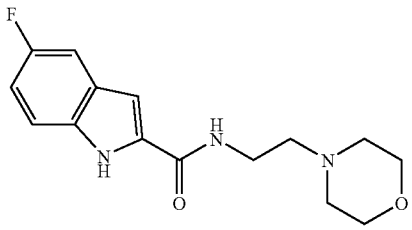 | 291.31 | Amide Coupling Method C |
| 3k | 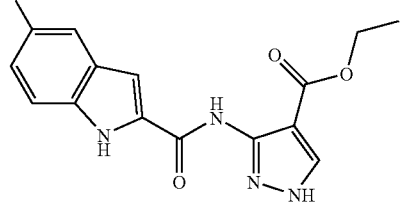 | 316.28 | Amide Coupling Method C |
| 3l | 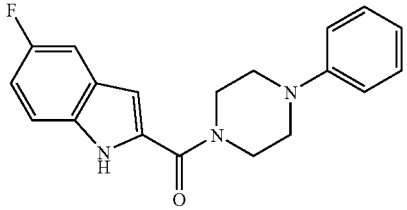 | 323.35 | Amide Coupling Method C |
| 3m | 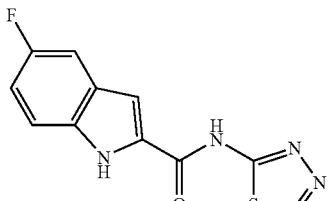 | 262.26 | Amide Coupling Method C |
| 3n | 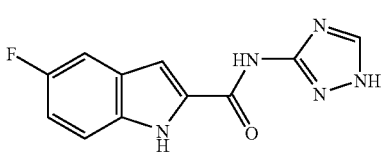 | 245.21 | Amide Coupling Method C |

TABLE 1-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 3o | 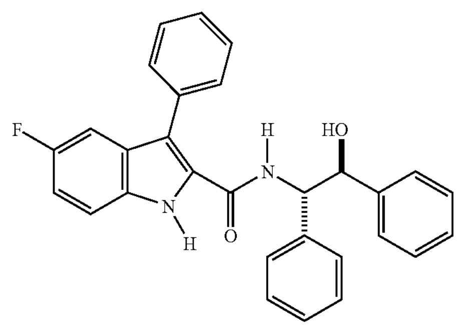 | 450.5 | Amide Coupling Method B |
| 3p | 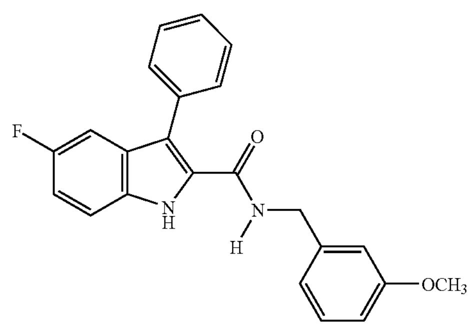 | 374.41 | Amide Coupling Method B |
| 3q | 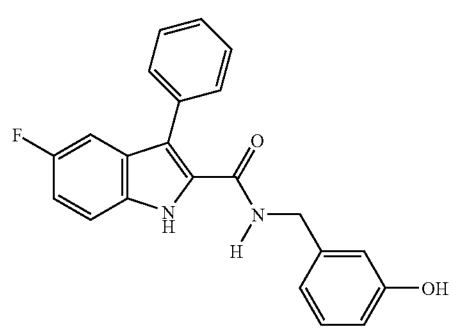 | 360.38 | See synthesis of 1a in Example 1 |
| 3r | 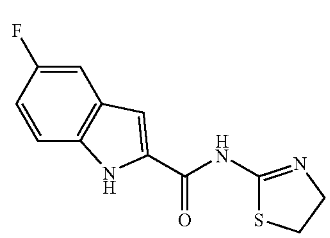 | 263.3 | Amide Coupling Method D |

TABLE 1-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 3s | [5-fluoroindole-2-carboxamide linked to 5-methylisoxazol-3-yl] | 259.24 | Amide Coupling Method D |
| 3t | [5-fluoroindole-2-carboxamide linked to pyridin-2-yl] | 255.25 | Amide Coupling Method D |

C. Inhibition of Human Cancer Cell Line H460 and Isolated Src.

Subsequent to synthesis, several of the above compounds were tested for inhibition of the growth of human lung cancer cell line H460 and inhibition of isolated Src. To test for inhibition of H460, the cells were seeded at 600 cells/well in 96 well plates in complete medium-RPMI-1640 containing 5% FCS, 5% NuSerum IV, 2 mM L-glutamine, and 10 mM HEPES. Following an overnight incubation, compounds which were solubilized in DMSO and diluted in RPMI-1640, were added to cells plates. After 72 hours, cells were fixed, stained, and total protein/well was determined. Compound concentration which inhibited growth by 50% ($IC_{50}$) was determined and is reported below. To test for inhibition of isolated Src, the compounds were tested using the assay procedure described in Lai et al., 1998, with the following assay components, final concentrations, and conditions: 50.0 mM MOPS, 4.02 mM $MgCl_2$, 6.00 mM $K_3$ citrate (used as a $Mg^{2+}$ buffer to stabilize the free $Mg^{2+}$ at 0.5 mM), 99.0 mM KCl, 10.0 mM 2-mercaptoethanol, 198 μM ADP, 10 U full length human purified recombinant $pp60^{c-src}$ (Upstate Biotechnology Inc., Lake Placid, N.Y.), 2.00 mM RR-SRC, 4.0% DMSO, pH 7.2, 37° C. These overall assay conditions have been shown to reproduce the intracellular conditions of pH, temperature, free $M^{2+}$ (0.5 mM), ionic strength, osmolality, ATP/ADP, and reduction potential. The results are in Table 2, below.

TABLE 2

INHIBITION OF THE GROWTH OF HUMAN LUNG CANCER CELL LINE H460 AND THE INHIBITION OF ISOLATED SRC

| Compound | $H460^a$ $IC_{50}$ (μM)[b] | Src at 100 μM |
|---|---|---|
| 1a | 35 ± 0.59 | $IC_{50}$ = 40 |
| 1z | 15 ± 1.6 | $NT^c$ |
| 1bb | 82 ± 3.5 | NT |
| 1dd | 33 ± 0.78 | NT |
| 1yyy | 104 ± 10 | NT |
| 1cc | 30 ± 0.66 | NT |
| 1cccc | >100 | NT |
| 1oooo | 74 ± 2.7 | NT |
| 2f | 13 ± 0.46 | NT |
| 2s | 26 ± 0.34 | NT |
| 1bbb | >100 | NT |
| 2g | 13 ± 0.56 | NT |
| 3q | 30 ± 0.34 | NT |

[a] H460 - NSCLC cells.
[b] All compounds were solubilized in DMSO and further diluted in RPMI 1640 containing 5% FCS, 5% NuSerum IV, 2 mM L-glutamine, and 20 mM HEPES.
[c] NT = not tested.

These results show that the use of a phenyl group attached to the 3 position of the indole ring can significantly improve the activity of the inhibitor.

D. Inhibition of Epidermal Growth Factor Receptor Tyrosine Kinase (EGFRTK), p56 lck, p55 fyn, and PTP-1B The compounds listed in Table 3 below were tested for inhibition of EGFRTK, a transmembrane receptor tyrosine kinase, p56 lck, a member of the Src family of non-receptor tyrosine kinases, p55 fyn, another member of the Src family of non-receptor tyrosine kinases, and protein tyrosine phosphatase 1B (PTP-1B), a phosphotyrosine phosphatase, the opposite of a kinase and a target for type II diabetes and/or obesity. The data in the table are the % inhibition of the indicated enzyme by the compound at a concentration of 10 micromolar. Blanks for a particular enzyme indicate that inhibition was not found.

TABLE 3

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| (5-F-indole-2-carboxamide, N-CH(CH2OH)(n-Pr)) | 264.3 | 1b | | | | |
| (5-F-indole-2-carboxamide, N-CH(CH2OH)(i-Pr)) | 264.3 | 1c | | | | |
| (5-F-indole-2-carboxamide, N-CH(CH2OH)Me) | 236.2 | 1d | | | | |
| (5-F-indole-2-carboxamide, N-CH2CH(OH)CH2OH) | 252.2 | 1e | | | | |
| (5-F-indole-2-carboxamide, N-Me) | 192.2 | 1f | | | | |
| (5-F-indole-2-carboxamide, N(n-Pr)2) | 262.3 | 1g | | | | 19 |
| (5-F-indole-2-carboxamide, N-isobutyl) | 234.3 | 1h | | | | |
| (5-F-indole-2-carboxamide, N(n-Bu)2) | 290.4 | 1i | | | | |
| (5-F-indole-2-carboxamide, N-(3-F-phenyl)) | 272.3 | 1j | | | | |

TABLE 3-continued
INHIBITION OF EGFRPTK, p56 lck, p55 fyn, and PTP-1B
| Structure | MW | Compound Code | PTP-1B @ 10 μm | EGFRTK @ 10 μm | p56 Lck @ 10 μm | p55 fyn @ 10 μm |
|---|---|---|---|---|---|---|
| 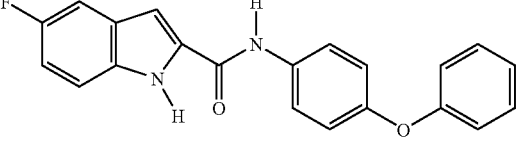 | 346.4 | 1k | | | | 13 |
| 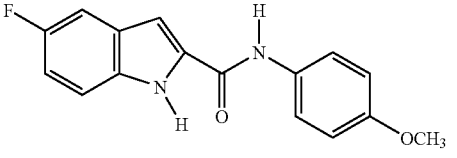 | 284.3 | 1l | | | | |
| 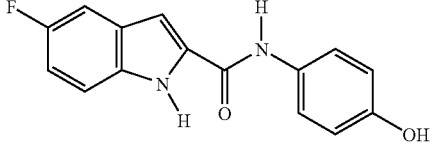 | 270.3 | 1m | | | | |
| 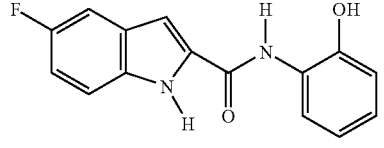 | 270.3 | 1n | | | 12 | |
| 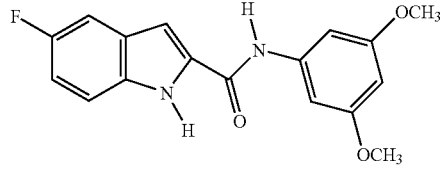 | 314.3 | 1o | | | | |
| 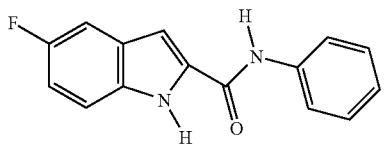 | 254.3 | 1p | | | | |
| 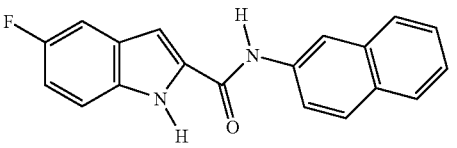 | 304.3 | 1q | | | | |
| 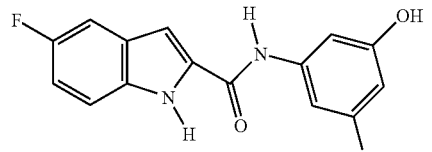 | 286.3 | 1r | | | 11 | |
| 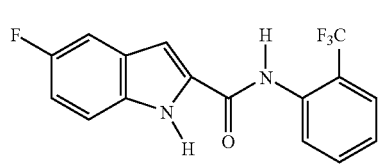 | 322.3 | 1s | | | | |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| (5-fluoro-indole-2-carboxylic acid (3,5-dimethyl-phenyl)-amide) | 282.3 | 1t | | | | 11 |
| (5-fluoro-indole-2-carboxylic acid [2-(1H-indol-3-yl)-ethyl]-amide) | 321.4 | 1u | | | | 10 |
| (5-fluoro-indol-2-yl)-pyrrolidin-1-yl-methanone | 232.3 | 1v | | | | |
| (5-fluoro-indol-2-yl)-morpholin-4-yl-methanone | 248.3 | 1w | | | | 10 |
| (5-fluoro-indol-2-yl)-piperidin-1-yl-methanone | 246.3 | 1x | | | | |
| 5-fluoro-indole-2-carboxylic acid (1-hydroxymethyl-2-phenyl-ethyl)-amide | 312.3 | 1y | | | | |
| 5-fluoro-indole-2-carboxylic acid 3-fluoro-benzylamide | 286.3 | 1z | | 26 | | |
| 5-fluoro-indole-2-carboxylic acid [1-(3-methoxy-phenyl)-ethyl]-amide | 312.3 | 1aa | | 12 | | 10 |
| 5-fluoro-indole-2-carboxylic acid benzylamide | 268.3 | 1bb | | 19 | | |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| (5-fluoro-1H-indole-2-carboxamide, N-(2-hydroxy-1,2-diphenylethyl)) | 374.4 | 1cc | | 19 | | |
| (5-fluoro-1H-indole-2-carboxamide, N-(2-hydroxy-1,2-diphenylethyl), diastereomer) | 374.4 | 1dd | | 41 | | |
| (5-fluoro-N-(4-methoxybenzyl)-1H-indole-2-carboxamide) | 298.3 | 1ee | | 16 | | |
| (5-fluoro-N-(3-iodobenzyl)-1H-indole-2-carboxamide) | 294.2 | 1ff | | 24 | | |
| (5-fluoro-N-phenethyl-1H-indole-2-carboxamide) | 282.3 | 1gg | | | | |
| (5-fluoro-N-(2,4-dimethoxybenzyl)-1H-indole-2-carboxamide) | 328.3 | 1hh | | | | |
| (5-fluoro-N-(2-methoxybenzyl)-1H-indole-2-carboxamide) | 298.3 | 1ii | | | | |
| (5-fluoro-N-(3-trifluoromethylbenzyl)-1H-indole-2-carboxamide) | 336.3 | 1jj | | | | 18 |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| 5-F-indole-2-C(O)NH-CH2-C6H4-4-CF3 | 336.3 | 1kk | | | | |
| 5-F-indole-2-C(O)NH-CH2-C6H4-2-CF3 | 336.3 | 1ll | | | | |
| 5-F-indole-2-C(O)NH-CH2CH2-C6H4-4-OH | 298.3 | 1mm | | | | |
| 5-F-indole-2-C(O)NH-CH2-cyclohexyl | 274.3 | 1nn | | | | |
| 5-F-indole-2-C(O)NH-C6H4-4-CH2OH | 284.3 | 1oo | | | | 17 |
| 5-F-indole-2-C(O)NH-CH2-CH(OH)-Ph | 298.3 | 1pp | | | | |
| 5-F-indole-2-C(O)NH-CH2-C6H3-2,3-Cl2 | 337.2 | 1qq | | | | |
| 5-F-indole-2-C(O)NH-CH2-C6H2-2,4,6-(OMe)2,(OMe) | 358.4 | 1rr | | | | 12 |
| 5-F-indole-2-C(O)NH-CH2-C6H3-2,4-Cl2 | 337.2 | 1ss | 12 | | | |

TABLE 3-continued
INHIBITION OF EGFRPTK, p56 lck, p55 fyn, and PTP-1B
| Structure | MW | Compound Code | PTP-1B @ 10 μm | EGFRTK @ 10 μm | p56 Lck @ 10 μm | p55 fyn @ 10 μm |
|---|---|---|---|---|---|---|
| 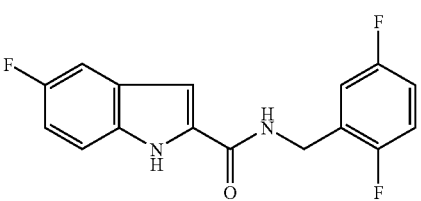 | 304.3 | 1tt | | | | |
| 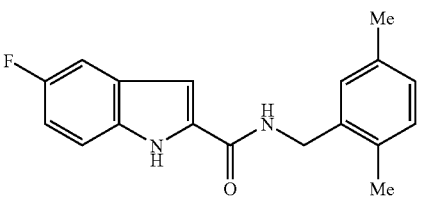 | 296.3 | 1uu | | | | |
| 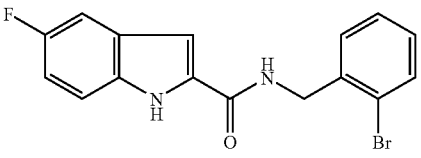 | 347.2 | 1vv | | | | |
| 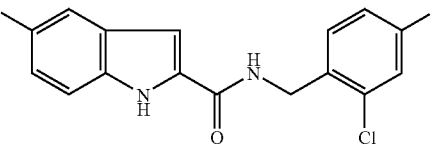 | 320.7 | 1ww | | | | |
| 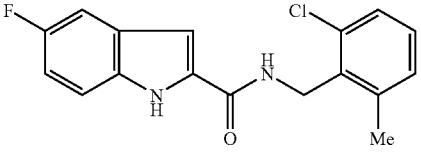 | 316.8 | 1xx | | | | 14 |
| 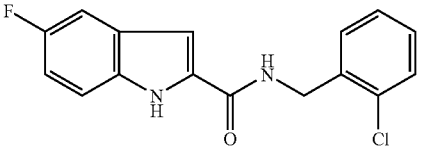 | 302.7 | 1yy | 10 | | | 12 |
| 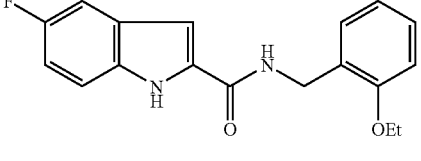 | 312.3 | 1zz | | | | |
| 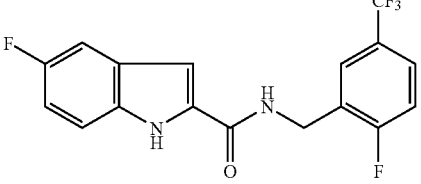 | 354.3 | 1aaa | 12 | | | |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| 5-F-indole-2-C(O)NH-CH2-(2-F-phenyl) | 286.3 | 1bbb | | | | |
| 5-F-indole-2-C(O)NH-CH2-(3,4,5-triOMe-phenyl) | 358.4 | 1ccc | | | | |
| 5-F-indole-2-C(O)NH-CH2-(3,4-diCl-phenyl) | 337.2 | 1ddd | | | | |
| 5-F-indole-2-C(O)NH-CH2-(3,4-diF-phenyl) | 304.3 | 1eee | | | | |
| 5-F-indole-2-C(O)NH-CH2-(3,5-diCF3-phenyl) | 404.3 | 1fff | | | | |
| 5-F-indole-2-C(O)NH-CH2-(3,5-diCl-phenyl) | 337.2 | 1ggg | | | | |
| 5-F-indole-2-C(O)NH-CH2-(3,5-diF-phenyl) | 304.3 | 1hhh | | | | |
| 5-F-indole-2-C(O)NH-CH2-(3-OCF3-phenyl) | 352.3 | 1iii | | | | |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| [5-fluoro-1H-indole-2-carboxamide N-(3-bromobenzyl)] | 347.2 | 1jjj | | | | |
| [5-fluoro-1H-indole-2-carboxamide N-(4-fluoro-3-chlorobenzyl)] | 320.7 | 1kkk | | | | |
| [5-fluoro-1H-indole-2-carboxamide N-(3-chlorobenzyl)] | 302.7 | 1lll | | | | |
| [5-fluoro-1H-indole-2-carboxamide N-(3-CF3-5-fluorobenzyl)] | 354.3 | 1mmm | | | | 14 |
| [5-fluoro-1H-indole-2-carboxamide N-(3-methylbenzyl)] | 282.3 | 1nnn | | | | |
| [5-fluoro-1H-indole-2-carboxamide N-(biphenyl-3-ylmethyl)] | 344.4 | 1ooo | | | | |
| [5-fluoro-1H-indole-2-carboxamide N-(4-OCF3-benzyl)] | 352.3 | 1ppp | | | | |
| [5-fluoro-1H-indole-2-carboxamide N-(4-benzyloxy-3-methoxybenzyl)] | 404.4 | 1qqq | | | | 11 |

TABLE 3-continued
INHIBITION OF EGFRPTK, p56 lck, p55 fyn, and PTP-1B
| Structure | MW | Compound Code | PTP-1B @ 10 μm | EGFRTK @ 10 μm | p56 Lck @ 10 μm | p55 fyn @ 10 μm |
| --- | --- | --- | --- | --- | --- | --- |
| 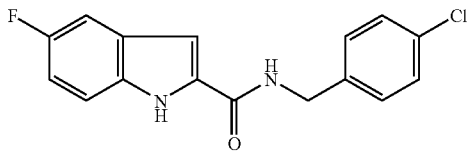 | 302.7 | 1rrr | | | | 15 |
| 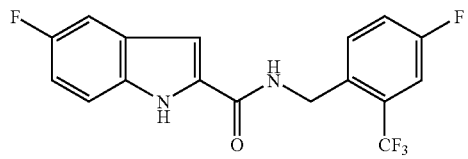 | 354.3 | 1sss | | | | |
| 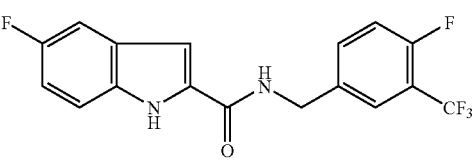 | 354.3 | 1ttt | | | | |
| 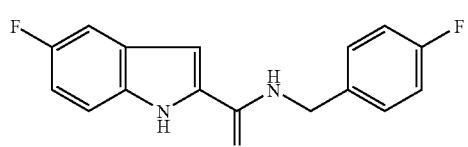 | 286.3 | 1uuu | 13 | | | 16 |
| 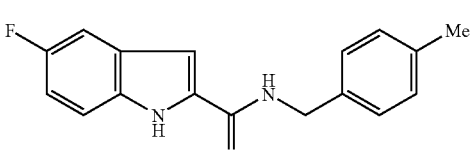 | 282.3 | 1vvv | | | | |
| 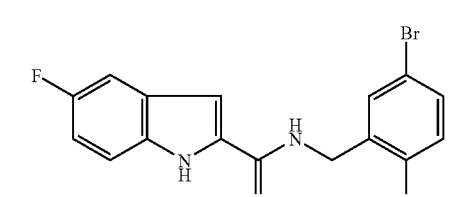 | 365.2 | 1www | | | | |
| 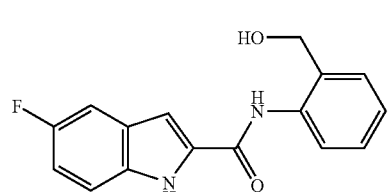 | 284.3 | 1xxx | 12 | | | |
| 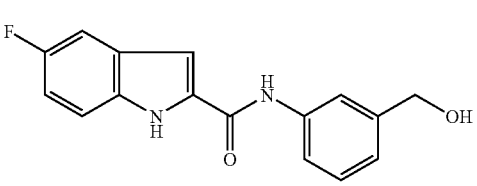 | 284.3 | 1yyy | | 11 | | |

TABLE 3-continued
INHIBITION OF EGFRPTK, p56 lck, p55 fyn, and PTP-1B
| Structure | MW | Compound Code | PTP-1B @ 10 μm | EGFRTK @ 10 μm | p56 Lck @ 10 μm | p55 fyn @ 10 μm |
|---|---|---|---|---|---|---|
| 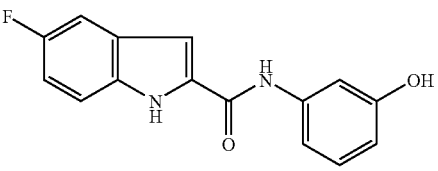 | 270.3 | 1zzz | | | | |
| 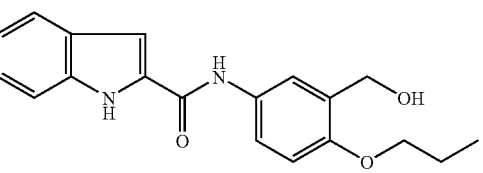 | 342.4 | 1aaaa | | | | |
| 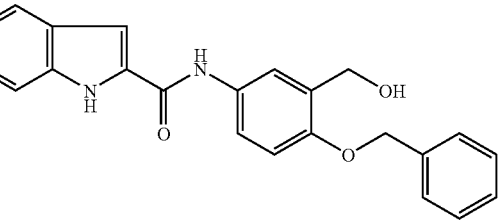 | 390.4 | 1bbbb | | | | |
| 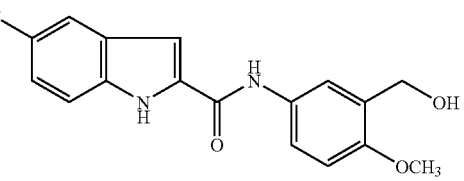 | 314.3 | 1cccc | 20 | 19 | | |
| 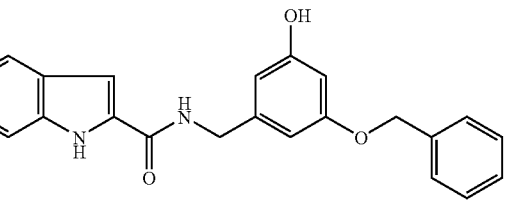 | 390.4 | 1dddd | 16 | | | |
| 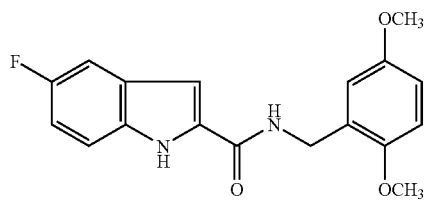 | 328.3 | 1eeee | | | | |
| 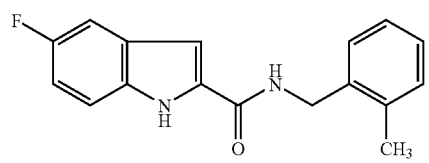 | 282.3 | 1ffff | | 12 | | |

TABLE 3-continued
INHIBITION OF EGFRPTK, p56 lck, p55 fyn, and PTP-1B
| Structure | MW | Compound Code | PTP-1B @ 10 μm | EGFRTK @ 10 μm | p56 Lck @ 10 μm | p55 fyn @ 10 μm |
|---|---|---|---|---|---|---|
| 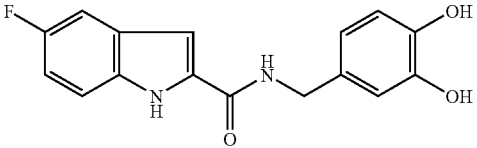 | 300.3 | 1gggg | | 25 | | |
| 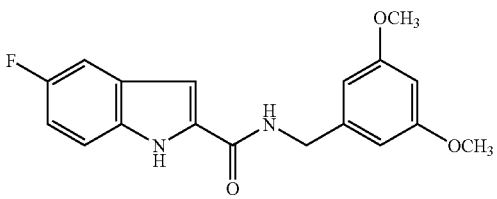 | 328.3 | 1hhhh | 17 | | | |
| 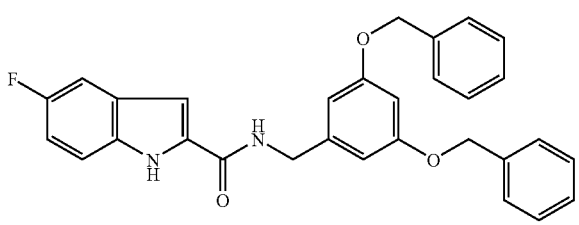 | 480.5 | 1iiii | | 12 | | |
| 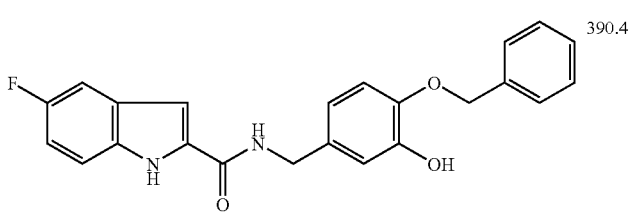 | 390.4 | 1jjjj | 15 | | | |
| 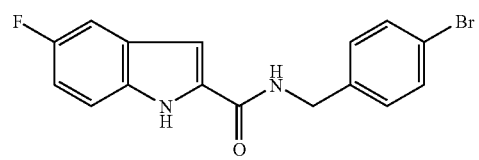 | 347.2 | 1kkkk | | 30 | | |
| 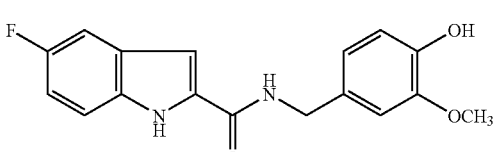 | 314.3 | 1llll | | | | |
| 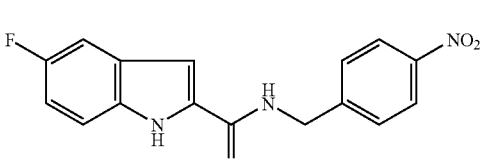 | 313.3 | 1mmmm | | | | 29 |
| 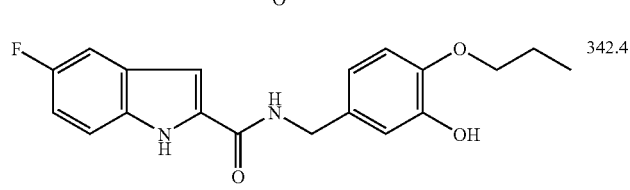 | 342.4 | 1nnnn | | 17 | | 11 |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| | 298.3 | 1oooo | | 33 | 10 | |
| | 298.3 | 1pppp | | | | |
| 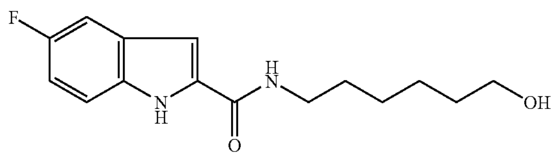 | 278.3 | 1qqqq | | 18 | | |
| 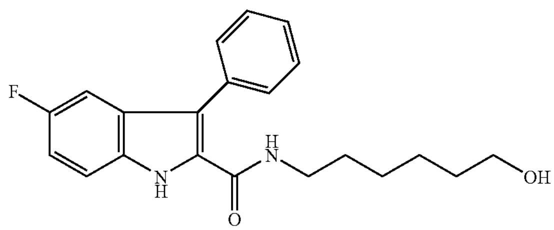 | 354.4 | 2a | | | | |
| 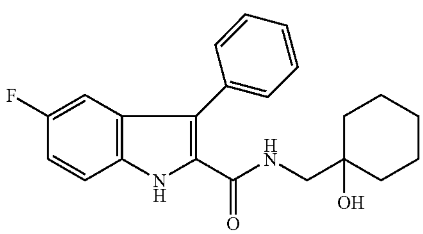 | 366.4 | 2b | | 19 | | 13 |
| 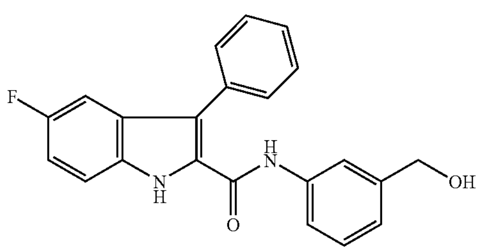 | 360.4 | 2c | | | | |
| 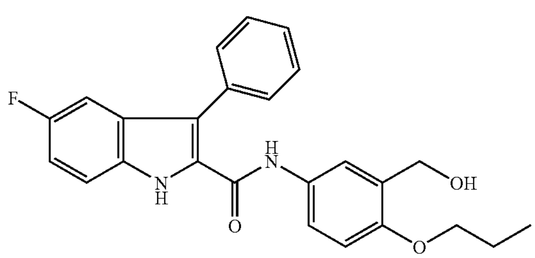 | 418.5 | 2d | | 23 | | |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| 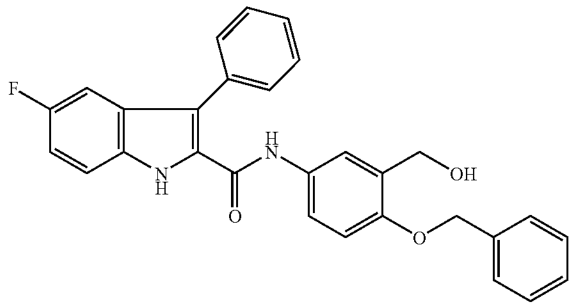 | 466.5 | 2e | | 10 | | |
| 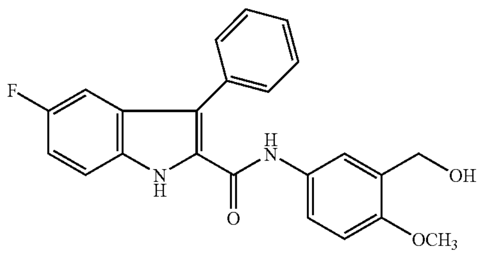 | 390.4 | 2f | | 18 | | 11 |
| 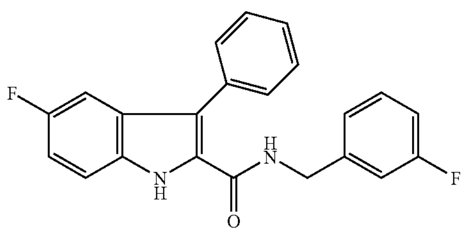 | 362.4 | 2g | | | | |
| 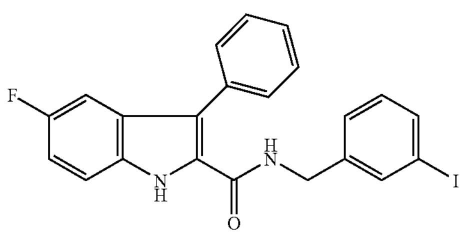 | 470.3 | 2h | | | | |
| | 412.4 | 2i | | | | |
| | 412.4 | 2j | | 20 | | |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| 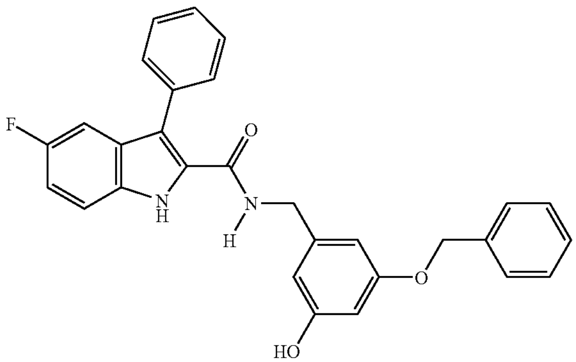 | 466.5 | 2k | | | | |
| | 413.3 | 2l | | | | |
| 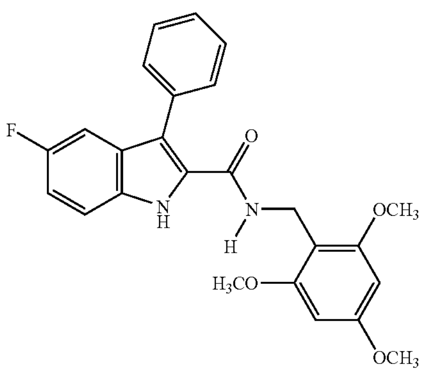 | 434.5 | 2m | | | | |
| | 413.3 | 2n | | | | |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| 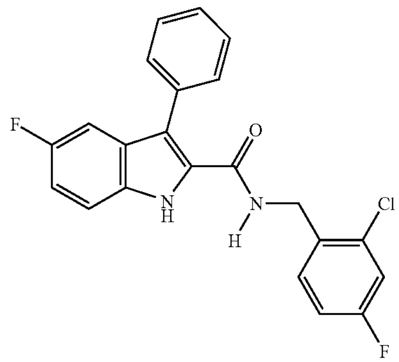 | 396.8 | 2o | | | | 12 |
| 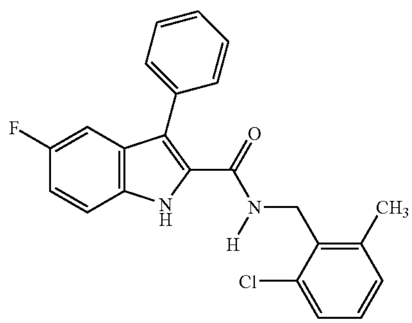 | 392.9 | 2p | | | | |
| 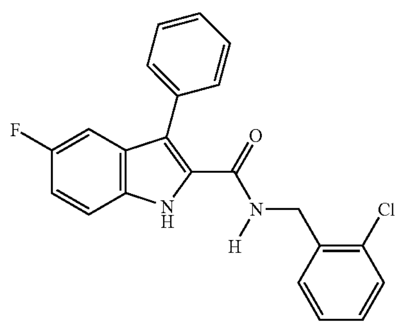 | 378.8 | 2q | | | | |
| 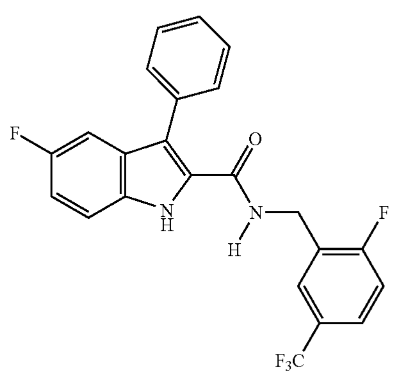 | 430.4 | 2r | | | | |

TABLE 3-continued
INHIBITION OF EGFRPTK, p56 lck, p55 fyn, and PTP-1B
| Structure | MW | Compound Code | PTP-1B @ 10 μm | EGFRTK @ 10 μm | p56 Lck @ 10 μm | p55 fyn @ 10 μm |
|---|---|---|---|---|---|---|
| 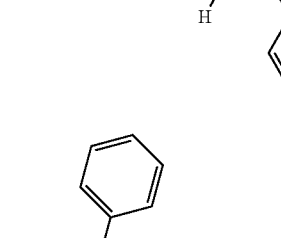 | 362.4 | 2s | | 33 | 10 | 11 |
| 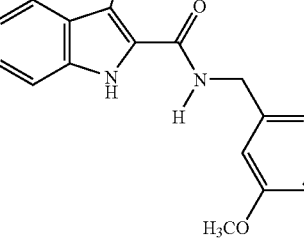 | 434.5 | 2t | | | | |
| 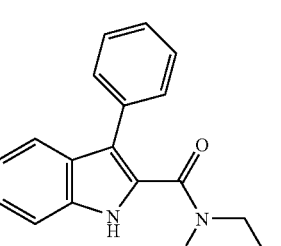 | 413.3 | 2u | | | | |
| 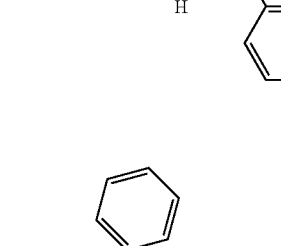 | 380.4 | 2v | | | | |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| (5-fluoro-3-phenyl-1H-indole-2-carboxylic acid [3,5-bis(trifluoromethyl)benzyl]amide) | 480.4 | 2w | 12 | | | |
| (5-fluoro-3-phenyl-1H-indole-2-carboxylic acid 3,5-dichlorobenzylamide) | 413.3 | 2x | | | | |
| (5-fluoro-3-phenyl-1H-indole-2-carboxylic acid 3,5-difluorobenzylamide) | 380.4 | 2y | | 20 | | |
| (5-fluoro-3-phenyl-1H-indole-2-carboxylic acid 3,5-dimethoxybenzylamide) | 404.4 | 2z | | | | |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| 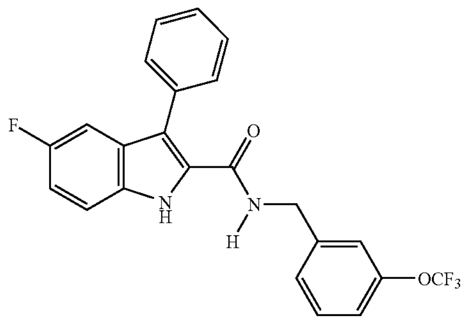 | 428.4 | 2aa | | | | |
| 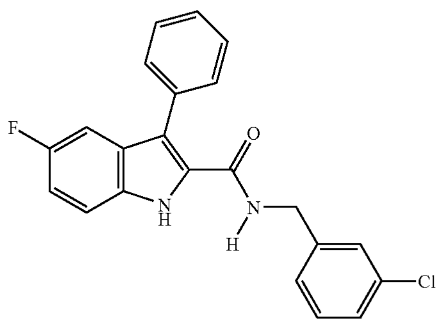 | 378.8 | 2bb | | | | |
| 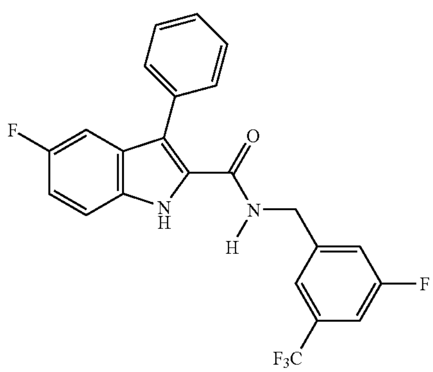 | 430.4 | 2cc | | | | |
| 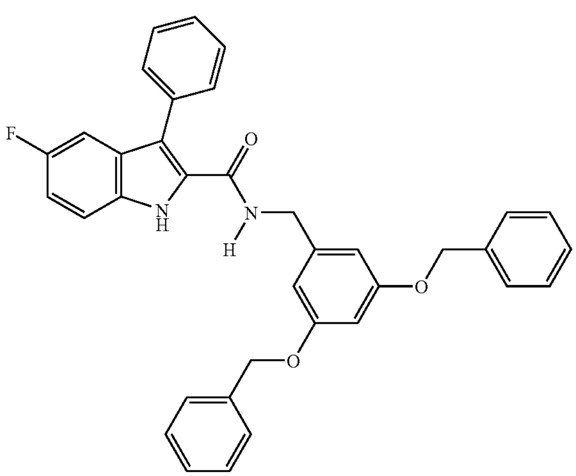 | 556.6 | 2dd | | | | |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| 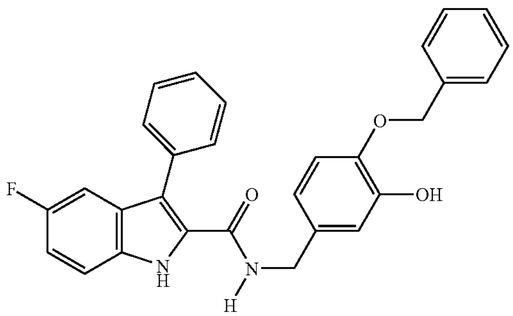 | 466.5 | 2ee | | | | |
| 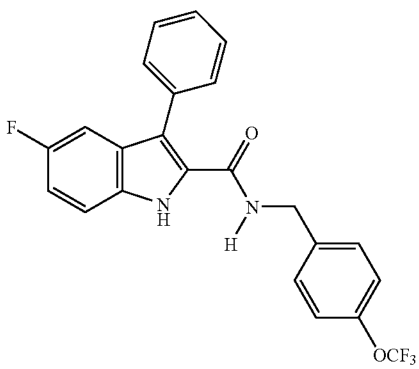 | 428.4 | 2ff | | | | |
| 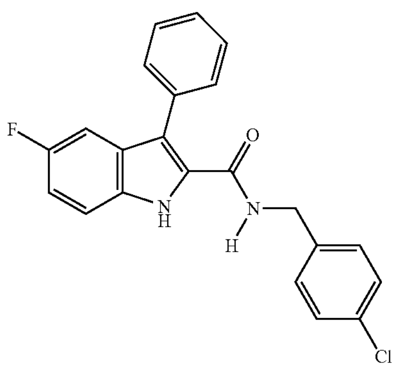 | 378.8 | 2gg | | 12 | | |
| 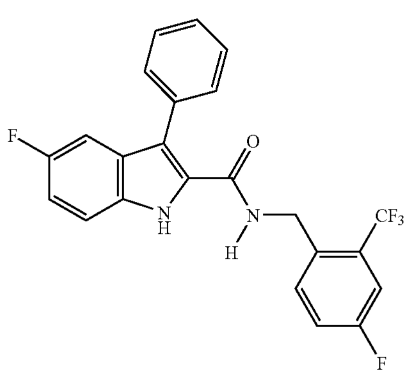 | 430.4 | 2hh | | 12 | | |

TABLE 3-continued

INHIBITION OF EGFRPTK, p56 lck, p55 fyn, and PTP-1B

| Structure | MW | Compound Code | PTP-1B @ 10 μm | EGFRTK @ 10 μm | p56 Lck @ 10 μm | p55 fyn @ 10 μm |
|---|---|---|---|---|---|---|
| 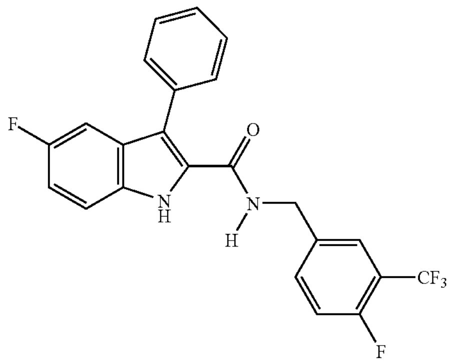 | 430.4 | 2ii | | | | |
| 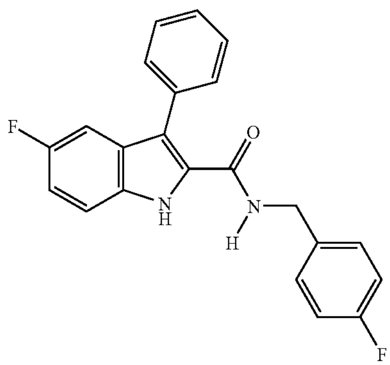 | 362.4 | 2jj | | | | |
| 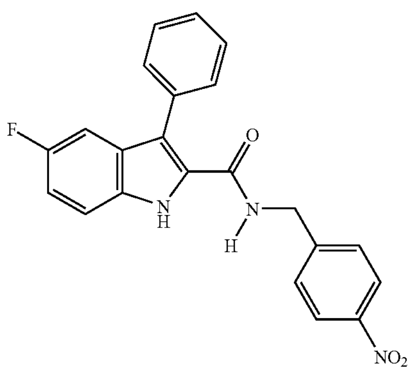 | 389.4 | 2kk | | | | 24 |
| 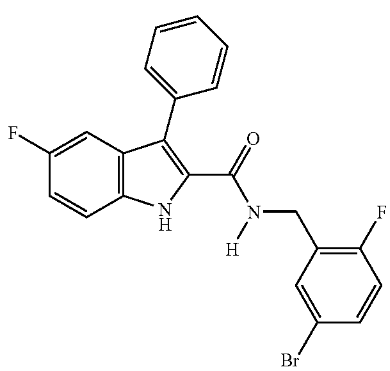 | 441.3 | 2ll | | 10 | | |

TABLE 3-continued
INHIBITION OF EGFRPTK, p56 lck, p55 fyn, and PTP-1B
| Structure | MW | Compound Code | PTP-1B @ 10 µm | EGFRTK @ 10 µm | p56 Lck @ 10 µm | p55 fyn @ 10 µm |
|---|---|---|---|---|---|---|
| 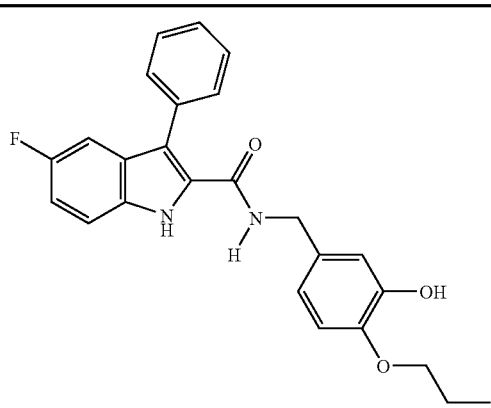 | 418.5 | 2mm | | | | |
| 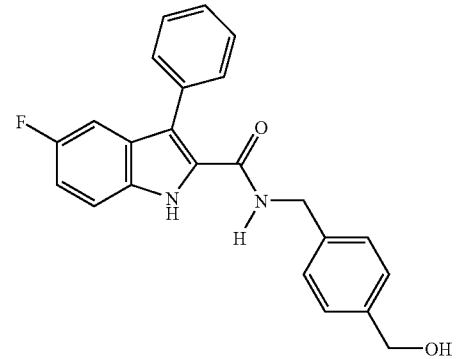 | 374.4 | 2nn | | | | |
| 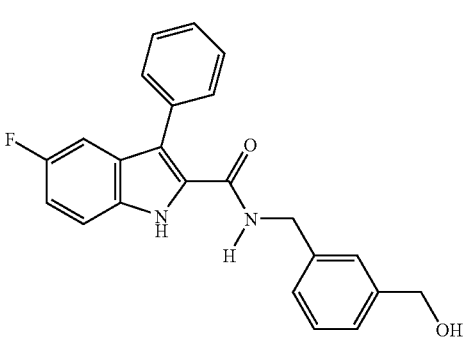 | 374.4 | 2oo | | | | |

E. Mice Toxicity Study

FIG. 1 shows the results of a maximum tolerated dose (MTD) study with two indole inhibitors:

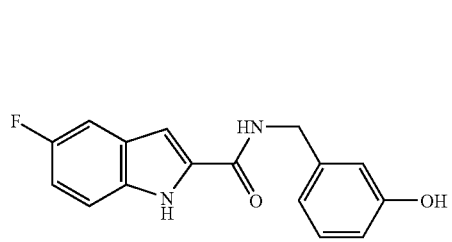
1a

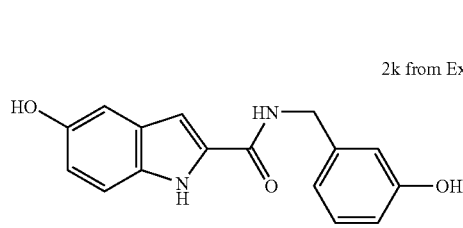
2k from Example 4

These compounds were administered to SCID mice by intraperitoneal administration in tween80:EtOH. The results in FIG. 1 show that compound 1a is less toxic in mice than compound 2k from Example 4, since the mice exhibited less weight loss when compound 1a was administered.

Example 2

Synthesis and Activity of 7-Substituted Indole Derivative Protein Kinase Inhibitors 7-substituted indole derivative protein kinase inhibitors were synthesized as set forth in Scheme 1, below:

Scheme 1

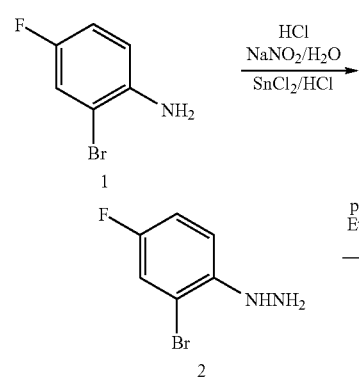

-continued

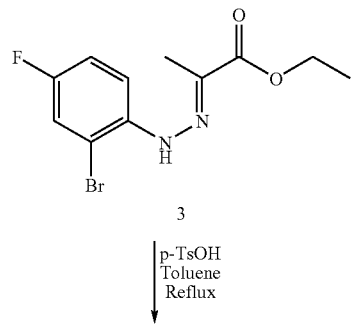
3

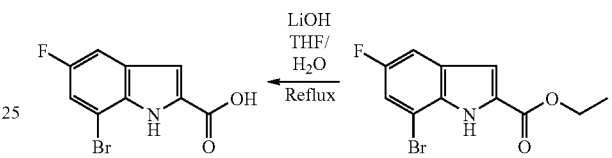
5    4

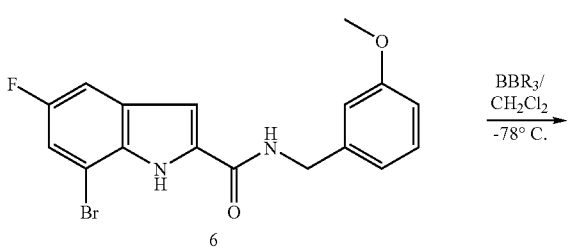
6

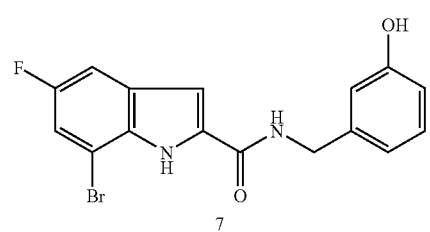
7

(2-bromo-4-fluoro-phenyl)-hydrazine (2)

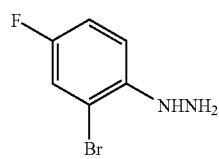

Commercially available 2-bromo-4-fluoroaniline 1 (2.36 ml, 20.75 mmol) was added to a stirring solution of concentrated hydrochloric acid (40 ml) that was cooled to −5° C. This solution was allowed to age while stirring for 10 minutes. An aqueous solution of NaNO$_2$ was added over 15 minutes. SnCl$_2$/HCl (10.40 g, 46.1 mmol, 10 ml HCl) was added over 15 minutes and aged for an additional 30 minutes to 1 hour. The mixture was filtered and washed with dichloromethane. The resulting solid was dissolved in 1.0M HCl and extracted 3 times with dichloromethane. The organic layer was vacuum dried overnight to give 3.53 g (83% yield). $^1$H NMR (400 MHz, CDCl$_3$): δ7.169 (dd, J=8 Hz, J=2.8 Hz 1H), δ 7.076 (dd, J=5.2 Hz, J=9.2 Hz, 1H), δ6.982 (td, J=8.4 Hz, J=2 Hz 1H), δ 5.540 (bs, 1H), δ 3.590 (bs, 1H).

2-[(2-bromo-4-fluoro-phenyl)-hydrazono]-propionic acid ethyl ester (3)

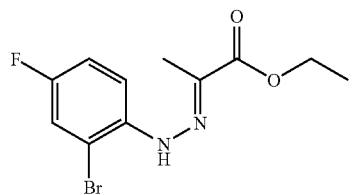

Commercially available p-toluensulfonic acid (38.37 mg, 0.217 mmol) was added to 60 ml of toluene in a round bottom flask and magnetic stir bean. The flask was then fitted with a Dean Stark trap and reflux condenser. The solution was then allowed to stir for 2 hours. After 2 hours, the solution was cooled and 2-(bromo-4-phenyl)hydrazine (4.135 g, 20.17 mmol) was added. The solution was then refluxed for an additional 1.5 hours using the same apparatus. After 1.5 hours, the solution was placed on the rotary evaporator to remove the toluene. A dark brown tar-like substance was left in the flask. An appropriate amount of hexanes were added to the flask and refluxed to dissolve the pure hydrazine. The hexanes took on a yellow color and were then decanted hot into another flask leaving the tar-like side product behind. This was repeated. The flask containing the hexane solution was refluxed so as to dissolve the precipitating hydrazine and placed in the freezer to form crystals. 3.6 g (11.9 mmol, 87% yield) of 3. $^1$H NMR (Acetone-d$_6$): δ 12.369 (bs, 1H), δ 7.646 (dd, J=9.2 Hz, J=5.6 Hz 1H), δ 7.449 (dd, J=8.2 Hz, J=2.8 Hz 1H), δ 7.22 (td, J=~8.6 Hz, J=2.8 Hz, 1H), δ 4.37 (q, J=7.2 Hz, 2H), δ 2.203 (s, 3H), δ 1.402 (t, J=7.2 Hz, 3H).

7-bromo-5-fluoro-1H-indole-2-carboxylic acid ethyl ester (4)

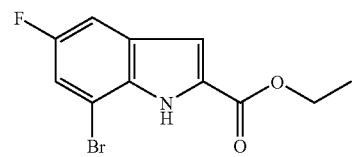

Commercially available p-toluensulfonic acid dihydrate (2.26 g, 11.9 mmol) was added to 120 ml of toluene and dried under reflux using a Dean Stark apparatus for 2 hours. 2-[(2-bromo-4-fluoro-phenyl)-hydrazono]-propionic acid ethyl ester (3.6 g, 11.9 mmol), was added to the cooled solution, and refluxed for an additional 1.5 hours. After 1.5 hours the solution was cooled. The toluene was removed under reduced pressure. Then the solid was refluxed with hexane to isolate the indole ester. The resulting hexane solution was refluxed to dissolve the precipitating indole, and placed in the freezer for crystallization. After removal of supernatant and drying of crystals gave 3.30 g, 11.543 mmol of 4 (97% yield). $^1$H NMR (400 MHz, Acetone-d$_6$): δ 10.85 (bs, 1H), δ 7.45 (dd, J=9.2 Hz, J=2.4 Hz, 1H), δ 7.39 (dd, J=9.2 Hz, J=2.0 Hz, 1H), δ 7.28 (d, J=2.0 Hz, 1H), δ 4.36 (q, J=6.8 Hz, 2H), δ 1.345 (t, J=6.8 Hz, 1H).

7-bromo-5-fluoro-1H-indole-2-carboxylic acid (5)

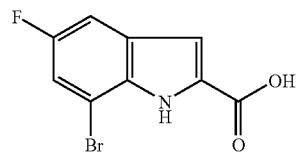

Tetrahydrofuran (35.2 ml), water (23.5 ml), lithium hydroxide (2.61 g, 10.9 mmol), and 7-bromo-5-fluoro-1H-indole-2-carboxylic acid ethyl ester (3.11 g, 10.9 mmol) were added to a round bottom flask and mixed with a magnetic stirrer. This mixture was refluxed for 1 hour. The THF was removed via rotary evaporator, and the aqueous solution was acidified with 1M HCL, and extracted with ethyl acetate. $^1$H NMR (DMSO-d$_6$): δ 13.206 (bs, 1H), δ 11.876 (s, 1H), δ 7.498-7.445 (m, 2H), δ 7.19 (d, J=2.0 Hz, 1.0H).

7-bromo-5-fluoro-1H-indole-2-carboxylic acid 3-methoxy-benzylamide (6)

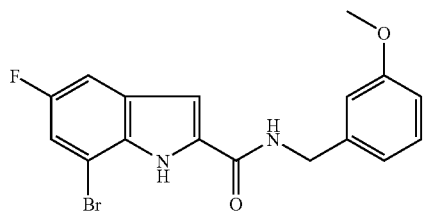

To a round bottom flask that has been fire dried, flushed with a continuous stream of argon, and equipped with a stir bean, DMF (4.8 ml) was added. To this stirring solution 5 (600 mg, 2.33 mmol), was combined with methoxybenzylamine (328 μL, 2.56 mmol), and PyBOP (1.33 g, 2.56 mmol). This solution was then cooled to a temperature of 0 degrees C. After 2 minutes diisopropylamine (1.7 ml, 9.67 mmol) was added and the entire solution was allowed to stir at room temperature overnight. The reaction was then diluted with roughly 60 ml of ethyl acetate and extracted 3× with saturated sodium bicarbonate, and 3× with 1M HCl in appropriate volumes to remove any unreacted starting materials. The ethyl acetate layer was isolated and dried over sodium sulfate. The ethyl acetate was removed using a rotary evaporator to yield a brownish film on the sides of the flask. Hexanes were added to the flask and refluxed. A solid then formed on the sides of the flask, and the hexanes were removed via rotary evaporator to give 709.0 mg of 6 (81% yield). $^1$H NMR (400 MHz, DMSO-$d_6$) δ 11.537 (bs, 1H), δ 9.092 (t, J=5.6 Hz, 1H), δ 7.49 (dd, J=9.4 Hz, J=2.4 Hz 1H), δ (dd, J=8.8 Hz, J=2 Hz 1H), δ 7.268-7.228 (m, 2H), δ 6.91 (d, J=6.8 Hz, 2H), δ 6.82 (d, J=8.2 Hz, 1H), δ 4.48 (d, J=6 Hz, 2H), δ 3.729 (s, 3H).

7-bromo-5-fluoro-1H-indole-2-carboxylic acid 3-hydroxy-benzylamide (7)

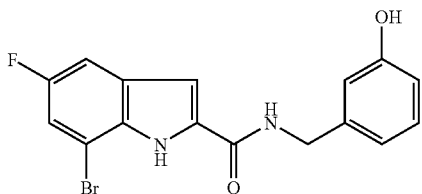

A stirring solution of methylene chloride (1 ml) was cooled to −78 degrees in a dry ice acetone bath and flushed with a stream of argon. To this cold stirring solution 6 (50 mg, 0.133 mmol) was added. 7 equivalents of $BBr_3$ was added and allowed to stir at −78 degrees for 1 hour, and then the solution was allowed to stir at room temperature overnight. The reaction was then quenched with excess water, then neutralized with saturated sodium bicarbonate, and extracted with methylene chloride. The methylene chloride layer was dried over sodium sulfate and removed under reduced pressure to yield 35.0 mg of 2 (70% yield). $^1$H NMR (400 MHz, Acetone-$d_6$) δ 10.633 (bs, 1H), δ 8.42 (d, J=15.6, 2H), 7.48 (dd, J=9.2 Hz, J=2.4 Hz, 1H), δ 7.42 (dd, J=9 Hz, J=2.4 Hz, 1H), δ 7.373 (d, J=2.4 Hz, 1H), δ 7.217 (t, J=7.6 Hz, 1H), δ 6.932-6.898 (m, 2H), δ 6.80 (dd, J=2 Hz, J=8 Hz, 1H), δ 4.634 (d, J=5.6 Hz, 2H). Disappearance of the characteristic methoxy peak at 3.7 ppm indicates a successful deprotection.

Example 3

Design, Synthesis and Activity of Non-ATP Competitive Hydroxynaphthalene Derivative Inhibitors of pp60$^{c-Src}$ Tyrosine Kinase The crystal structure of the autoinhibited human IRTK catalytic domain (Hubbard et al., 1994) was used to carry out qualitative molecular modeling studies (SYBYL™, 6.4, Tripos Inc., St. Louis) wherein a naphthalene ring was superimposed upon the IRTK Tyr 1,162. The IRTK region containing Tyr 1,162 folds back into the active site, with Tyr 1,162 positioned analogous to a phosphorylatable Tyr in a peptide substrate, thereby autoinhibiting the tyrosine kinase. This superimposition indicated that an amide carbonyl should be placed at the 2-position (Scheme 1) of the

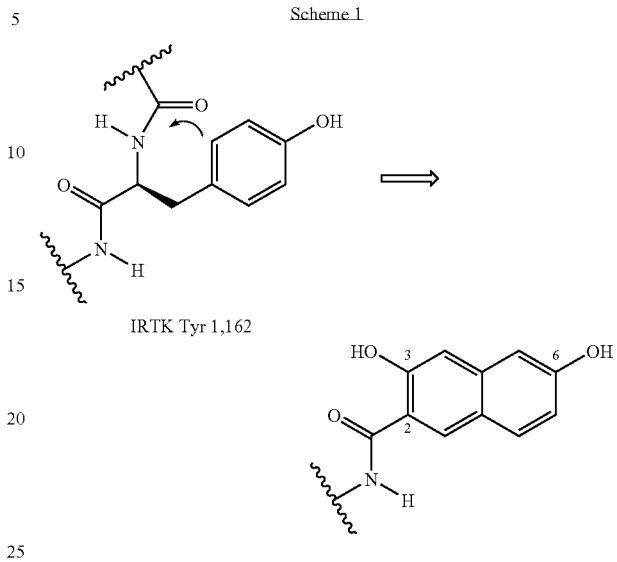

naphthalene ring to mimic the Tyr 1,162 carbonyl and a hydroxyl group should be positioned at the 6-position to mimic the Tyr 1,162 hydroxyl group. These modeling studies also indicated that a hydroxyl group at the 3-position could mimic the Tyr 1,162 NH.

In order to test these design concepts experimentally, the 2-position carbonyl group was appended as either a methyl ester or as a series of amides (Table 4). The hydroxy N-phenyl (X=0) and N-benzyl (X=1) amides were chosen based upon the increase in pp60$^{c-src}$ inhibitor potency observed with iminochromene analogs containing appended hydroxy N-phenyl amide side-chains (Huang et al., 1995). Analogs wherein the 6-hydroxyl group was either deleted or moved were also prepared to determine if a drop in potency occurs as predicted from the modeling studies.

The series of 2-carbonyl-3,5-dihydroxy naphthalene inhibitors (1a, 2a-2d, 2i-2l, 2o-2p) and 2-carbonyl-3,7-dihydroxy naphthalene inhibitors (1c, 2t-2u) were synthesized from commercially available (Aldrich) 3,5-dihydroxy-2-naphthoic acid and 3,7-dihydroxy-2-naphthoic acid, respectively. The methyl esters 1a and 1c were obtained by refluxing the respective acid starting materials for 48 h in methanol pre-saturated with HCl gas. The amides (2a-2d, 2i-2l, 2o-2p, 2t-2u) were synthesized by coupling the respective carboxylic acid with commercially available (Aldrich or Lancaster) amines using one of two methods. The first method utilized the NBS/PPh$_3$ methodology as described by Froyen (Froyen, 1997). The second method utilized IIDQ (Aldrich) as the coupling reagent. The carboxylic acid was first reacted with 1.0 eq. IIDQ in anhydrous DMF at room temperature for 24 hours. The respective amine (2.0 eq.) was then added neat and the reaction was heated to 80° C. for 2-6 hours. After aqueous workup, purification was achieved by silica gel chromatography and precipitation from $CH_2Cl_2$/hexane, followed by preparative C-18 RP-HPLC ($CH_3CN/H_2O$), if necessary. The benzyl amines were commercially available only as their corresponding hydroxylprotected methyl ethers. Consequently, after amide formation, the hydroxyl groups were deprotected by treatment with 6 eq. $BBr_3$ in DCM for 1 minute at −78° C. followed by 1 hour at room temperature.

TABLE 4 pp60[c-src] INHIBITORY ACTIVITY OF HYDROXYNAPHTHALENE DERIVATIVES AND SELECT PUBLISHED INHIBITORS.[a,b,c]

(1a-1d)

(2a-2v)

| Cmpd | $R_1$ | $R_2$ | $R_3$ | $R_4$ | $R_5$ | $R_6$ | $R_7$ | X | % Inhibition at 100 µM (std. dev.) | $IC_{50}$ (µM) |
|---|---|---|---|---|---|---|---|---|---|---|
| 1a | OH | OH | H | H | N/A | N/A | N/A | N/A | 5 (+/−2) | n.t. |
| 1b | OH | H | OH | H | N/A | N/A | N/A | N/A | 47 (+/−3) | n.t. |
| 1c | OH | H | H | OH | N/A | N/A | N/A | N/A | 19 (+/−6) | n.t. |
| 1d | $NH_2$ | H | H | H | N/A | N/A | N/A | N/A | Inactive | n.t. |
| 2a | OH | OH | H | H | OH | H | H | 0 | 12 (+/−4) | n.t. |
| 2b | OH | OH | H | H | H | OH | H | 0 | 51 (+/−1) | 150 |
| 2c | OH | OH | H | H | H | H | OH | 0 | 60 (+/−7) | n.t. |
| 2d | OH | OH | H | H | OH | H | OH | 0 | 14 (+/−2) | n.t. |
| 2e | OH | H | OH | H | OH | H | H | 0 | 39 (+/−5) | n.t. |
| 2f | OH | H | OH | H | H | OH | H | 0 | 89 (+/−1) | 16 |
| 2g | OH | H | OH | H | H | H | OH | 0 | 23 (+/−5) | n.t. |
| 2h | OH | H | OH | H | OH | H | OH | 0 | 56 (+/−1) | n.t. |
| 2i | OH | OH | H | H | H | OMe | H | 0 | 33 (+/−5) | n.t. |
| 2j | OH | OH | H | H | H | H | OMe | 0 | 35 (+/−8) | n.t. |
| 2k | OH | OH | H | H | OMe | H | H | 1 | 13 (+/−3) | n.t. |
| 2l | OH | OH | H | H | H | H | OMe | 1 | 14 (+/−2) | n.t. |
| 2m | OH | H | OH | H | OMe | H | H | 1 | inactive | n.t. |
| 2n | OH | H | OH | H | H | H | OMe | 1 | 4 (+/−7) | n.t. |
| 2o | OH | OH | H | H | OH | H | H | 1 | 41 (+/−2) | n.t. |
| 2p | OH | OH | H | H | H | H | OH | 1 | 49 (+/−4) | n.t. |
| 2q | OH | H | OH | H | OH | H | H | 1 | 42 (+/−2) | n.t. |
| 2r | OH | H | OH | H | H | OH | H | 1 | 55 (+/−3) | n.t. |
| 2s | OH | H | OH | H | H | H | OH | 1 | 42 (+/−3) | n.t. |
| 2t | OH | H | H | OH | OH | H | H | 0 | 68 (+/−5) | n.t. |
| 2u | OH | H | H | OH | H | OH | H | 1 | 40 (+/−3) | n.t. |
| 2v | H | H | OH | H | H | OH | H | 0 | 45 (+/−5) | n.t. |
| Iminochromene 9TA | | | | | | | | | 30 (+/−15) | Lit[8]: 0.118 |
| Piceatannol | | | | | | | | | 41 (+/−2) | Lit[13]: 66 (lck) |
| ST-638 | | | | | | | | | 37 (+/−5) | Lit[14]: 18 |
| Emodin[d] | | | | | | | | | 22 (+/−3) | Lit[15]: 38 |
| Tyrophostin A47 | | | | | | | | | 43 (+/−3) | |

Table 4 Footnotes
[a]The previously described assay procedure (Lai et al., 1998) was used with the following assay components, final concentrations and conditions: 50.0 mM MOPS, 4.02 mM $MgCl_2$, 6.00 mM $K_3$citrate (used as a $Mg^{2+}$ buffer to stabilize the free $Mg^{2+}$ at 0.5 mM), 99.0 mM KCl, 10.0 mM 2-mercaptoethanol, 198 µM ATP, 19.8 µM ADP, 10 U full length human purified recombinant pp60[c-src] (Upstate Biotechnology Inc.), 2.00 mM RR-SRC, 4.0% DMSO, pH 7.2, 37° C.. These overall assay conditions have been shown (Choi, 1999) to reproduce the intracellular conditions of pH, temp., free $Mg^{2+}$ (0.5 mM), ionic strength, osmolality, ATP/ADP and reduction potential.
[b]All new compounds were characterized by proton NMR, EI or FAB(+) MS and are pure by TLC.
[c]N/A = Not applicable, n.t. = Not tested.
[d]ATP-competitive.

The series of 2-carbonyl, 3,6-dihydroxy naphthalene inhibitors (1b, 2e-2h, 2m-2n, 2q-2s) were synthesized from 3,6-dihydroxy-2-naphthoic acid 6 using the methods described above. The synthesis of intermediate 6 that was developed is shown in Scheme 2 beginning with commercially available 2,7-dihydroxynaphthalene 3 (Aldrich).

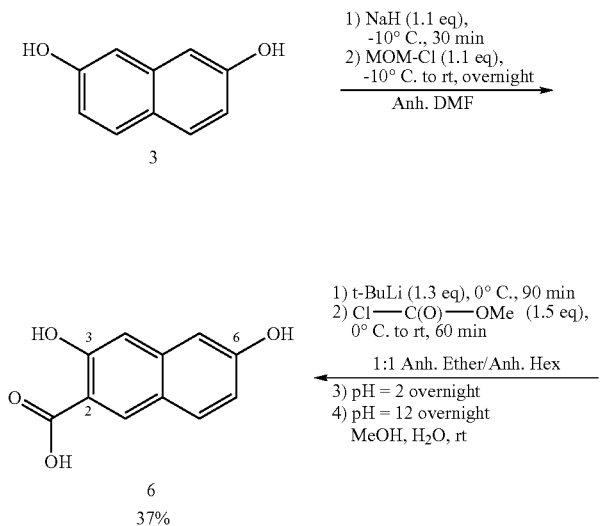

Compound 1d was synthesized from 3-amino-2-naphthoic acid (Aldrich) by reaction with TMS-diazomethane in DCM at room temperature. Compound 2v was synthesized from 6-hydroxy-2-naphthoic acid (Aldrich) using the amidation method described by Froyen (Froyen, 1997).

Kinase assay conditions have been shown to influence the measured inhibitory activity (Lawrence et al., 1998). Consequently, in order to accurately determine the relative potency of the newly designed class of pp60$^{c-src}$ inhibitors, the inhibitory activity of four previously published, non-ATP competitive PTK inhibitors, was also tested. Piceatannol, ST-638, and Tyrphostin A47 were chosen because they are commercially available (Sigma or Calbiochem), and are representative of the spectrum of known non-ATP competitive PTK inhibitors. Emodin (Calbiochem) is ATP-competitive when analyzed with the tyrosine kinase p56$^{lck}$. Previously, iminochromene 9TA was the most potent non-ATP competitive pp60$^{c-src}$ inhibitor reported (Huang et al., 1995). Since iminochromene 9TA was not commercially available, it was synthesized using a novel route by converting 3-Aminophenol to the corresponding TBDMS ether (1.1 eq. TBDMS-Cl, 1.1 eq. DIEA, 5 mol % DMAP, DMF, 24 h, rt, 71%). The resulting aniline was coupled using 2.0 eq. of cyanoacetic acid (1.1 eq. EDCI, 1.1 eq. TEA, DMF, 18 h, 75° C., 70%). Condensation of the resulting amide with 1.2 eq. of 2,3-dihydroxybenzaldehyde (cat. piperidine, abs. EtOH, 2 h, 60° C.) followed by deprotection (1.1 eq. TBAF, THF, 15 m, 43% overall) gave iminochromene 9TA with satisfactory elemental, FAB(+)MS and $^1$H NMR analysis after purification by flash chromatography (10:1, DCM:MeOH).

The inhibitory activities shown in Table 4 for compounds 1a-d and 2a-2v were determined using purified, full length, human recombinant pp60$^{c-src}$. Due to the number of compounds tested, and the associated cost, their rank order potencies were first determined at a constant inhibitor concentration (100 µM). As predicted by the modeling studies, based upon analogy to the IRTK Tyr 1,162 hydroxyl group, a preference for positioning the naphthalene hydroxyl group on carbon 6 vs. 5 or 7 was observed in both the ester (1b, 47% vs. 1a, 5% & 1c, 19%) and amide (e.g. 2f, 89% vs. 2b, 51% & 2t, 68%) series. The prediction that attaching a hydroxyl group at naphthalene carbon 3 (mimicking the Tyr 1,162 NH) would improve potency was also confirmed (2f, 89% vs. 2v, 45%). Finally, the prediction that extending the inhibitor as an amide at the 2 position (mimicking the peptide bond) could further improve potency was confirmed as well (e.g. 2f, 89% vs. 1b, 47%).

The data provided in Table 4 demonstrate that moving the hydroxyl group from the optimal 6 position to the adjacent naphthalene carbon 5 results in a different structure activity profile with regard to the optimal concurrent positioning of the hydroxyl group(s) in the amide side chain (e.g. 2f/2g vs. 2b/2c). Also of note is the replacement of the amide side chain hydroxyl group with a corresponding methoxy group in compounds 2i-2n. In the case of the N-phenyl amides (2i-2j), their activity, relative to the corresponding hydroxy amides (2b-2c), was not reduced as significantly as in the case of the N-benzyl amides (2k-2n vs. 2o-2q, 2s). This suggests that in the benzyl derivatives, the amide side chain hydroxyl groups either interact with the enzyme as hydrogen bond donors, or the methoxy groups are too large to fit in the binding site.

A more quantitative analysis of the selectivity for positioning a hydroxyl group on carbon 6 vs. 5 is provided by comparing the IC$_{50}$'s of 2f (16 µM) vs. 2b (150 µM), respectively. These results also confirm that a drop in % inhibition from ca. 90% to ca. 50% represents an order of magnitude difference in potency, as expected. Similarly, a drop in % inhibition from ca. 50% to 10% would represent another order of magnitude difference in potency.

A direct comparison of the most potent inhibitor from this series, compound 2f, with the five previously reported PTK inhibitors shown in Table 4 demonstrates that, under these assay conditions, 2f is more potent by one to two orders of magnitude. Interestingly, iminochromene 9TA was previously reported (Huang et al., 1995) to have an IC$_{50}$ of 118 nM against pp60$^{c-src}$, and was the most potent known non-ATP competitive pp60$^{c-src}$ inhibitor, but under the current assay conditions only a 30% inhibition at 100 µM was observed. These results re-emphasize (Lawrence et al., 1998) the importance of comparing protein kinase inhibitors under identical assay conditions.

A goal of these studies was to obtain non-peptide pp60$^{c-src}$ inhibitors which do not compete with ATP. Consequently the % inhibition of pp60$^{c-src}$ by 2f and 2b at constant inhibitor concentrations was monitored as a function of increasing [ATP] up to a cellular mimetic 1 mM level. Since the [ATP] had little effect on the % inhibition, both 2f and 2b are non-competitive inhibitors with respect to ATP. The % inhibition was measured using ATP concentrations of 200, 500 & 1,000 μM while holding the inhibitor concentration constant. If the inhibitor is directly competing with ATP, then this 5-fold overall increase in [ATP] is equivalent to decreasing the inhibitor concentration 5-fold in terms of the effect on % inhibition. Consequently the % inhibition should decrease to the value observed in the $IC_{50}$ dose-response curve (obtained with 200 μM ATP) for ⅕ of the set inhibitor concentration used in this experiment if direct competition with ATP is occurring. For inhibitor 2f (set at 25 μM) a 62% (+/−5), 54% (+/−3) and 50% (+/−1) inhibition at 200 μM, 500 μM and 1,000 μM ATP, respectively, was obtained whereas the level of inhibition should have dropped to ca. 20% at 1,000 μM ATP if direct competition with ATP were occurring. Similarly, for inhibitor 2b (set at 300 μM) an 84% (+/−1), 81% (+/−1) and 77% (+/−2) inhibition at 200 μM, 500 μM and 1,000 μM ATP, respectively, was obtained. The high cost of many kinases has stimulated other researchers to monitor inhibitor potency as a function of increasing [ATP] for the same purpose (Saperstein et al., 1989; Burke et al., 1993; Davis et al., 1989; Davis et al., 1992; Faltynek et al., 1995; and Sawutz et al., 1996).

In summary, structure-based design has produced a series of hydroxynaphthalene $pp60^{c-src}$ non-peptide inhibitors that do not compete with ATP. Results with compounds from this series in cell-based assays, as well as detailed kinetic studies under various assay conditions, will be reported in due course. An extension of these design concepts from the naphthalene scaffold to an indole scaffold is reported in the following Example.

Example 4

Design, Synthesis and Activity of Non-ATP Competitive Hydroxyindole Derivative Inhibitors of $pp60^{c-Src}$ Tyrosine Kinase In the preceding example, the structure-based design of a series of $pp60^{c-src}$ inhibitors utilizing a naphthalene scaffold is described. These compounds were designed to bind in the peptide substrate site because of the potential for greater selectivity and efficacy in a cellular environment relative to the alternative ATP substrate site. This example presents an extension of these design concepts to a series of $pp60^{c-src}$ inhibitors based upon an indole scaffold. Once again the crystal structure of the autoinhibited insulin receptor PTK (IRTK) was used to carry out qualitative molecular modeling studies, except in this case an indole ring was superimposed upon the IRTK Tyr 1,162. This superimposition indicated that the indole NH can mimic the Tyr 1,162 NH, that a carbonyl should be placed at the 2-position, and a hydroxyl group at the 5 position to mimic the Tyr 1,162 carbonyl and OH, respectively (Scheme 1).

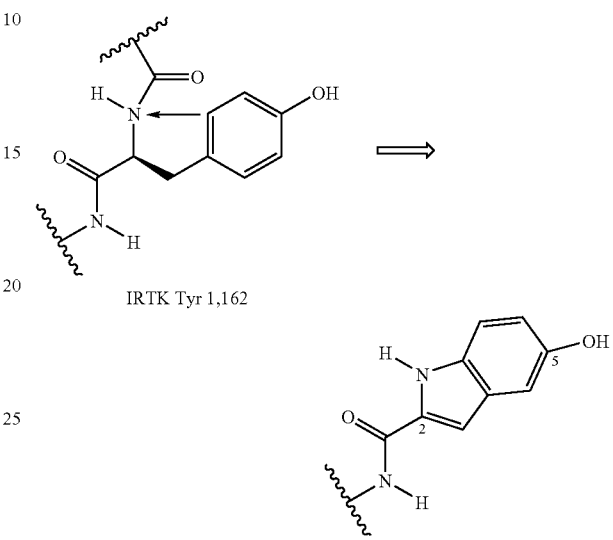

IRTK Tyr 1,162

The conceptual cyclization of Tyr 1,162 to the smaller 5-membered ring of an indole illustrated in Scheme 1, relative to a 6-membered ring in the case of the naphthalene scaffold (Karni et al., 1999), results in a movement of the optimal positioning of the OH from carbon 6 in the naphthalene scaffold to carbon 5 in the indole scaffold.

The indole amide derivatives containing hydroxy phenyl/benzyl side chains 2d-f, 2j-l (Table 5), respectively, were selected based upon the increase in $pp60^{c-src}$ inhibitor potency observed for the analogous naphthalene-based hydroxy phenyl amides reported in the previous example. The corresponding methyl ethers 2a-c,g-i,v are precursors in the synthesis. The additional analogs shown in Table 5 were prepared to begin expanding the range of side chains beyond the hydroxy/methoxy groups that have now been extensively probed with both the indole and naphthalene scaffolds.

The indole amides containing only hydroxy or methoxy side chains were synthesized as illustrated:

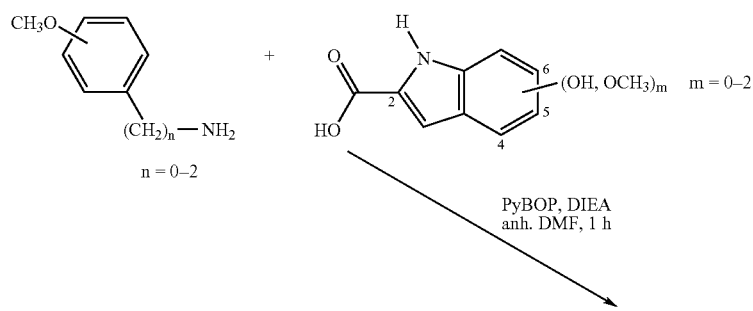

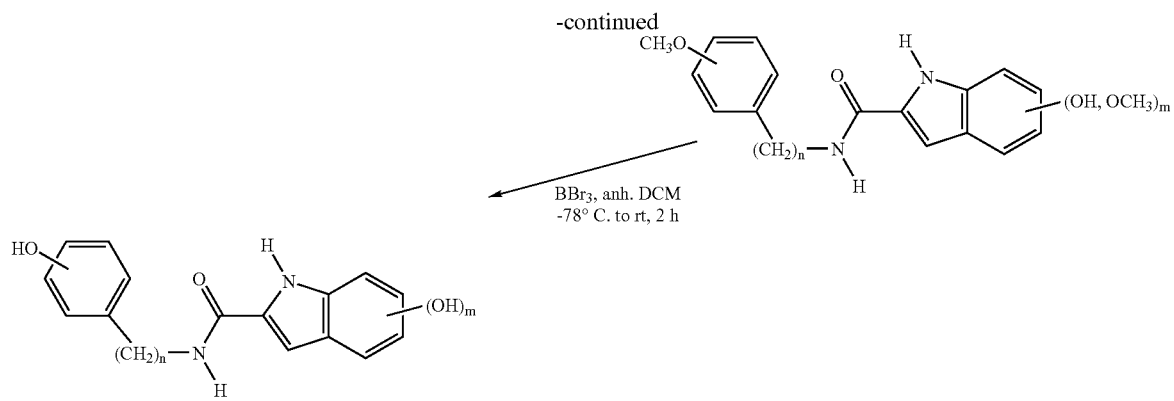

The 2-indolecarboxylic acid derivative, the methoxyphenyl amine (1.1 eq, Aldrich, Lancaster or Fluka), and the coupling reagent PyBOP (benzotriazol-1-yloxy)tripyrrolidino-phosphonium-hexafluorophosphate) (1 eq, Fluka) were dissolved in anhydrous DMF. The solution was cooled to 0° C. under argon and then diisopropylethylamine (DIEA, 3 eq) was added. The reaction was stirred at 0° C. for 1 m followed by 1 hour at room temperature. After workup the residue was purified by silica gel chromatography.

The methyl ethers were cleaved with boron tribromide (1 M in DCM, Aldrich) when desired. The indole amide methyl ether was suspended in dry DCM and cooled to −78° C. under argon. One equivalent of BBr$_3$ was added for each heteroatom in the starting material plus one excess equivalent. The resulting dark red solution was stirred at −78° for 30 m and then at room temperature for 1-2 hours. The reaction was quenched with water (10 minutes) before workup.

TABLE 5 pp60[c-src] INHIBITORY ACTIVITY OF HYDROXYINDOLE DERIVATIVES.[a,b,c]

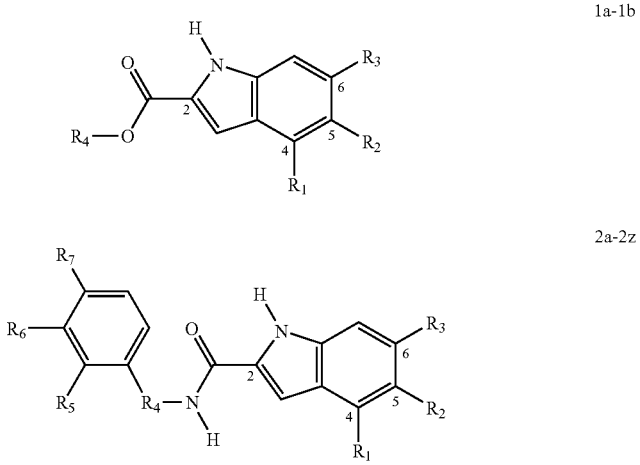

| Cmpd | R$_1$ | R$_2$ | R$_3$ | R$_4$ | R$_5$ | R$_6$ | R$_7$ | % Inhibition at 100 μM (std. dev.) |
|---|---|---|---|---|---|---|---|---|
| 1a | H | OH | H | CH$_3$ | N/A | N/A | N/A | 40 (+/−5) [at 500 μM] |
| 1b | H | OH | OH | CH$_2$CH$_2$ | N/A | N/A | N/A | 28 (+/−3) |
| 2a | H | OH | H | — | OCH$_3$ | H | H | 3 (+/−1) |
| 2b | H | OH | H | — | H | OCH$_3$ | H | 21 (+/−2) |
| 2c | H | OH | H | — | H | H | OCH$_3$ | 39 (+/−9) |
| 2d | H | OH | H | — | OH | H | H | 43 (+/−1) |
| 2e | H | OH | H | — | H | OH | H | 30 (+/−6) |
| 2f | H | OH | H | — | H | H | OH | 45 (+/−3) |
| 2g | H | OH | H | CH$_2$ | OCH$_3$ | H | H | 21 (+/−5) |
| 2h | H | OH | H | CH$_2$ | H | OCH$_3$ | H | 7 (+/−6) |
| 2i | H | OH | H | CH$_2$ | H | H | OCH$_3$ | 18 (+/−4) |
| 2j | H | OH | H | CH$_2$ | OH | H | H | 24 (+/−3) |
| 2k | H | OH | H | CH$_2$ | H | OH | H | 74 (+/−2) |

TABLE 5-continued pp60[c-src] INHIBITORY ACTIVITY OF HYDROXYINDOLE DERIVATIVES.[a,b,c]

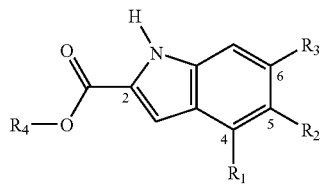

1a-1b

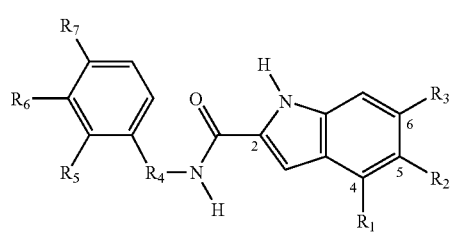

2a-2z

| Cmpd | $R_1$ | $R_2$ | $R_3$ | $R_4$ | $R_5$ | $R_6$ | $R_7$ | % Inhibition at 100 μM (std. dev.) |
|---|---|---|---|---|---|---|---|---|
| 2l | H | OH | H | $CH_2$ | H | H | OH | [$IC_{50}$ = 38 μM]<br>54 (+/−2) |
| 2m | H | OH | H | $CH_2CH_2$ | H | H | OH | 21 (+/−7) |
| 2n | H | OH | H | $CH_2$ | H | H | $CO_2H$ | not active |
| 2o | H | OH | H | $CH_2$ | H | H | $CO_2CH_3$ | 11 (+/−4) |
| 2p | H | OH | H | — | H | H | $CH_2CO_2H$ | 7(+/−6) |
| 2q | H | OH | H | — | H | H | $CH_2CO_2CH_3$ | 32 (+/−7) |
| 2r | H | OH | H | — | H | F | H | 21 (−/−7) |
| 2s | H | OH | H | $CH_2$ | H | F | H | 57 (+/−6) |
| 2t | H | OH | OH | $CH_2$ | H | OH | H | 26 (+/−2) |
| 2u | H | H | OH | $CH_2$ | H | OH | H | 56 (+/−6) |
| 2v | H | H | H | $CH_2$ | H | H | $OCH_3$ | 4 (+/−4) |
| 2w | H | H | H | $CH_2$ | H | H | OH | 36 (+/−4) |
| 2x | OH | H | H | $CH_2$ | H | OH | H | 60 (+/−3) |
| 2y | H | OH | H | $CH(CH_3)$ R | H | OH | H | 15 (+/−3) |
| 2z | H | OH | H | $CH(CH_3)$ S | H | OH | H | 13 (+/−7) |

[a]All compounds were tested as described in the preceding example.[5]
[b]All compounds were characterized by proton NMR, FAB(+) MS and are pure by TLC.
[c]N/A = Not applicable.

Using this synthetic route, the series of 5-hydroxyindole amide inhibitors 2a-m,y,z were prepared from 5-hydroxy-2-indolecarboxylic acid. The 4- and 6-hydroxyindole amides (2x,u, respectively) were synthesized from methyl 4-methoxy-2-indolecarboxylate and methyl 6-methoxy-2-indolecarboxylate, respectively. The 5,6-dihydroxyindole amide 2t was prepared from ethyl 5,6-dimethoxyindole-2-carboxylate. Sonication of the esters in 1 N NaOH for 1 hour provided the corresponding carboxylic acids for coupling. The des-hydroxy indole amides 2v,w were synthesized from indole-2-carboxylic acid. All of the indole starting materials were commercially available (Aldrich or Lancaster).

The fluoro inhibitors 2r,s were likewise prepared from the corresponding fluorophenyl amines (Aldrich). The inhibitors containing esters or carboxylic acids on the amide side chain, 2n-q, were prepared from the corresponding amino carboxylic acids (Aldrich). The side chain carboxylic acid was first protected as a methyl ester (anh. MeOH pre-saturated with HCl, reflux, 1d), followed by PyBOP coupling (as above), then saponification back to the carboxylic acid when desired.

The methyl ester 1a was prepared by refluxing a solution of the carboxylic acid overnight in anhydrous methanol pre-saturated with HCl gas. The ethyl ester 1b was prepared by $BBr_3$ deprotection of ethyl 5,6-dimethoxyindole-2-carboxylate as above. All of the inhibitors listed in Table 5 were purified by silica gel chromatography.

As in Marsilje 2000, the rank order activity of this series of pp60[c-src] inhibitors was first determined at a constant inhibitor concentration (Table 5). The same inhibitor concentration (100 μM) was used for the current indole series of inhibitors, the previous naphthalene series of inhibitors, and five non-ATP competitive literature PTK inhibitors (see preceding Example). This allowed an efficient rank order comparison of 59 compounds in total under identical assay conditions.

The modeling studies predicted that a hydroxy group at carbon 5 of the indole scaffold would be optimal. Comparison of the 5-hydroxy indole inhibitor 2k (74%) with the analogous 6-hydroxy indole inhibitor 2u (56%) and 4-hydroxy indole inhibitor 2x (60%) confirms this prediction, although the preference is not strong. The prediction that a hydroxy group at carbon 5 will improve the activity (relative to no hydroxy group) is confirmed by comparing the 5-hydroxy indole inhibitor 2l (54%) with the corresponding des-hydroxy inhibitor 2w (36%).

Extending the indole inhibitors as aryl amides at carbon 2 improved potency, as expected based upon the previous naphthalene inhibitors. For example, the meta-hydroxybenzyl amide indole 2k gives 74% inhibition at 100 μM whereas the analogous methyl ester 1a gives only 40% inhibition at 500 μM. Interestingly, comparing the 5,6-dihydroxy ethyl ester 1b (28%) to the corresponding aryl amide 2t (26%) shows that the simultaneous presence of the second hydroxy at carbon 6 prevents the potency enhancement normally provided by the otherwise preferred meta-hydroxybenzyl amide side chain. This amide side chain was the best of the current series when the 5-hydroxyl group is present alone (2k, 74%) and still gave good inhibition when a 6-hydroxy group was present alone (2u, 56%). Also, the simultaneous presence of two hydroxy groups at carbons 5 and 6 seems well tolerated in the absence of an amide side chain (1b vs. 1a and 2e). This data suggests that a change in the binding orientation of the indole scaffold may have occurred due to the presence of the second hydroxy group and that a different amide side chain may now be preferred. The optimal combination of side chains at carbons 4-7 (including functional group replacements for hydroxy groups (Lai et al., 1999)) and amide side chains is currently under investigation.

In general, the indole scaffold structure-activity-relationships ("SARs") revealed by the data in Table 5 parallels that reported in the preceding example for the naphthalene scaffold. In both cases positioning a hydroxy group on the scaffold analogous to the Tyr 1,162 OH, as identified by modeling studies, provided the highest potency. Moving this hydroxy group to one of the adjacent carbons reduced the potency, but not dramatically, in both cases. Extending both scaffolds with aryl amides at the position identified by the modeling studies to mimic the Tyr 1,162 peptide bond improved the potency. With both scaffolds, substitution of a methoxy group for the hydroxy groups on the amide side chain usually reduced potency, and did so to a greater extent with the longer benzylamide side chain (e.g. 2k, 74% vs. 2h, 7% compared to 2e, 30% vs. 2b, 21%). The major difference in the SARs for these two scaffolds is that the 5-hydroxyindole scaffold prefers the longer m-hydroxybenzyl amide side chain (2k, 74% vs. 2e, 30%) whereas the analogous 3,6-dihydroxynaphthalene scaffold prefers the shorter amide side chain derived from m-hydroxyaniline. The 5-hydroxyindole scaffold showed essentially no preference for the position of the hydroxyl group on the shorter amide side chain (2d-f) whereas with the longer hydroxybenzyl amide side chain a significant preference for the meta position was observed (2j-l). In the case of the 3,6-dihydroxynaphthalene scaffold the opposite was observed.

Additional molecular modeling studies were carried out to further probe the preference for a longer amide side chain with the indole scaffold. The most active naphthalene inhibitor 3 from the previous report was used as a template upon which the analogous indole inhibitor 2e and the homologated indole inhibitor 2k were superimposed. The three most important side chain functional groups in naphthalene inhibitor 3 are considered to be the 6-hydroxy group (H-bond donor and acceptor), the hydrogen from the 3-hydroxy group (H-bond donor), and the side chain hydroxy group (H-bond acceptor) based upon the rational design and SAR for both series of inhibitors. This three point pharmacophore model is identified in both series by asterisks in Scheme 3.

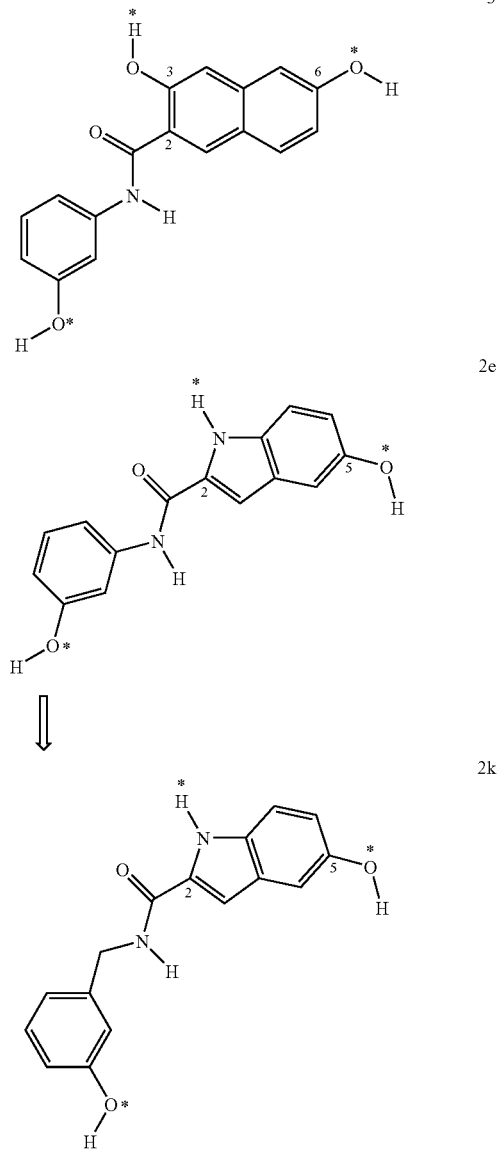

The "multifit" energy minimization and "fit atoms" facilities within SYBYL™ (6.4, Tripos, St. Louis) were used in sequence to superimpose 2e and 2k onto 3. This overall fitting process was carried out with spring constants (multifit) and weights (fit atoms) chosen such that the highest emphasis was on optimally superimposing the scaffold pharmacophore O's and H's (100), followed by the side chain O's (10) and then the intervening amide bond (1). The "multifit" process adjusted the conformations for maximum pharmacophore fit, the subsequent minimization produced the nearest local minimum energy conformations and finally the "fit atoms" process produced the best pharmacophore superimposition of these minimized conformations. As expected, the scaffold pharmacophore O's and H's of both 2e and 2k superimposed closely and similarly upon the corresponding atoms in 3 (all within ca. 0.50 Å). However, the side chain pharmacophore O's of 2e and 2k differed significantly in their superimposition on the corresponding O of 3, with displacements of 1.8 Å vs. only 0.08 Å respectively. This close fit of the three key pharmacophore sites between 2k and 3 provides a rationalization for their potency differing by only a factor of 2.4 ($IC_{50}$'s 38 μM vs. 16 μM, respectively).

Extending the amide side chain by another carbon atom reduced the activity (2m, 21% vs. 21, 54%). Adding a methyl group to the benzylic carbon of 2k, in either stereochemistry, greatly reduced the activity (2y, 15% & 2z, 13% vs. 2k, 74%). Replacing the side chain hydroxy group (in the para position) with a carboxylate anion (2n, 0% vs. 21, 54% and 2p, 7% vs. 2f, 45%) reduced the activity whereas the corresponding methyl esters (2o, 11% & 2q, 32%, respectively) showed a smaller loss of potency. Importantly, replacing the side chain hydroxy group with a fluorine maintained much of the potency (2s, 57% vs. 2k, 74% and 2r, 21% vs. 2e, 30%). Consequently, the fluoro analog 2s has only one hydroxy group left for potential Phase II metabolism (e.g. glucuronide formation), and this remaining hydroxy group is a current target for replacement (Lai et al., 1998).

Using the same method as in the preceding example (Marsilje, 2000), the most potent inhibitor from the current indole series (2k) was analyzed for ATP competition by monitoring the % inhibition at increasing [ATP] while holding the inhibitor concentration constant. Since the [ATP] had little effect on the % inhibition (the % inhibition was 46% and 41% with 2k at 45 μM and [ATP] at 200 μM or 1,000 μM, respectively), 2k is non-competitive with respect to ATP under these assay conditions.

In summary, an indole scaffold has been designed, and an initial SAR carried out, for the development of non-ATP competitive $pp60^{c-src}$ inhibitors. The potency of the best indole-based inhibitor from the current series was found to be close to that of the best naphthalene-based inhibitor. The % inhibition was 46% and 41% with 2k at 45 μM and [ATP] at 200 μM or 1,000 μM, respectively.

Example 5

Synthesis of Additional Indole Derivative Protein Kinase Inhibitors

The following results show the synthesis and testing of indole derived protein kinase inhibitors. Four reaction schemes are provided and separately followed by experimental details for the preparation of the final product of each of these reaction schemes. These final products are examples of indole-base tyrosine kinase inhibitors wherein the synthesis with preferred R groups is illustrated (boronic acid, Scheme 1; OH, Scheme 2; an aliphatic amide extension, Scheme 3; and a phosphonic acid Scheme 4).

Scheme 1

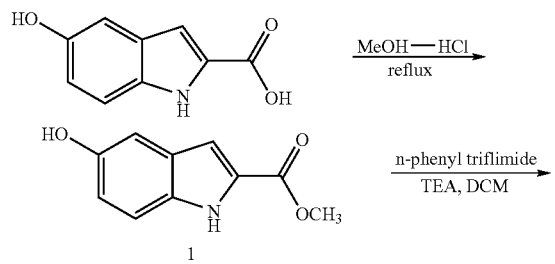

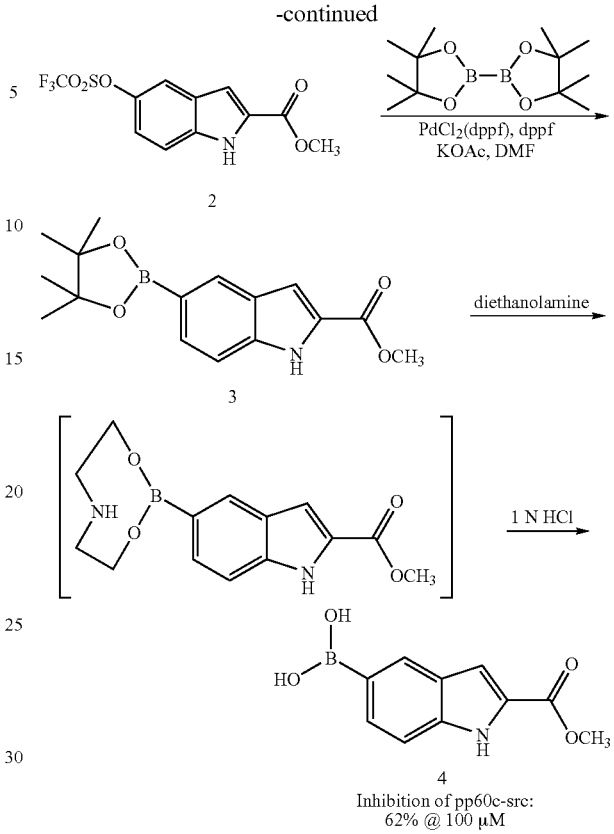

Methyl 5-hydroxy-2-indolecarboxylate (1)

Dissolved 3.50 g 5-hydroxy-2-indolecarboxylic acid in anh. MeOH presaturated with HCl gas. Refluxed for 48 hours. Concentrated in vacuo and triturated with AcCN×3 to remove residual acid. Filtered through silica plug with EtOAc to remove baseline contamination. Recovered 4.32 g (quant. yield) TLC $R_f$=0.78 (EtOAc) $^1$H NMR (DMSO-$d_6$): 3.82 (s, 3H), 6.78 (d, J=8.8 Hz, 1H), 6.88 (s, 1H), 6.93 (s, 1H), 7.23 (d, J=8.8 Hz, 1H), 8.90 (s, 1H) 11.62 (s, 1H) FAB(+) MS m/e 191.9 (M+1)

Methyl 5-[(trifluoromethyl)sulfonyloxy]indole-2-carboxylate (2)

Added 150 ml anh. DCM to 3.24 g (17 mmol) methyl 5-hydroxy-2-indolecarboxylate (1) and 6.67 g (18.7 mm) n-phenyl trifluoromethane sulfonamide at 0° C. Added 2.6 ml triethylamine dropwise at which point clear yellow solution formed. Stirred at 0° C. for 1 hour. Warmed to room temperature and stirred for 2 hours. Concentrated in vacuo and purified through silica gel column (1/1 EtOAc/hexanes). Recovered 4.69 g (86%). TLC $R_f$=0.63 (1/1 EtOAc/hexanes). HPLC $R_f$=20.879 1H NMR (DMSO-$d_6$): 3.87 (s, 3H), 7.25 (s, 1H), 7.31 (d, J=9.2 Hz, 1H), 7.55 (d, J=9.2 Hz, 1H), 7.80 (s, 1H), 12.34 s, 1H) FAB(+) MS m/e 323.1 (M+1).

Methyl 5-methylindole-2-carboxylate, 4,4,5,5-tetramethyl-1,3,2-dioxaborolanemethyl (3)

500 mg 1.55 mmol methyl 5-[(trifluoromethyl)sulfonyloxy]indole-2-carboxylate (2), 37.9 mg (0.05 mmol) $PdCl_2$ (dppf), 432 mg (1.7 mmol) bispinacolatodiboron, 454.8 mg (4.65 mmol) potassium acetate, and 25.7 mg (0.05 mmol) dppf were added to a flask and vacuum dried at 40° C. for 2 hours. Added 20 ml anh dioxane and heated to 80° C. overnight. Reaction turned black as Pd black precipitated out. Filtered off catalyst and ran silica plug to remove baseline impurities. TLC $R_f$=0.51 (1/4 EtOAc/Hexane) Crude product was taken through to next reaction.

Methyl 5-boronyl indole-2-carboxylate (4)

391.2 mg (1.3 mmol) methyl 5-methylindole-2-carboxylate, 4,4,5,5-tetramethyl-1,3,2-dioxaborolanemethyl (3) was dissolved in EtOAc. 0.25 ml (2.6 mmol) diethanolamine was added, and the reaction was stirred at room temperature overnight. The white ppt which formed was filtered and sonicated in 1 N HCl. The resulting white ppt was filtered, dissolved in MeOH, and concentrated in vacuo. Recovered 36.6 mg (13%). HPLC $R_f$=13.912, $^1$H NMR (DMSO-$d_6$): 3.85 (s, 3H), 7.15 s, (1H), 7.36 (d, J=8.4 Hz, 1H), 7.67 (d, J=8.4 Hz, 1H), 7.87 (s, 1H), 8.14 (s, 1H), 11.91 (s, 1H).

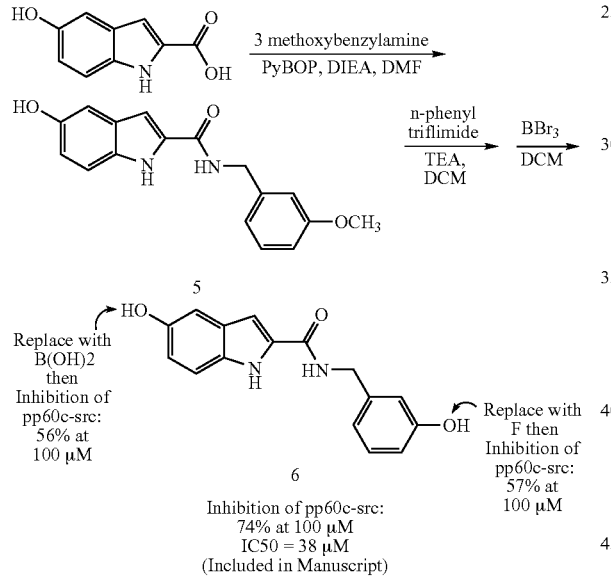

(5-hydroxyindol-2-yl)-N-[(3-methoxyphenyl)methyl]carboxyamide (5)

Dissolved 2.00 g (11.3 mmol) 5-hydroxy-2-indolecarboxylic acid, 1.6 ml (12.4 mmol) 3 methoxybenzylamine, and 5.87 g (11.3 mmol) PyBOP in 10 ml anh. DMF. Cooled to 0° C. and added 5.9 ml (33.9 mmol) DIEA. Stirred for 5 minutes at 0° C. and allowed to warm to room temperature for 1 hour. Recovered 2.83 g (85% yield) TLC $R_f$=0.34 (1/1 EtOAc/hexanes) $^1$H NMR (DMSO-$d_6$): 3.70 (s, 3H), 4.43 (d, J=4.4 Hz, 2H) 6.69 (d, J=8.8 Hz, 1H), 6.78 (d, J=7.7 Hz, 1H), 6.83 (s, 1H), 6.86 (s, 1H), 6.94 (s, 1H), 7.20 (m, 3H), 8.92 (t, J=4.4 Hz, 1H), 11.36 (s, 1H) FAB(+) MS m/e 297.3 (M+1)

(5-hydroxyindol-2-yl)-N-[(3-hydroxyphenyl)methyl]carboxyamide (6)

Added 20 ml anh. DCM to 200 mg (0.67 mmol) (5-hydroxyindol-2-yl)-N-[(3-methoxyphenyl)methyl]carboxyamide (5) and cooled to −78° C. under argon. Added 4.0 ml (4.0 mmol, 6 eq) BBr$_3$. Held at −78° C. for 5 minutes and warmed to rt. After 90 minutes at room temperature, quenched with H$_2$O and stirred for 10 minutes. Diluted reaction mix with EtOAc and washed with NaHCO$_3$ and brine. Dried organic layer over MgSO$_4$ and concentrated in vacuo. Ran through silica plug to remove baseline contamination. Recovered X mg. (80% yield.) TLC $R_f$=0.21 (1/1 EtOAc/hexanes). $^1$H NMR (DMSO-$d_6$): 4.38 (d, J=4.8 Hz, 2H), 6.59 (d, J=8.8 Hz, 1H), 6.71 (m, 3H) 6.83 (d, J=1.8 Hz, 1H), 6.94 (s, 1H), 7.08 (dd, J=7.7 Hz, 1H), 7.19 (d, J=8.8 Hz, 1H), 8.84 (t, J=5.9 Hz, 1H), 11.28, (s, 1H). FAB(+) MS m/e 283.2 (M+1)

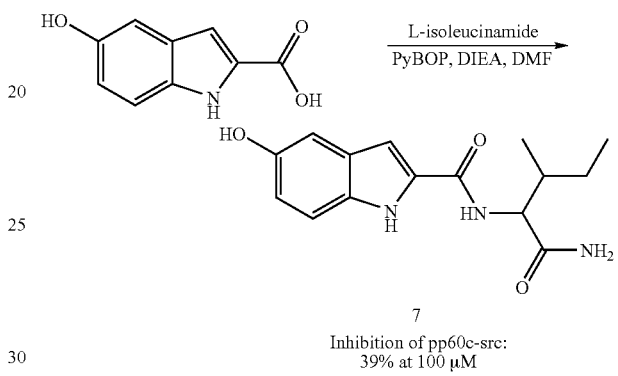

N-(1-carbamoyl-2-methylbutyl)(5-hydroxyindol-2-yl)carboxyamide (7)

100 mg (0.56 mmol) 5-hydroxy-2-indolecarboxylic acid, 103.4 mg (0.62 mmol, 1.1 eq) L-isoleucinamide, and 291 mg (0.56 mmol, 1 eq) PyBOP were all dissolved in 1 ml anh DMF. The solution was cooled to 0° C. and 0.3 ml (1.68 mmol, 3 eq) DIEA was added. The reaction mixture was stirred for 1 minute at 0° C. and at room temperature for 1 hour. The reaction was then diluted with EtOAc and washed with 1 N HCl×3 and sated NaHCO3×3. The organic layer was dried over MgSO4, and concentrated in vacuo to give 166.7 mg (91% yield.) TLC $R_f$=0.08 (1/1 EtOAc/hexanes). $^1$H NMR (DMSO-$d_6$): 0.83 (m, 6H), 1.15 (m, 2H), 1.68 (m, 1H), 1.83 (m, 1H), 4.29 (t, J=8.8 Hz, 1H), 6.69 (d, J=8.5 Hz, 1H), 6.83 (s, 1H), 7.01, (s, 1H), 7.06 (s, 1H), 7.19 (d, J=8.4 Hz, 1H), 7.48, (s, 1H), 8.00 (d, 9.2 Hz, 1H), 8.76 (s, 1H), 11.3, (s, 1H). FAB(+) MS m/e 290.1 (M+1)

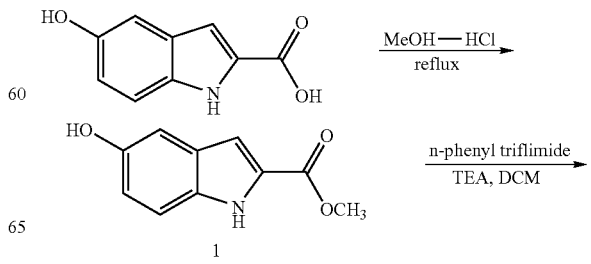

-continued

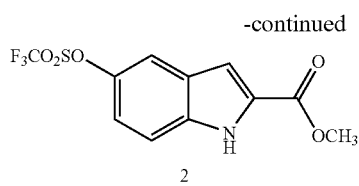

Example 6

Synthesis of Further Indole Derivative Protein Kinase Inhibitors

The synthesis of some further elaborated indole inhibitors is illustrated in below. These syntheses should result in compounds with greater potency against pp60c-Src and other tyrosine kinases. The methyl ester group can be subsequently converted into various amide derivatives to increase potency.

Scheme 1:

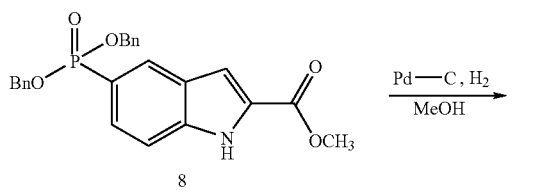

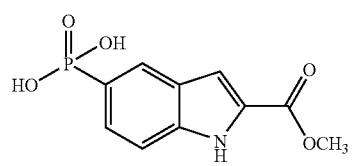
9
Inhibition of pp60c-src:
11% at 500 μM

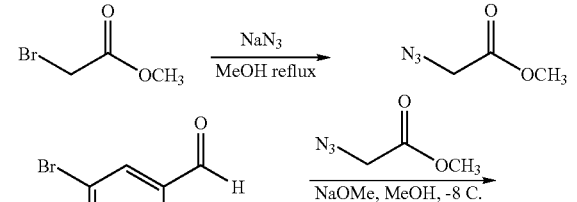

Methyl 5-dibenzylphosphorylindole-2-carboxylate (8)

200 mg (0.62 mmol) methyl 5-[(trifluoromethyl)sulfonyloxy]indole-2-carboxylate (2), 195.8 mg (0.74 mmol, 1.2 eq) dibenzylphosphite, 0.14 ml (0.81 mmol, 1.3 eq) DIEA, and 35.7 mg (0.03 mmol, 5 mol %) Pd(PPh$_3$)$_4$ were all dissolved in anh AcCN under argon. The reaction mix was heated to 80° C. overnight. The solvent was removed under reduced pressure, and the title compound was isolated by silica gel chromatography. 130 mg (50% yield). TLC R$_f$=0.28 (1/1 EtOAc/hexanes) $^1$H NMR (DMSO-d$_6$): 3.85 (s, 3H), 4.98-5.01 (m, 4H), 7.28-7.32 (m, 11H), 7.53-7.55 (m, 2H), 8.17 (d, J=14.6 Hz, 1H) $^{31}$P NMR (DMSO-d$_6$): 23.89.

Methyl 5-phosphonolindole-2-carboxylate

Methyl 5-dibenzylphosphorylindole-2-carboxylate (8) (125 mg) was dissolved in 10 ml MeOH. 20 mg Pd—C was added and the mixture was hydrogenated in a Parr apparatus overnight. Filtered off catalyst and removed solvent under reduced pressure. Obtained 72.5 mg (73% yield). TLC R$_f$=baseline in EtOAc. $^1$H NMR (DMSO-d$_6$): 3.84 (s, 3H), 7.24 (s, 1H), 7.44-7.49 (m, 2H), 8.01 (d, J=14.3 Hz, 1H) 12.11 (s, 1H) $^{31}$P NMR (DMSO-d$_6$): 17.22.

The ester compounds in this example could be increased in potency by converting the ester to an amide and/or adding additional specificity elements.

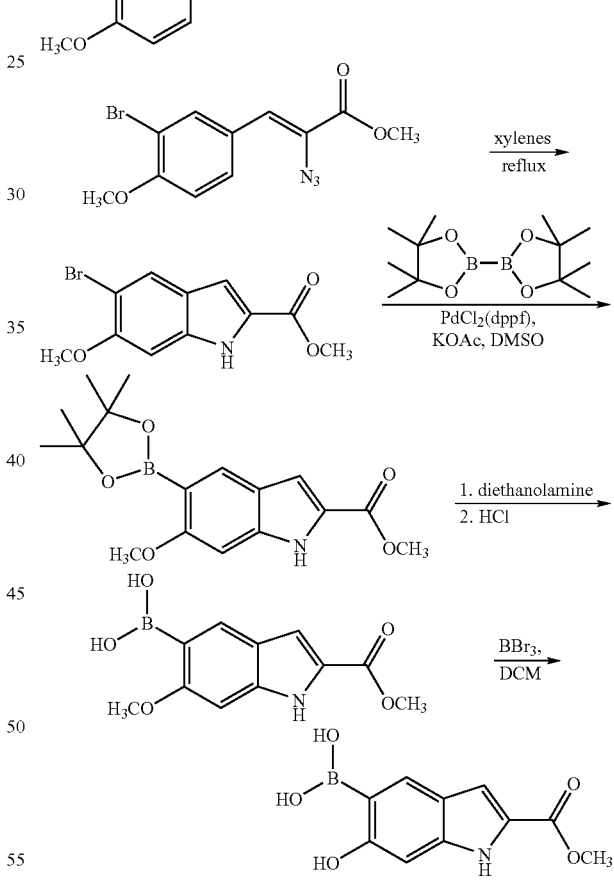

Scheme 2:

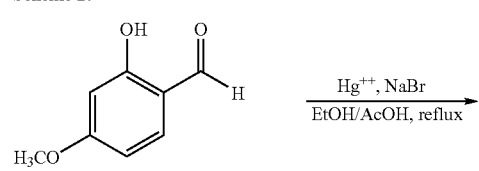

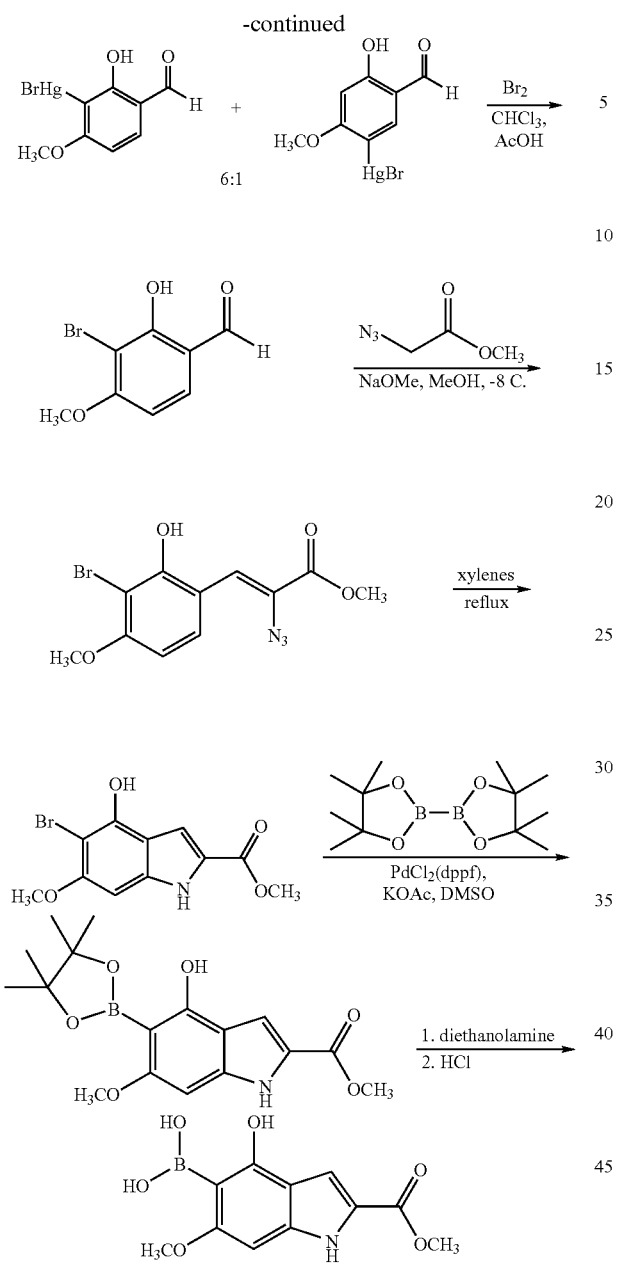

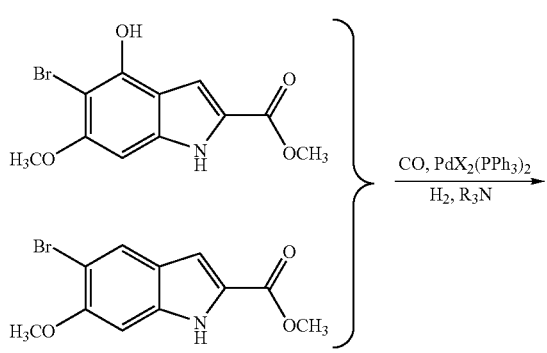

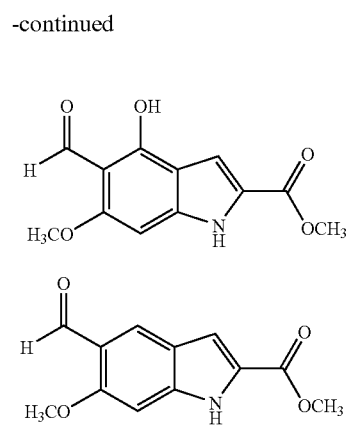

Example 7

Toxicity of Src inhibitors

There is considerable literature support for targeting pp60$^{c-src}$ (Src) as a broadly useful approach to cancer therapy without resulting in serious toxicity. For example, tumors that display enhanced EGF receptor PTK signaling, or overexpress the related Her-2/neu receptor, have constitutively activated Src and enhanced tumor invasiveness. Inhibition of Src in these cells induces growth arrest, triggers apoptosis, and reverses the transformed phenotype (Karni et al., 1999). It is known that abnormally elevated Src activity allows transformed cells to grow in an anchorage-independent fashion. This is apparently caused by the fact that extracellular matrix signaling elevates Src activity in the FAK/Src pathway, in a coordinated fashion with mitogenic signaling, and thereby blocks an apoptotic mechanism which would normally have been activated. Consequently FAK/Src inhibition in tumor cells may induce apoptosis because the apoptotic mechanism which would have normally become activated upon breaking free from the extracellular matrix would be induced (Hisano et al., 1997). Additionally, reduced VEGF mRNA expression was noted upon Src inhibition and tumors derived from these Src-inhibited cell lines showed reduced angiogenic development (Ellis et al., 1998).

The issue of potential toxicity of Src inhibition has been addressed with very promising results. For example, a knockout of the Src gene in mice led to only one defect, namely osteoclasts that fail to form ruffled borders and consequently do not resorb bone. However, the osteoclast bone resorb function was rescued in these mice by inserting a kinase defective Src gene (Schwartzberg et al., 1997). This suggested that Src kinase activity can be inhibited in vivo without triggering the only known toxicity because the presence of the Src protein is apparently sufficient to recruit and activate other PTKs (which are essential for maintaining osteoclast function) in an osteoclast essential signaling complex.

Src has been proposed to be a "universal" target for cancer therapy since it has been found to be overactivated in a growing number of human tumors, in addition to those noted above (Levitzki, 1996). The potential benefits of Src inhibition for cancer therapy appear to be four-fold based upon the cited, and additional, literature. They are: 1) Inhibition of uncontrolled cell growth caused by autocrine growth factor loop effects, etc. 2) Inhibition of metastasis due to triggering apoptosis upon breaking free from the cell matrix. 3) Inhibition of tumor angiogenesis via reduced VEGF levels. 4) Low toxicity.

Figure 2E:
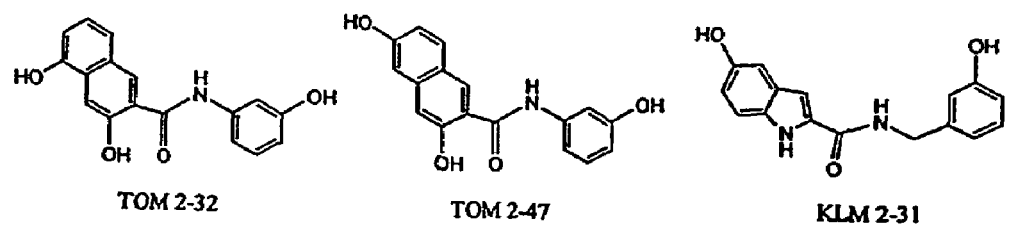
FIG. 2E provides the structures of the Src inhibitors tested.

The initial non-peptide Src inhibitors have also shown very encouraging results in four different series of cell culture assays. 1) In the NIH 60-tumor cell panel assay, broad activity (as one would expect for a Src inhibitor) was seen against the tumor cell lines, including the prostate lines. For example, three of the inhibitors gave the following growth inhibition $IC_{50}$'s against the NIH prostate cancer cell lines: TOM 2-32 (PC-3, 15 µM; DU-145, 38 µM), TOM 2-47 (PC-3, 19 µM), KLM 2-31 (PC-3, 39 µM; DU-145, >100 µM). 2) In the v-Src transformed normal rat kidney cell line (LA25) TOM 2-47 and TOM 2-32 specifically blocked the v-Src induced cell growth without inhibiting the normal growth of the parent non-transformed cells. This result showed that the inhibitors do not affect normal cells but are effective in blocking Src induced cell transformation. 3) The Src inhibitors were compared to the cancer drugs etoposide, taxol, doxorubicin, and cisplatin in ovarian tumors from three different patients and an abdominal carcinoma from another patient. In all cases, the Src inhibitors were at least as effective, and typically more effective, than the known cancer drugs, with full efficacy seen at the lowest dose tested (3 µM). As a representative example, a comparison of taxol and doxorubicin (they were more effective than etoposide and cisplatin in this particular tumor cell culture) with the three Src inhibitors mentioned above (structures shown in FIG. 2E) utilizing ovarian tumor cells from tumor N015 is shown in FIG. 2A. 4) The Src inhibitors were also tested for inhibition of normal human fibroblast cell growth and found no inhibition of normal cell growth (both subconfluent and confluent; some enhanced growth was observed instead), indicating that these inhibitors are not toxic to normal cells even at a 10-fold higher concentration. An example of his data is given in FIG. 2B. 5) Two of the Src inhibitors were also tested for inhibition of ts v-Src stimulated LA25 cell growth. The results are shown in FIG. 2C. These results show that the tested compounds inhibit Src stimulated cell growth. 6) Two of the Src inhibitors were also tested for inhibition of normal rat kidney cell growth. The results are shown in FIG. 2D and illustrate that the inhibitors are cytoprotective for normal cells.

Overall, the cell data obtained thus far shows what one might expect for Src inhibitors, i.e. broad activity against many cancer cell lines with little or no normal cell toxicity.

The preliminary Src inhibitors are lead structures from which it is possible to design more potent and selective inhibitors. In addition to utilizing the tyrosine kinase crystal structures, molecular modeling studies can be carried out with the natural product tyrosine kinase inhibitor damnacanthal (Faltynek et al., 1995) to investigate its peptide-competitive binding mode. These additional modeling studies enable one to design further analogs of Src inhibitors wherein the key pharmacophore elements of damnacanthal are incorporated into the new inhibitors. Their syntheses will be undertaken and the isolated Src testing done as reported (Marsilje 2000).

Example 8

Development of Src PTK Inhibitors for Treatment of Malignant Prostate Cancer

Prostate cancer cells have been reported to have both an over expression of paxillin and p130cas as well as being hyperphosphorylated (Tremblay et al., 1996) and may thus be a prime target for Src inhibitors. Prostate cancer is the most frequent malignancy and the second leading cause of cancer mortality among men. When clinically localized, it is most effectively treated by surgery or radiation therapy (Dorkin et al., 1997). For advanced disease, androgen suppression has been a mainstay of therapy for several decades and is known to cause cessation of cellular growth and stimulation of apoptosis in androgen-responsive prostate cancer cells (Dorkin et al., 1997). However, because prostate cancer is composed of a heterogeneous cell population, disease progression and mortality ultimately results from the emergence of androgen-independent cells since there is no treatment for advanced prostate cancer (Abate-Shen et al, 2000). Identification of potent inhibitors of PTKs active against highly malignant prostate cancer would provide a valuable tool in the treatment of advanced disease.

Methodology

Apoptosis—Media from controls and drug treated cells was transferred to a 30 ml tube and kept on ice. Adherent cells were gently washed with PBS and trypsinized for 3 minutes at 37° C. Trypsinized cells were combined with floating cells and counted. Cells ($5 \times 10^5$) were transferred to a 15 ml conical tube and washed once with 5 ml cold PBS and resuspended with Annexin V-FITC in binding buffer for 15 minutes in the dark. Cells were then centrifuged, resuspended in binding buffer, and 10 µl of propidium iodide was added. Analysis was done by FACSCAN. Cells Annexin-labeled were considered apoptotic. Dead cells were labeled with propidium iodide and live cells were unlabeled. Results were confirmed by immunohistochemistry.

Western blotting analysis—Total proteins were isolated from ~$5 \times 10^6$ cells and lysed in 1 ml of lysing buffer [50 mM Tris-HCl, pH 8.0, 100 mM NaCl, 0.5% sodium dodecyl sulfate (SDS), 0.5% sodium deoxycholate, 0.5% Nonidet P40, 10 mM dithiothreitol, 1 mM PMSF and 0.4U aprotinin]. Protein concentrations were determined with a DC protein assay kit. Expression of tyrosine phosphorylated proteins was investigated by immunoblotting. Protein from the cell lysates (50 µg was subjected to a 10% SDS-polyacrylamide gel electrophoresis followed by transfer onto a 4.5-µm Trans-Blot Transfer Medium using a nitrocellulose membrane. The blots were incubated with the appropriate secondary antibody and developed using a chemiluminescence reagent kit. Westerns obtained for paxillin were obtained by using standard stripping and reprobing of the membrane with a new secondary antibody. Each blot is typical of multiple runs.

Toxicity Assay—The sulforhodamine assay is designed to measure cell viability in a 96-well plate format. Cells were counted and plated at a concentration of 50,000 cells/well in 0.1 mL of 10% FBS in RPCI 1640 media. Plates were grown for 2 days in order to allow cells to attach and were then treated with an increasing concentration of drug for 72 hours. The media was removed from the wells and the plates fixed for 1 hour with 10% trichloroacetic acid. The wells were washed with PBS and stained with 0.4% sulforhodamine B for 15 minutes. Unbound dye was then removed by washing the plates with a 1% acetic acid solution, and (protein) bound dye was extracted using 10 mM Tris. The absorbance was then measured in a multi-well plate reader at wavelength of 570 nm. Each point is the average of 12 points ±S.D. and each graph is representative of multiple analyses.

Results

Figure 4:
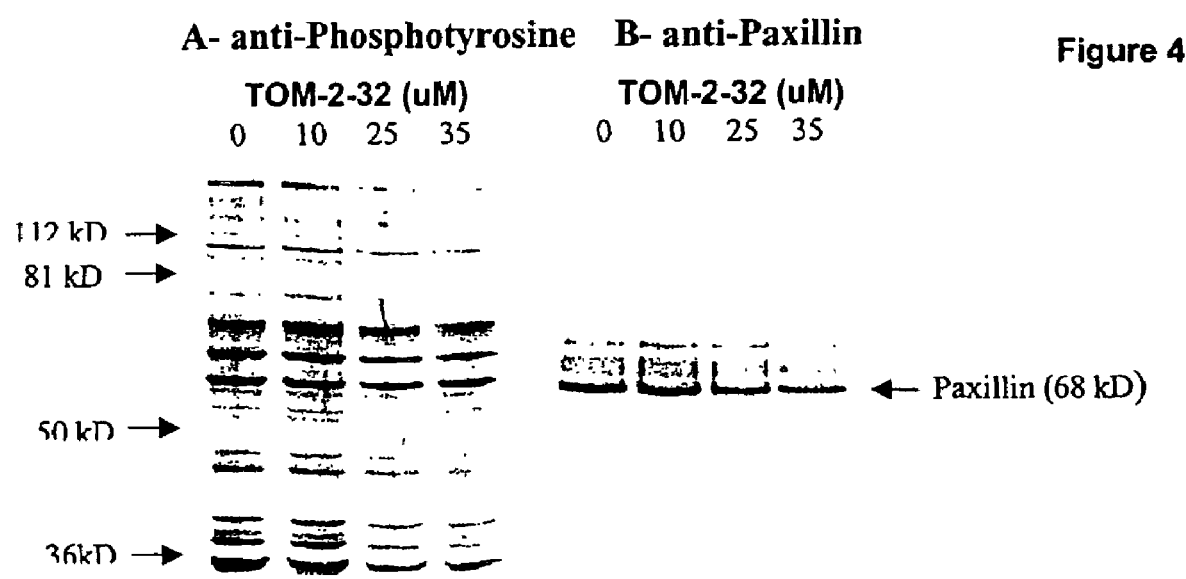
FIGS. 4A-B show Western analyses of proteins in malignant PC-3-LN prostate cancer cells treated with TOM 2-32 and detected using either anti-phosphotyrosine (FIG. 4A) or anti-paxillin (FIG. 4B) antibodies.

A considerable amount of data for Src inhibitors in highly malignant prostate cancer cells has been obtained. Representative toxicity data is shown (FIGS. 3A and B) following 72 hours of continuous exposure of each of four drugs and one inactive control. Determination of time course and apoptotic response has been performed primarily using TOM-2-32 (data not shown) and TOM 2-32 has been identified as the most active compound against highly malignant PC3-LN3 prostate cancer cells (FIGS. 3A and B). A second analysis using malignant LNCaP-LN cells showed nearly equal potency of the two compounds TOM2-32 and KLM2-31 (data not shown). KLM2-25 is a negative control and shows little activity in either cell line. The apoptotic response to this compound was unusual in that only a small percentage of cells (less than 5%) underwent apoptosis at any given time using an LD50 concentration. However, a 20% apoptotic rate was observed using an LD90 concentration for 92 hours (data not shown). Furthermore, TOM2-32 has been shown to be a good inhibitor of tyrosine kinase activity, although it lacks specificity for any single kinase target (FIG. 4A). Stripping the antibodies from the blotted membranes and re-blotting with a second antibody for either paxillin (FIG. 4B) or p130$^{cas}$ (not shown) has resulted in the successful identification of two of the affected protein bands in the Western blots. Re-probing with a second antibody provides unequivocal identification of individual protein bands due to the strict identification with the same molecular size labels. While TOM2-32 has since been characterized as having a short in vivo half-life, it has been most useful in developing a comprehensive strategy for evaluating these compounds in vitro.

Figure 5:
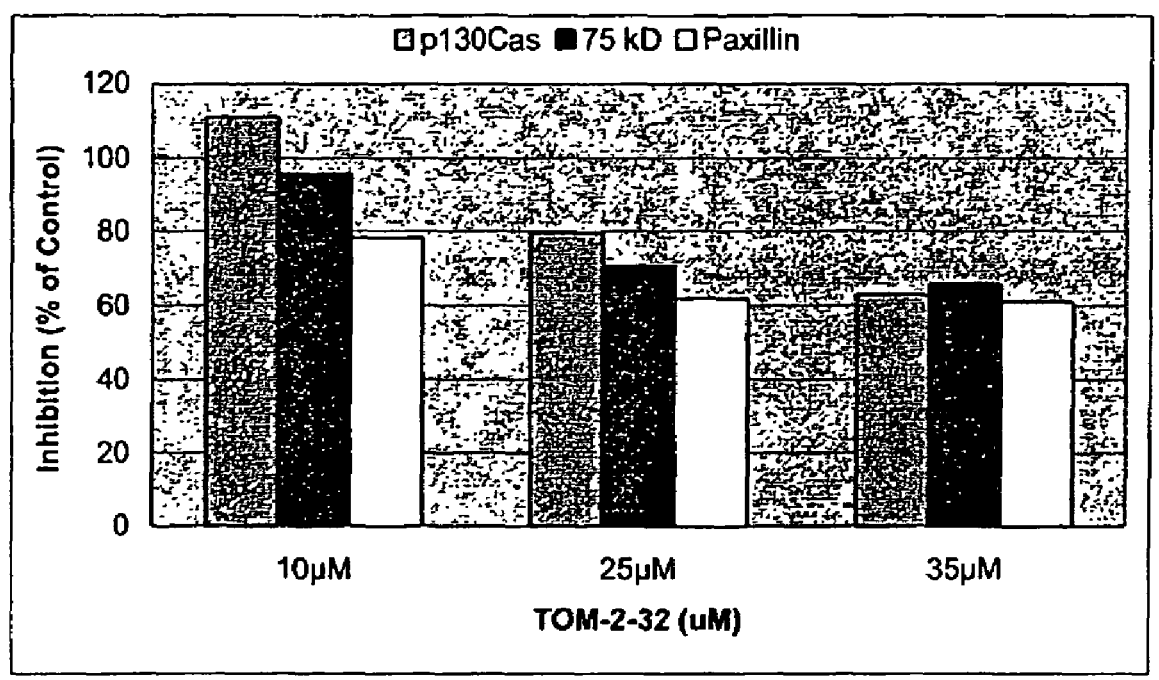
FIG. 5 is a graph showing the quantitation of two distinct phosphorylated substrates for focal adhesion complex (paxillin and p130 cas) and a third unknown substrate.

Subsequently, two distinct phosphorylated substrates for focal adhesion kinase (paxillin and p130 cas) and a third unknown substrate were quantitated. Quantitation was done by densitometry scanning of the film of the Western blots and is shown in FIG. 5. All three phophorylated substrates showed a dose-dependent inhibition of phosphorylation.

Example 9

Protection Against Noise-Induced Hearing Loss Using PTK Inhibitors

Chinchillas (N=8) were used in studies of noise-induced hearing loss. The animals' hearing sensitivity was measured using standard electrophysical techniques before the experimental manipulation. In particular, hearing thresholds were measured through evoked potentials from recording electrodes chronically implanted in the inferior colliculus, following standard laboratory procedures. Animals were anesthetized, the auditory bullae were opened, and the left and right cochleas were visualized. The round window leading to the scala tympani of the cochlea was used as the access point for drug application. Four animals were treated with 30 μl of 3 mM TOM 2-32, emulsified in DMSO, to 1000 mM of saline solution, which was placed on the round window of one ear, and a control solution of 3 mM DMSO to 1000 mM of saline solution, which was placed on the round window of the other ear. Five animals were treated with 30 μl of 3 mM CH-65, emulsified in DMSO, to 1000 mM of saline solution, which was placed on the round window of one ear, and a control solution of 3 mM DMSO to 1000 mM of saline solution, which was placed on the round window of the other ear (one animal was lost prior to the end of the experiments). In each case, the solution was allowed to set on the round window for 30 minutes, then the auditory bullae were closed. Subsequently, the animals were exposed to 4 kHz band noise at 105 dB SPL for four hours. Following the noise exposure, the animals' hearing was tested at day 1, day 3, day 7, and day 20 to determine evoked potential threshold shifts. Permanent threshold shift was assessed at day 20. The cochleas were harvested at day 20 to allow for morphological examination of the cochleas. Data for TOM 2-32 is shown in Tables 6-8 and data for CH-65 is shown in Table 9, below.

TABLE 6

|  | 0.5 kHz | 1 kHz | 2 kHz | 4 kHz | 8 kHz |
|---|---|---|---|---|---|
| Pretest |  |  |  |  |  |
| Control | 20 | 20 | 15 | 15 | 15 |
|  | 25 | 20 | 25 | 20 | 10 |
| Control | 22.5 | 20 | 20 | 17.5 | 12.5 |
| TOM2 | 25 | 25 | 20 | 15 | 10 |
|  | 30 | 30 | 30 | 20 | 10 |
| TOM2 | 27.5 | 27.5 | 25 | 17.5 | 10 |
| TOM2 6778 |  |  |  |  |  |
| Day 0 | 55 | 70 | 75 | 85 | 80 |
| Day 1 | 35 | 30 | 65 | 75 | 75 |
| Day 3 | 15 | 5 | 40 | 45 | 60 |
| Day 20 | 5 | 5 | 25 | 30 | 0 |
| Control 6778 |  |  |  |  |  |
| Day 0 | 60 | 75 | 80 | 80 | 75 |
| Day 1 | 45 | 40 | 75 | 75 | 75 |
| Day 3 | 10 | 10 | 50 | 55 | 55 |
| Day 20 | 5 | 10 | 40 | 35 | 25 |
| TOM 6679 |  |  |  |  |  |
| Day 0 | 55 | 60 | 65 | 75 | 75 |
| Day 1 | 30 | 50 | 60 | 70 | 75 |
| Day 3 | 20 | 25 | 40 | 55 | 45 |
| Day 20 | −5 | 0 | 10 | 23 | −5 |
| Control 6679 |  |  |  |  |  |
| Day 0 | 55 | 70 | 70 | 75 | 80 |
| Day 1 | 40 | 60 | 65 | 70 | 80 |
| Day 3 | 35 | 60 | 65 | 75 | 80 |
| Day 20 | 0 | 10 | 25 | 35 | 10 |
| Control |  |  |  |  |  |
| Day 0 | 55 | 70 | 70 | 75 | 80 |
| Day 0 | 70 | 75 | 80 | 80 | 75 |
| Average Day 0 | 57.5 | 72.5 | 75 | 77.5 | 77.5 |
| Day 1 | 40 | 60 | 65 | 70 | 80 |
| Day 1 | 45 | 40 | 75 | 75 | 75 |
| Average Day 1 | 42.5 | 50 | 70 | 72.5 | 77.5 |
| Day 3 | 35 | 60 | 65 | 75 | 80 |
| Day 3 | 10 | 10 | 50 | 55 | 55 |
| Average Day 3 | 22.5 | 35 | 57.5 | 65 | 67.5 |
| Day 20 | 0 | 10 | 25 | 35 | 10 |
| Day 20 | 5 | 10 | 40 | 35 | 25 |
| Average Day 20 | 2.5 | 10 | 32.5 | 35 | 17.5 |
| TOM2 |  |  |  |  |  |
| Day 0 | 55 | 70 | 75 | 85 | 80 |
| Day 0 | 55 | 60 | 65 | 75 | 75 |
| Average day 0 | 55 | 65 | 70 | 80 | 77.5 |
| Day 1 | 35 | 30 | 65 | 75 | 75 |
| Day 1 | 30 | 50 | 60 | 70 | 75 |
| Average Day 1 | 32.5 | 40 | 62.5 | 72.5 | 75 |
| Day 3 | 15 | 5 | 40 | 45 | 60 |
| Day 3 | 20 | 25 | 40 | 55 | 45 |
| Average Day 3 | 17.5 | 15 | 40 | 50 | 52.5 |
| Day 20 | 5 | 5 | 25 | 30 | 0 |
| Day 20 | −5 | 0 | 10 | 23 | −5 |
| Average Day 20 | 0 | 2.5 | 17.5 | 26.5 | −2.5 |
| Control Day 0 | 57.5 | 72.5 | 75 | 77.5 | 77.5 |
| TOM2 Day 0 | 55 | 65 | 70 | 80 | 77.5 |
| Control Day 1 | 42.5 | 50 | 70 | 72.5 | 77.5 |

TABLE 6-continued

|  | 0.5 kHz | 1 kHz | 2 kHz | 4 kHz | 8 kHz |
| --- | --- | --- | --- | --- | --- |
| TOM2 Day 1 | 32.5 | 40 | 62.5 | 72.5 | 75 |
| Control Day 3 | 22.5 | 35 | 57.5 | 65 | 67.5 |
| TOM2 Day 3 | 17.5 | 15 | 40 | 50 | 52.5 |
| Control Day 20 | 2.5 | 10 | 32.5 | 35 | 17.5 |
| TOM2 Day 20 | 0 | 2.5 | 17.5 | 26.5 | −2.5 |
| Control Day 0 | 57.5 | 72.5 | 75 | 77.5 | 77.5 |
| Control Day 1 | 42.5 | 50 | 70 | 72.5 | 77.5 |
| Control Day 3 | 22.5 | 35 | 57.5 | 65 | 67.5 |
| Control Day 20 | 2.5 | 10 | 32.5 | 35 | 17.5 |
| TOM2 Day 0 | 55 | 65 | 70 | 80 | 77.5 |
| TOM2 Day 1 | 32.5 | 40 | 62.5 | 72.5 | 75 |
| TOM2 Day 3 | 17.5 | 15 | 40 | 50 | 52.5 |
| TOM2 Day 20 | 0 | 2.5 | 17.5 | 26.5 | −2.5 |
| TOM2 Day 20 | 0 | 2.5 | 17.5 | 26.5 | −2.5 |
| Control Day 20 | 2.5 | 10 | 32.5 | 35 | 17.5 |

TABLE 7

|  | 0.5 kHz | 1 kHz | 2 kHz | 4 kHz | 8 kHz |
| --- | --- | --- | --- | --- | --- |
| TOM2 6696 |  |  |  |  |  |
| day 0 | 38 | 50 | 70 | 75 | 80 |
| day 1 | 27 | 20 | 70 | 75 | 65 |
| day 3 | 10 | 15 | 55 | 53 | 55 |
| day 7 | 13 | 10 | 45 | 50 | 50 |
| day 20 |  |  |  |  |  |
| Control 6696 |  |  |  |  |  |
| day 0 | 35 | 45 | 75 | 80 | 90 |
| day 1 | 30 | 40 | 75 | 80 | 80 |
| day 3 | 7 | 15 | 50 | 60 | 70 |
| day 7 | 5 | 15 | 45 | 50 | 60 |
| day 20 |  |  |  |  |  |
| TOM2 6698 |  |  |  |  |  |
| day 0 | 30 | 45 | 65 | 70 | 80 |
| day 1 | 0 | 15 | 45 | 65 | 60 |
| day 3 | −5 | 5 | 25 | 40 | 40 |
| day 7 | −5 | 5 | 25 | 25 | 0 |
| day 20 | −5 | 0 | 0 | 0 | −5 |
| Control 6698 |  |  |  |  |  |
| day 0 | 55 | 40 | 65 | 70 | 80 |
| day 1 | 10 | 15 | 45 | 60 | 70 |
| day 3 | 15 | 15 | 45 | 40 | 55 |
| day 7 | 5 | 5 | 25 | 35 | 10 |
| day 20 | 10 | 10 | 20 | 30 | 5 |
| TOM2 6699 |  |  |  |  |  |
| day 0 | 70 | 65 | 70 | 75 | 85 |
| day 1 | 60 | 65 | 70 | 75 | 85 |
| day 3 | 25 | 20 | 70 | 70 | 75 |
| day 7 | 10 | 5 | 45 | 40 | 45 |
| day 20 | 10 | 10 | 45 | 40 | 45 |
| Control 6699 |  |  |  |  |  |
| day 0 | 70 | 70 | 65 | 70 | 85 |
| day 1 | 60 | 70 | 65 | 70 | 85 |
| day 3 | 50 | 65 | 60 | 65 | 70 |
| day 7 | 38 | 55 | 50 | 45 | 65 |
| day 20 | 28 | 35 | 50 | 45 | 60 |
| Pretest |  |  |  |  |  |
| Controls | 25 | 25 | 30 | 25 | 10 |
|  | 25 | 30 | 30 | 25 | 15 |
| Controls | 25 | 27.5 | 30 | 25 | 12.5 |
| TOM2 | 35 | 30 | 30 | 25 | 15 |
|  | 25 | 30 | 25 | 20 | 10 |
| TOM2 | 30 | 30 | 27.5 | 22.5 | 12.5 |

TABLE 8

|  | Control | TOM2 |
| --- | --- | --- |
| 0.5 kHz |  |  |
| day 0 | 62.5 | 50 |
| day 1 | 35 | 30 |
| day 3 | 32.5 | 10 |
| day 7 | 21.5 | 2.5 |
| day 20 | 19 | 2.5 |
| 1 kHz |  |  |
| day 0 | 55 | 55 |
| day 1 | 42.5 | 40 |
| day 3 | 40 | 12.5 |
| day 7 | 30 | 5 |
| day 20 | 22.5 | 5 |
| 2 kHz |  |  |
| day 0 | 65 | 67.5 |
| day 1 | 55 | 57.5 |
| day 3 | 52.5 | 47.5 |
| day 7 | 37.5 | 35 |
| day 20 | 35 | 22.5 |
| 4 kHz |  |  |
| day 0 | 70 | 72.5 |
| day 1 | 65 | 70 |
| day 3 | 52.5 | 55 |
| day 7 | 40 | 32.5 |
| day 20 | 37.5 | 20 |
| 8 kHz |  |  |
| day 0 | 82.5 | 82.5 |
| day 1 | 77.5 | 72.5 |
| day 3 | 62.5 | 57.5 |
| day 7 | 37.5 | 22.5 |
| day 20 | 32.5 | 20 |

TABLE 9

|  | 0.5 kHz | 1 kHz | 2 kHz | 4 kHz | 8 kHz |
| --- | --- | --- | --- | --- | --- |
| Pretest |  |  |  |  |  |
| Control 6821 | 30 | 20 | 25 | 15 | 7.5 |
| Control 6845 | 30 | 25 | 20 | 15 | 10 |
| Control 6850 | 27 | 25 | 15 | 10 | 0 |
| Control 6828 | 20 | 15 | 20 | 5 | 5 |
| Control 6829 | 20 | 20 | 20 | 20 | 5 |
| Control | 25.4 | 21 | 20 | 13 | 5.5 |
| CH65 6821 | 30 | 22.5 | 25 | 20 | 10 |
| CH65 6845 | 35 | 25 | 25 | 10 | 0 |
| CH65 6850 | 25 | 25 | 10 | 12 | 0 |
| CH65 6828 | 20 | 25 | 15 | 5 | 0 |
| CH65 6829 | 23 | 25 | 25 | 15 | 10 |
| CH65 | 26.6 | 24.5 | 20 | 12.4 | 4 |
| Day 1 |  |  |  |  |  |
| Control 6821 | 5 | 25 | 50 | 60 | 72.5 |
| Control 6845 | 15 | 15 | 40 | 75 | 80 |
| Control 6850 | 8 | 10 | 25 | 65 | 55 |
| Control 6828 | 5 | 20 | 55 | 75 | 80 |
| Control Day 1 | 8.25 | 17.5 | 42.5 | 68.75 | 71.875 |
| ctrlsd | 4.716991 | 6.454972 | 13.22876 | 7.5 | 11.79248 |
| CH65 6821 | 0 | 2.5 | 0 | 10 | 0 |
| CH65 6845 | 5 | 20 | 25 | 35 | 30 |
| CH65 6850 | 10 | 0 | 20 | 68 | 35 |
| CH65 6828 | 0 | 5 | 55 | 55 | 25 |
| CH65 Day 1 | 3.75 | 6.875 | 25 | 42 | 22.5 |
|  | 4.787136 | 8.984941 | 22.7303 | 25.28504 | 15.54563 |
| Day 3 |  |  |  |  |  |
| Control 6821 | 10 | 25 | 50 | 55 | 67.5 |
| Control 6845 | 10 | 15 | 35 | 55 | 45 |
| Control 6850 | 3 | 5 | 15 | 25 | 15 |

TABLE 9-continued

|  | 0.5 kHz | 1 kHz | 2 kHz | 4 kHz | 8 kHz |
|---|---|---|---|---|---|
| Control 6828 | 5 | 15 | 40 | 65 | 55 |
| Control 6829 | 20 | 20 | 35 | 45 | 45 |
| Control | 9.6 | 16 | 35 | 49 | 45.5 |
| Day 3 |  |  |  |  |  |
|  | 6.580274 | 7.416198 | 12.74755 | 15.16575 | 19.39716 |
| CH65 6821 | 5 | 7.5 | 0 | 10 | 0 |
| CH65 6845 | 5 | 5 | 0 | 0 | 15 |
| CH65 6850 | 5 | 2 | 15 | 25 | 15 |
| CH65 6828 | 0 | 0 | 40 | 55 | 0 |
| CH65 6829 | 12 | 20 | 35 | 45 | 45 |
| CH65 Day 3 | 5.4 | 6.9 | 18 | 27 | 15 |
|  | 4.27785 | 7.861298 | 18.90767 | 23.07596 | 18.37117 |
| Day 7 |  |  |  |  |  |
| Control 6821 | 0 | 10 | 20 | 20 | 45 |
| Control 6845 | 10 | 15 | 25 | 45 | 45 |
| Control 6850 | 6 | 5 | 15 | 30 | 10 |
| Control 6828 | 10 | 20 | 37 | 65 | 60 |
| Control 6829 | 20 | 25 | 45 | 40 | 55 |
| Control | 9.2 | 15 | 28.4 | 40 | 43 |
| Day 7 |  |  |  |  |  |
|  | 7.293833 | 7.905694 | 12.36123 | 16.95582 | 19.55761 |
| CH65 6821 | 0 | 0 | 0 | 0 | 0 |
| CH65 6845 | 5 | 15 | 0 | 5 | 20 |
| CH65 6850 | 8 | 0 | 15 | 15 | 0 |
| CH65 6828 | 15 | 0 | 40 | 55 | 30 |
| CH65 6829 | 12 | 15 | 20 | 45 | 40 |
| CH65 Day 7 | 8 | 6 | 15 | 24 | 18 |
|  | 5.87367 | 8.215838 | 16.58312 | 24.59675 | 17.888854 |
| Day 20 |  |  |  |  |  |
| Control 6821 | 0 | 10 | 25 | 35 | 7.5 |
| Control 6845 | 0 | 5 | 25 | 45 | 40 |
| Control 6850 | 8 | 0 | 10 | 20 | 10 |
| Control 6829 | 15 | 20 | 30 | 30 | 18 |
| Control | 5.75 | 8.75 | 22.5 | 32.5 | 18.875 |
| Day 20 |  |  |  |  |  |
|  | 7.228416 | 8.539126 | 8.660254 | 10.40833 | 14.77822 |
| CH65 6821 | 0 | 0 | 0 | 0 | −5 |
| CH65 6845 | 0 | 0 | 0 | 0 | 5 |
| CH65 6850 | 5 | 0 | 15 | 11 | 0 |
| CH65 6829 | 7 | 5 | 10 | 25 | 15 |
| CH65 | 3 | 1.25 | 6.25 | 9 | 3.75 |
| Day 20 |  |  |  |  |  |
|  | 3.559026 | 2.5 | 7.5 | 11.80603 | 8.539126 |
| Control | 8.25 | 17.5 | 42.5 | 68.75 | 71.875 |
| Day 1 |  |  |  |  |  |
| Control | 9.6 | 16 | 35 | 49 | 45.5 |
| Day 3 |  |  |  |  |  |
| Control | 9.2 | 15 | 28.4 | 40 | 43 |
| Day 7 |  |  |  |  |  |
| Control | 5.75 | 8.75 | 22.5 | 32.5 | 18.875 |
| Day 20 |  |  |  |  |  |
| Ch65 Day 1 | 3.75 | 6.875 | 25 | 42 | 22.5 |
| CH65 Day 3 | 5.4 | 6.9 | 18 | 27 | 15 |
| CH65 Day 7 | 8 | 6 | 15 | 24 | 18 |
| CH65 | 3 | 1.25 | 6.25 | 9 | 3.75 |
| Day 20 |  |  |  |  |  |

Figure 6:
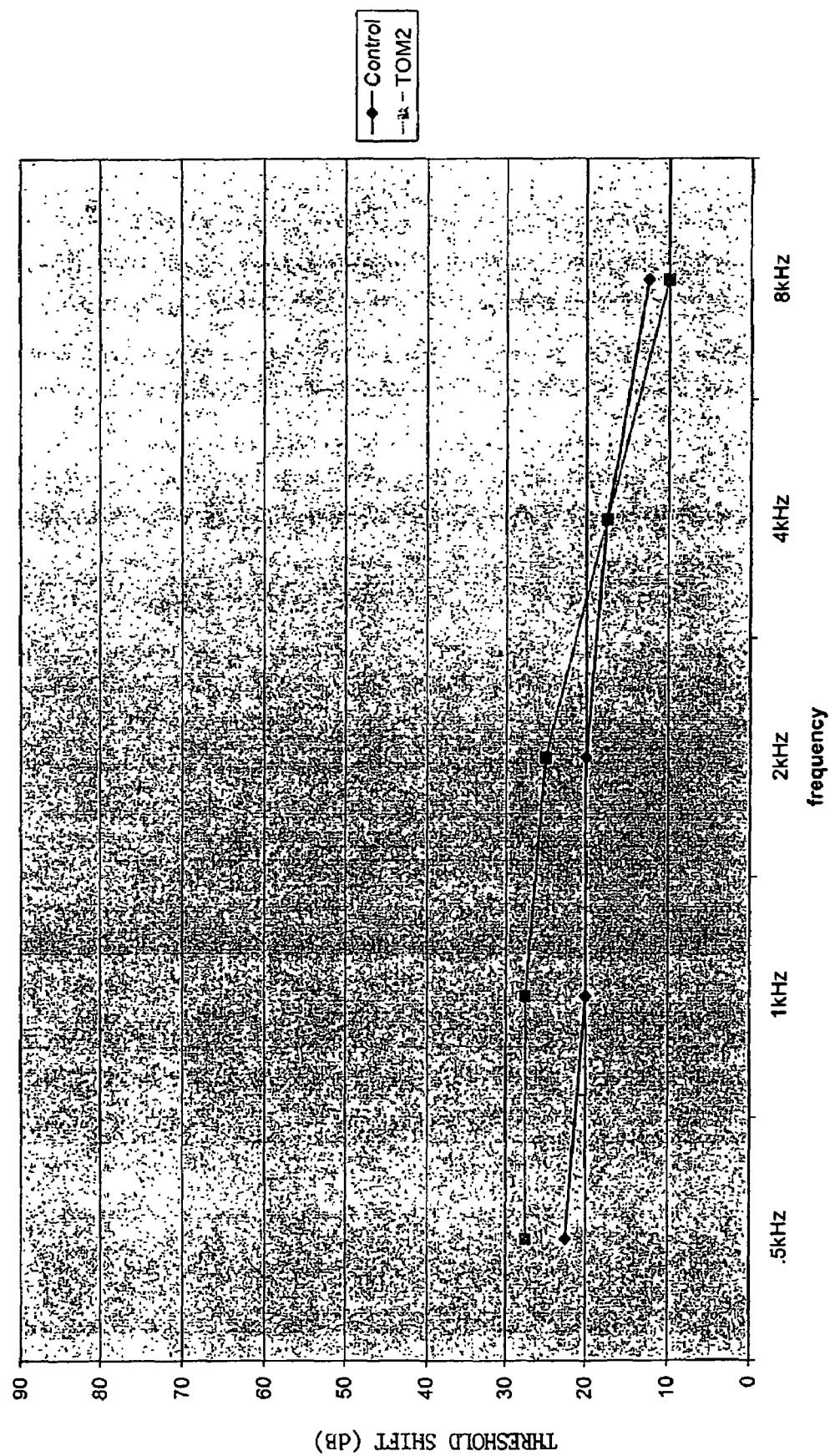
FIG. 6 is a graph showing average threshold shifts (dB) in chinchilla cochleas after exposure to 0.5 kHz, 1 kHz, 2 kHz, 4 kHz, and 8 kHz band noise prior to experimental manipulation.
Figure 7:
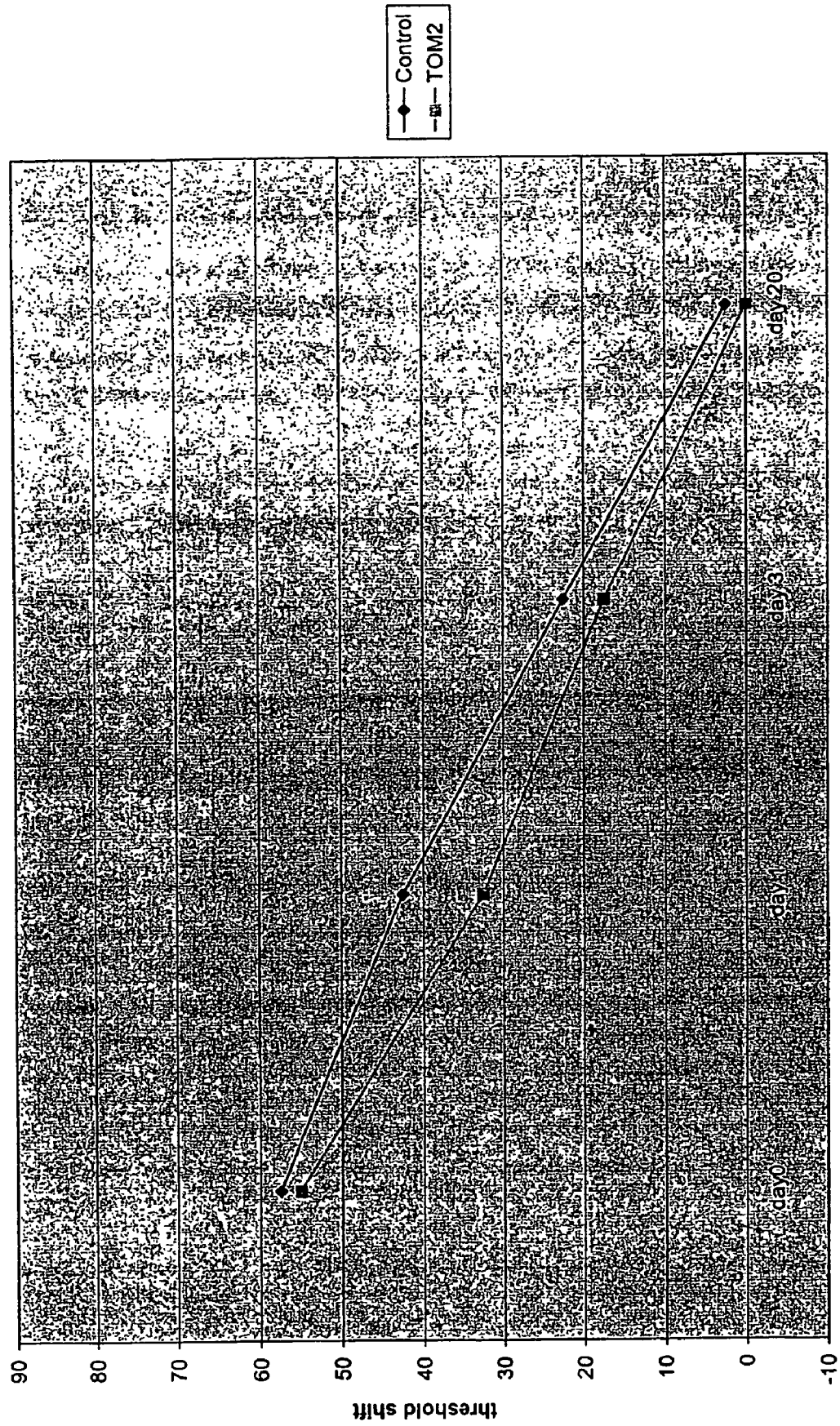
FIG. 7 is a graph showing average threshold shifts (dB) in chinchilla cochleas after exposure to 0.5 kHz band noise at day 0, day 1, day 3, and day 20 after experimental manipulation.
Figure 8:
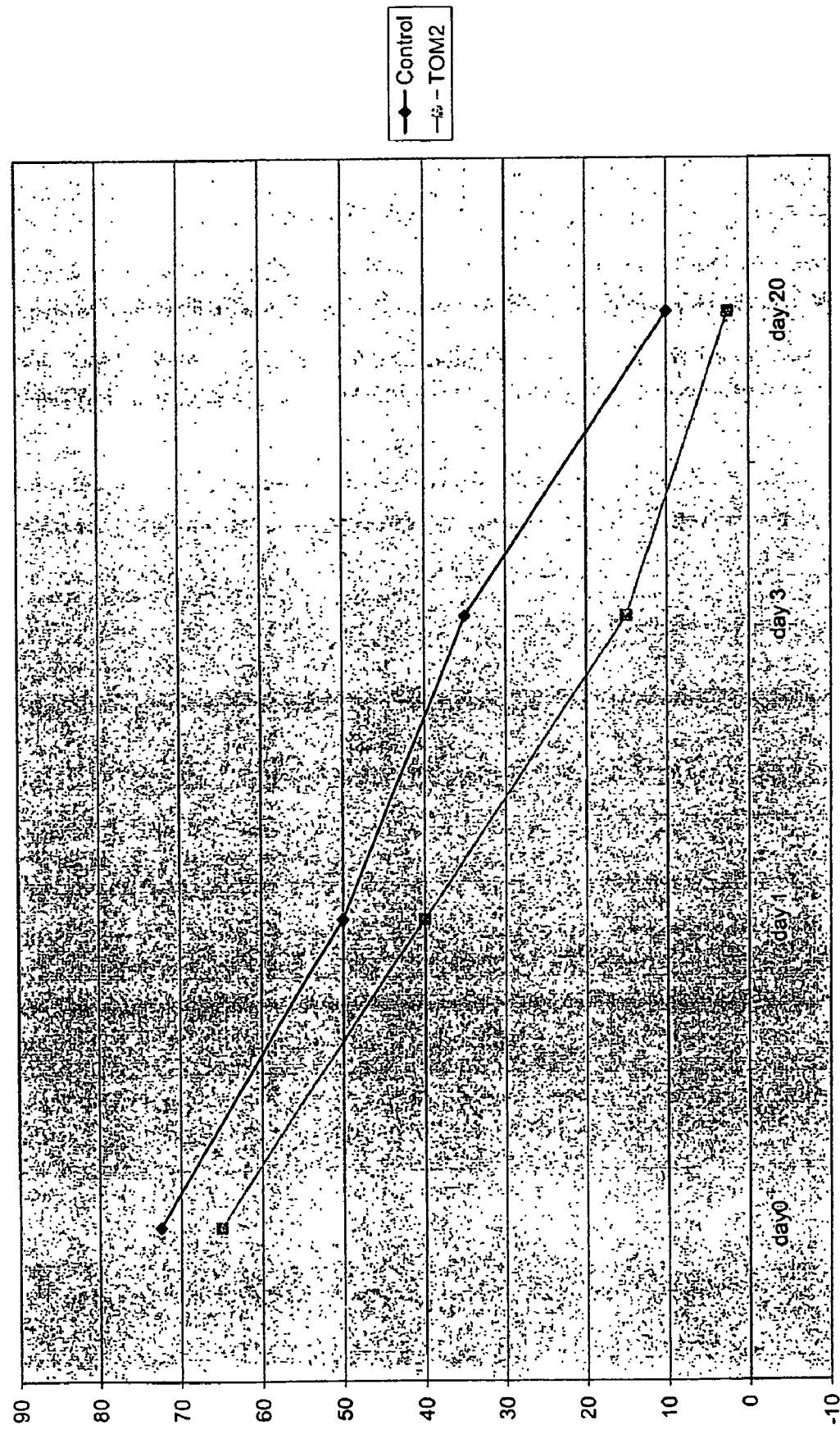
FIG. 8 is a graph showing average threshold shifts (dB) in chinchilla cochleas after exposure to 1 kHz band noise at day 0, day 1, day 3, and day 20 after experimental manipulation.
Figure 9:
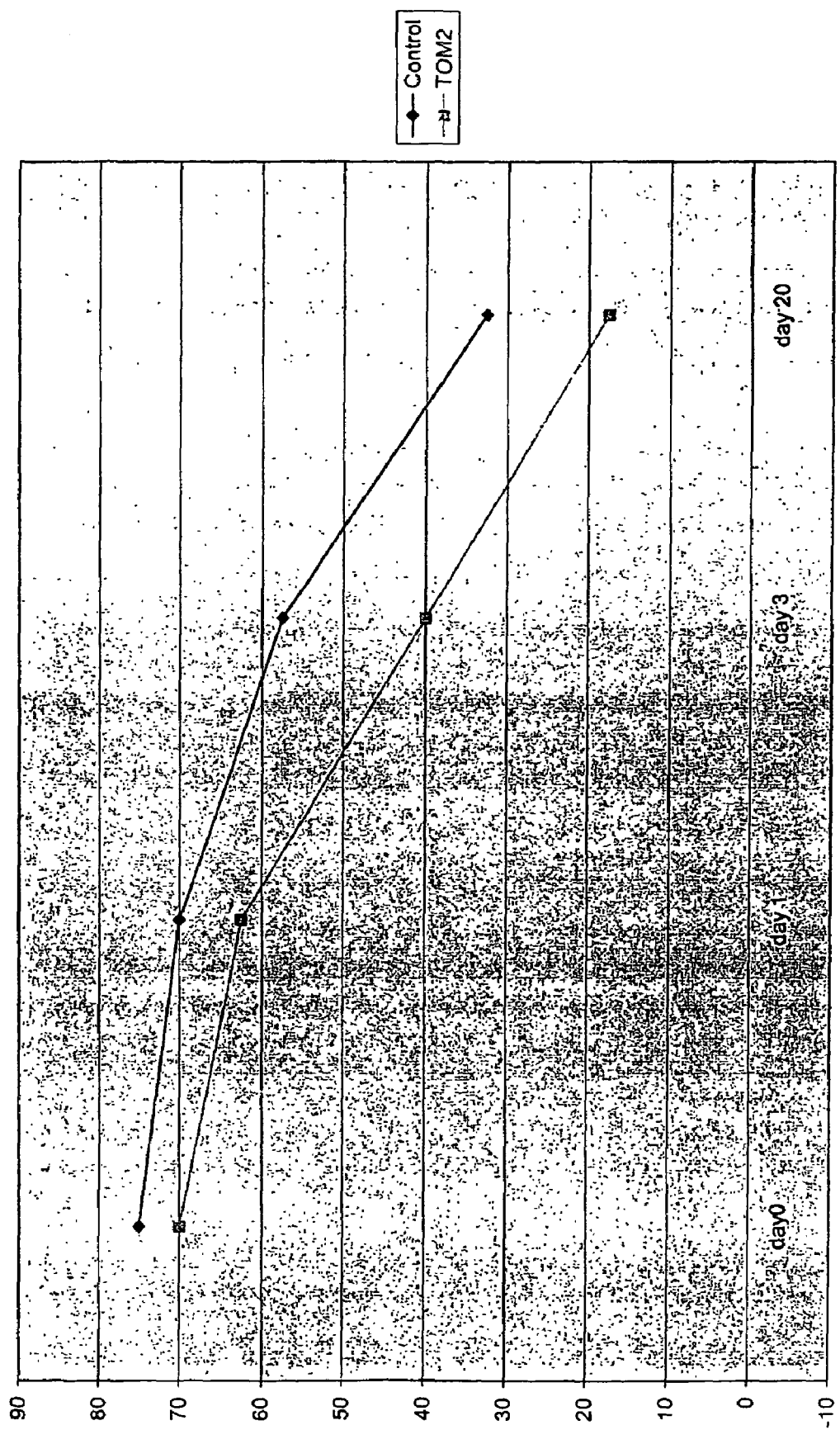
FIG. 9 is a graph showing average threshold shifts (dB) in chinchilla cochleas after exposure to 2 kHz band noise at day 0, day 1, day 3, and day 20 after experimental manipulation.
Figure 10:
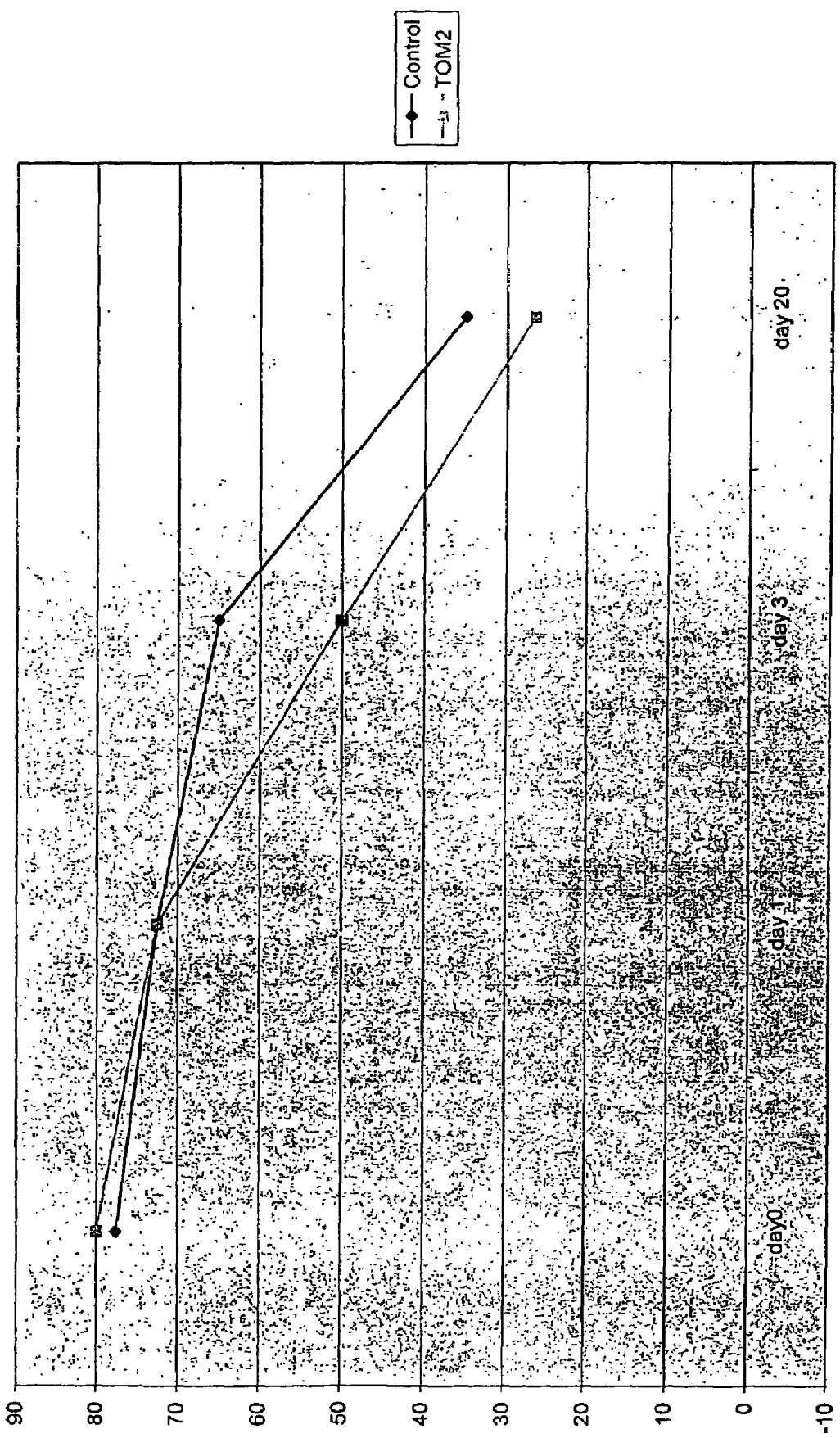
FIG. 10 is a graph showing average threshold shifts (dB) in chinchilla cochleas after exposure to 4 kHz band noise at day 0, day 1, day 3, and day 20 after experimental manipulation.
Figure 11:
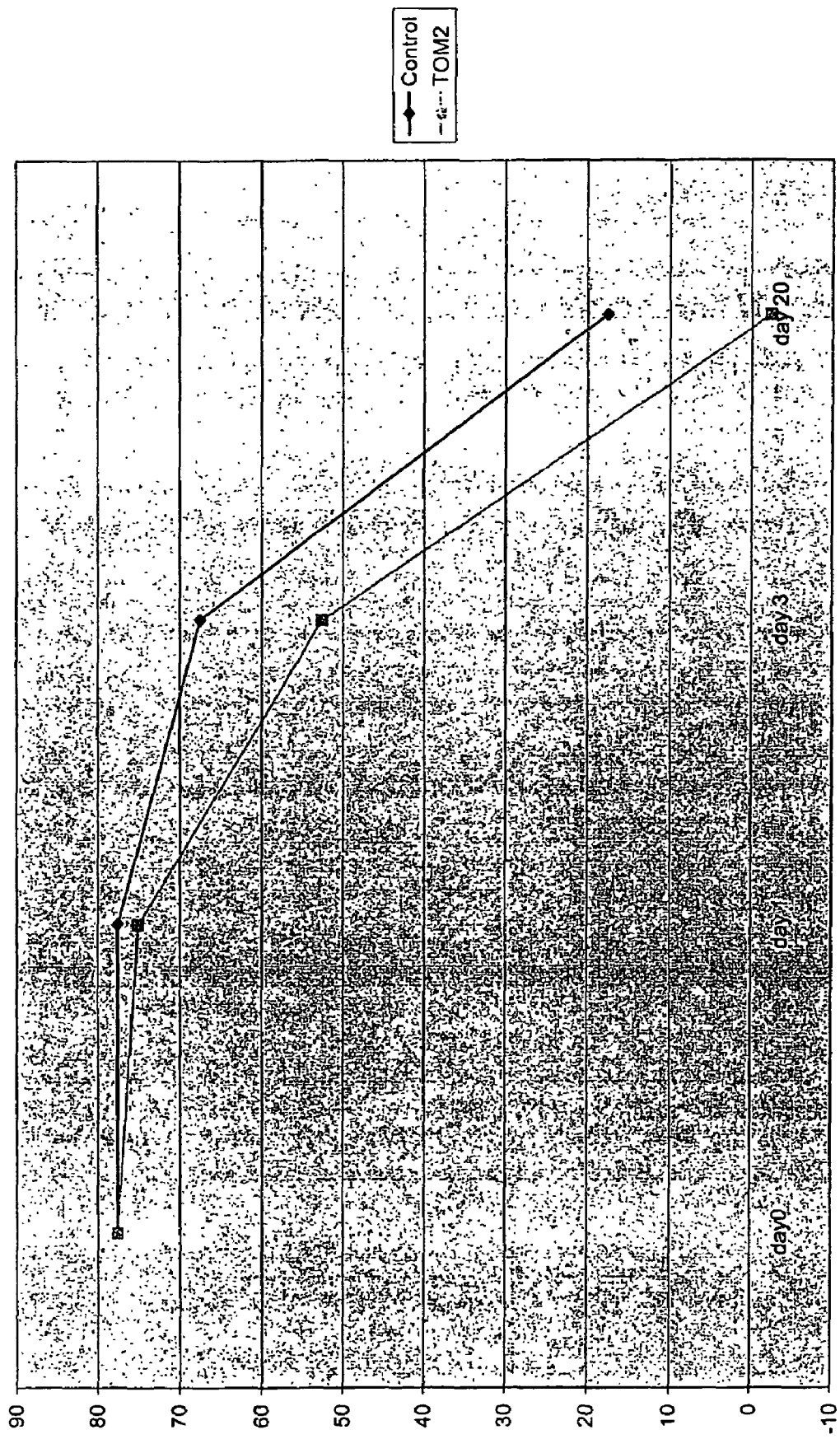
FIG. 11 is a graph showing average threshold shifts (dB) in chinchilla cochleas after exposure to 8 kHz band noise at day 0, day 1, day 3, and day 20 after experimental manipulation.
Figure 12:
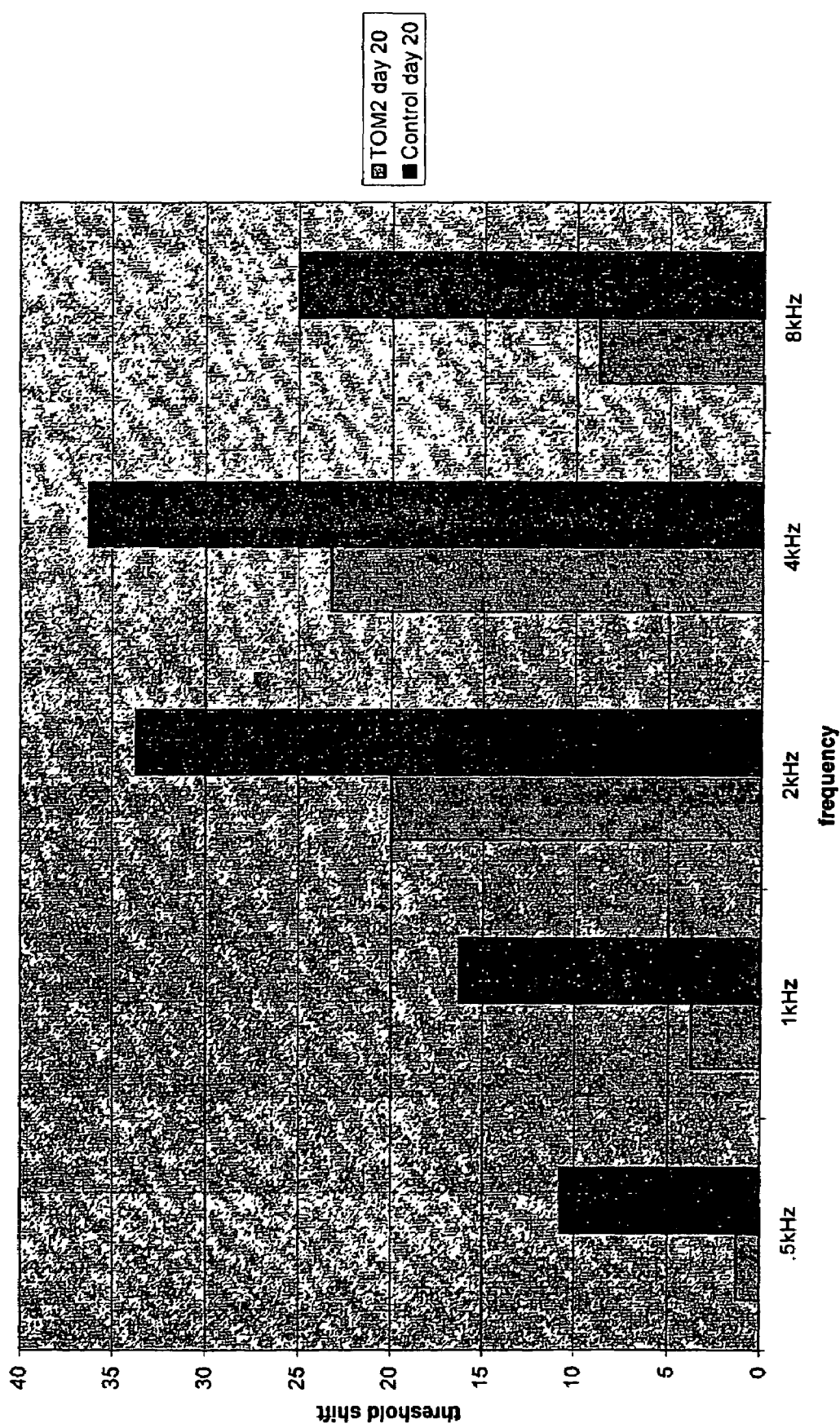
FIG. 12 is a graph showing the average dB threshold shifts in chinchilla cochleas at day 20 for control and treated ears.

FIGS. 6-12 show the average threshold shifts for animals treated with TOM 2-32. In particular, FIG. 6 shows average threshold shifts after exposure to 0.5 kHz, 1 kHz, 2 kHz, 4 kHz, and 8 kHz band noise tested prior to experimental manipulation (i.e., exposure to 4 kHz band noise at 105 dB for four hours). FIG. 7 shows average threshold shifts after exposure to 0.5 kHz band noise at day 0, day 1, day 3, and day 20 after experimental manipulation. FIG. 8 shows average threshold shifts after exposure to 1 kHz band noise at day 0, day 1, day 3, and day 20 after experimental manipulation. FIG. 9 shows average threshold shifts after exposure to 2 kHz band noise at day 0, day 1, day 3, and day 20 after experimental manipulation. FIG. 10 shows average threshold shifts after exposure to 4 kHz band noise at day 0, day 1, day 3, and day 20 after experimental manipulation. FIG. 11 shows average threshold shifts after exposure to 8 kHz band noise at day 0, day 1, day 3, and day 20 after experimental manipulation. FIG. 12 shows the average dB threshold shift at day 20 for control and treated ears. As shown in FIGS. 7-12 the average dB threshold shifts for treated ears were lower, indicating less hearing loss.

Figure 13:
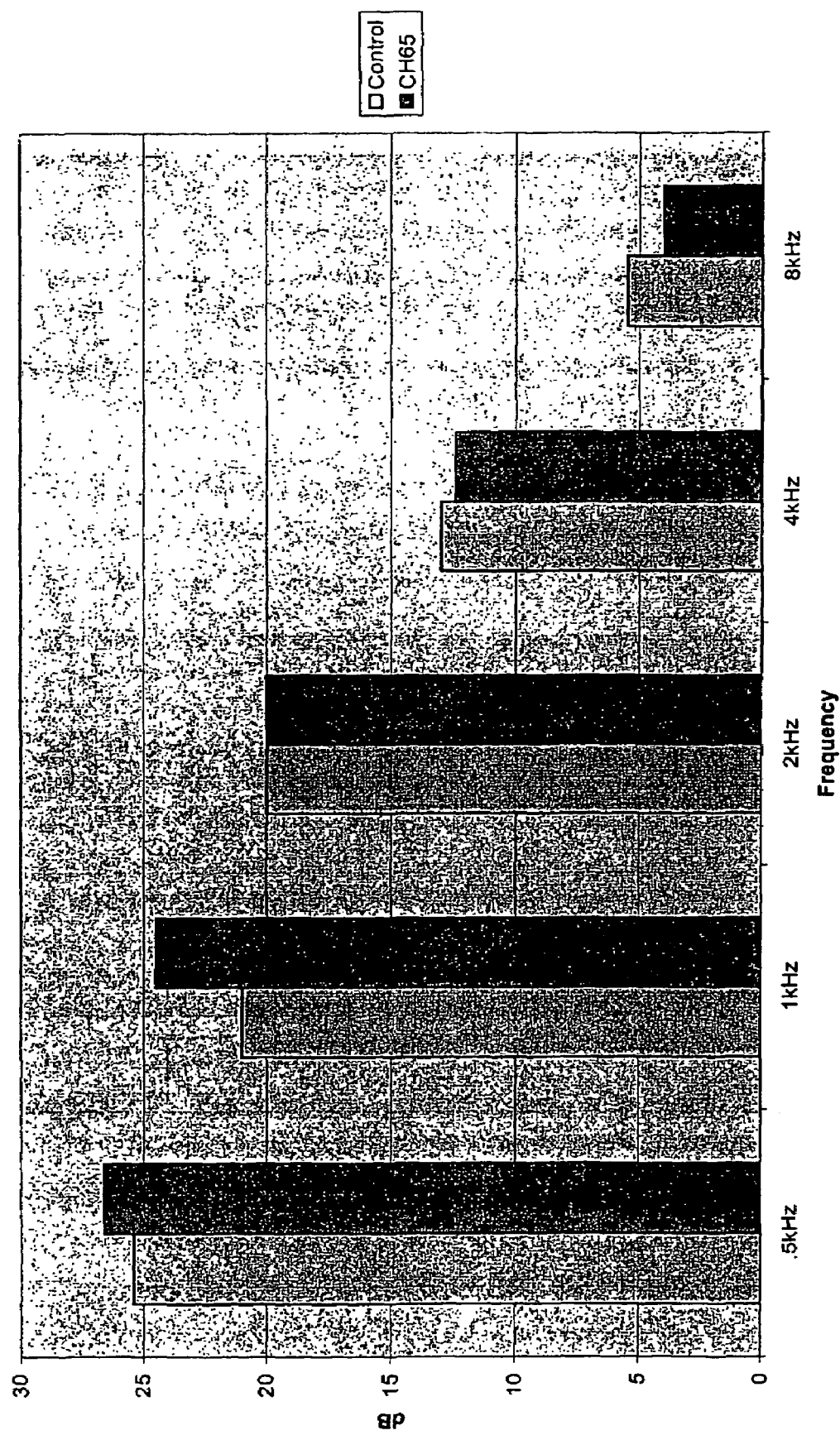
FIG. 13 is a graph showing average threshold shifts (dB) in chinchilla cochleas after exposure to 0.5 kHz, 1 kHz, 2 kHz, 4 kHz, and 8 kHz band noise prior to experimental manipulation.
Figure 14:
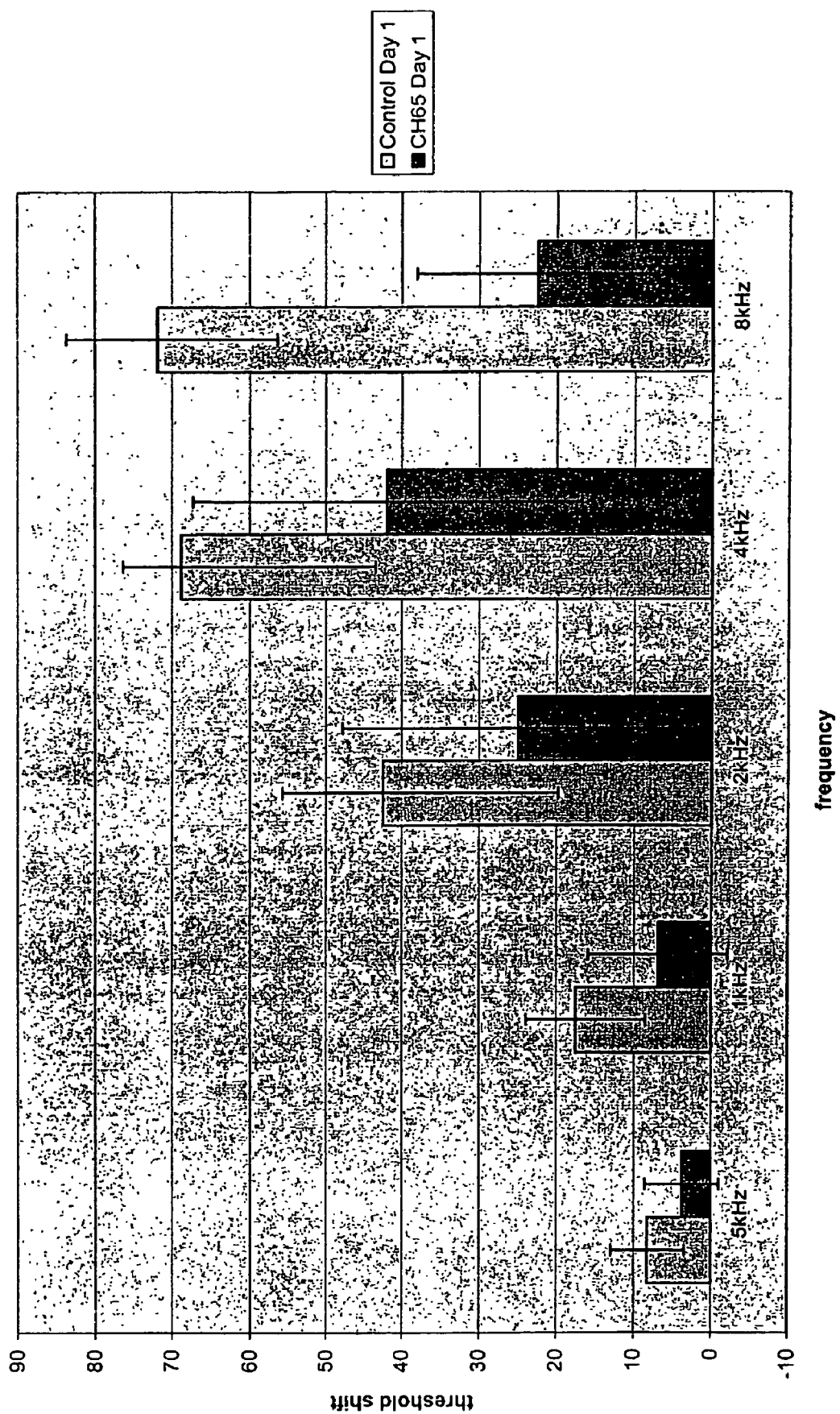
FIG. 14 is a graph showing average threshold shifts (dB) in chinchilla cochleas after exposure to 0.5 kHz, 1 kHz, 2 kHz, 4 kHz, and 8 kHz band noise on day 1 after experimental manipulation.
Figure 15:
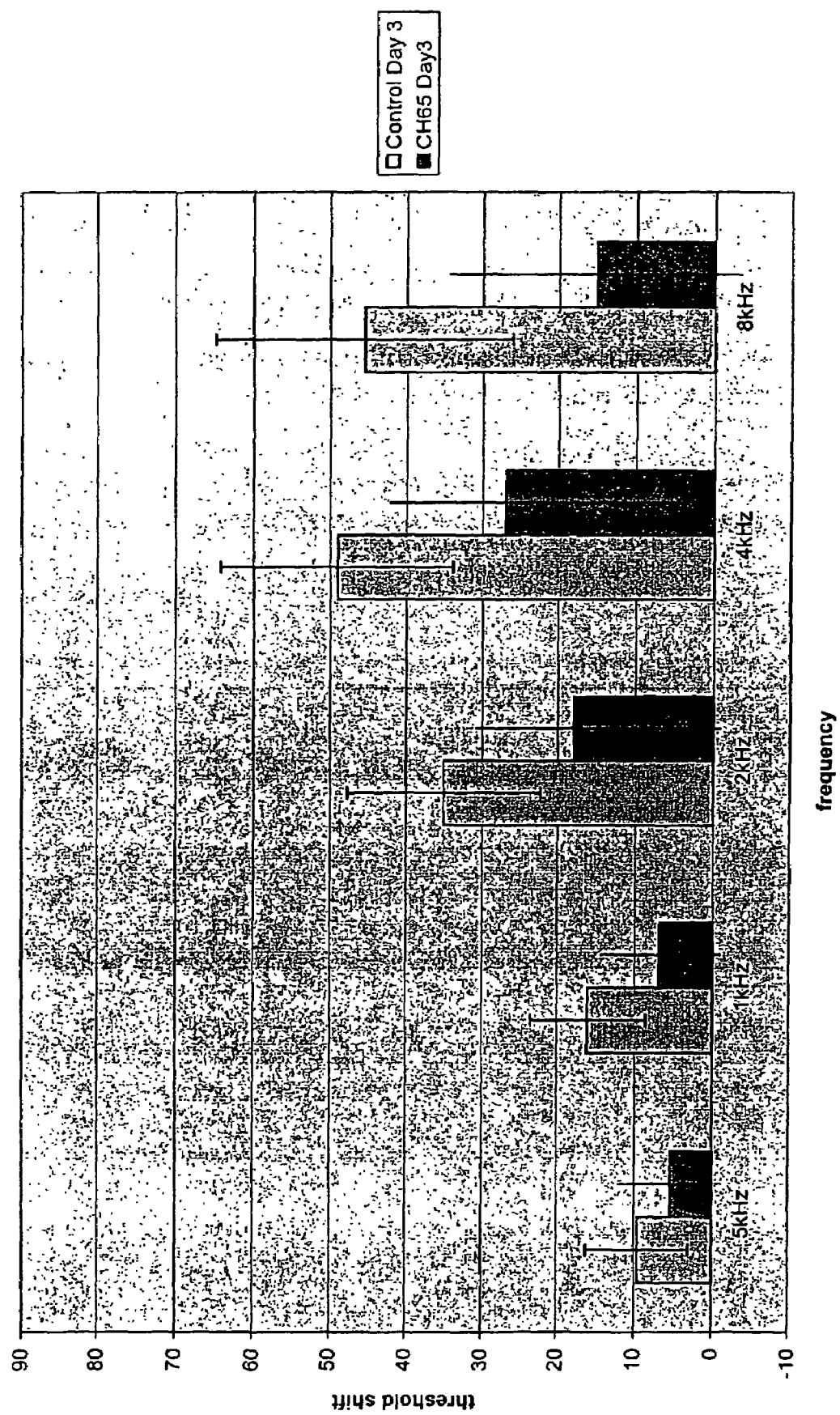
FIG. 15 is a graph showing average threshold shifts (dB) in chinchilla cochleas after exposure to 0.5 kHz, 1 kHz, 2 kHz, 4 kHz, and 8 kHz band noise on day 3 after experimental manipulation.
Figure 16:
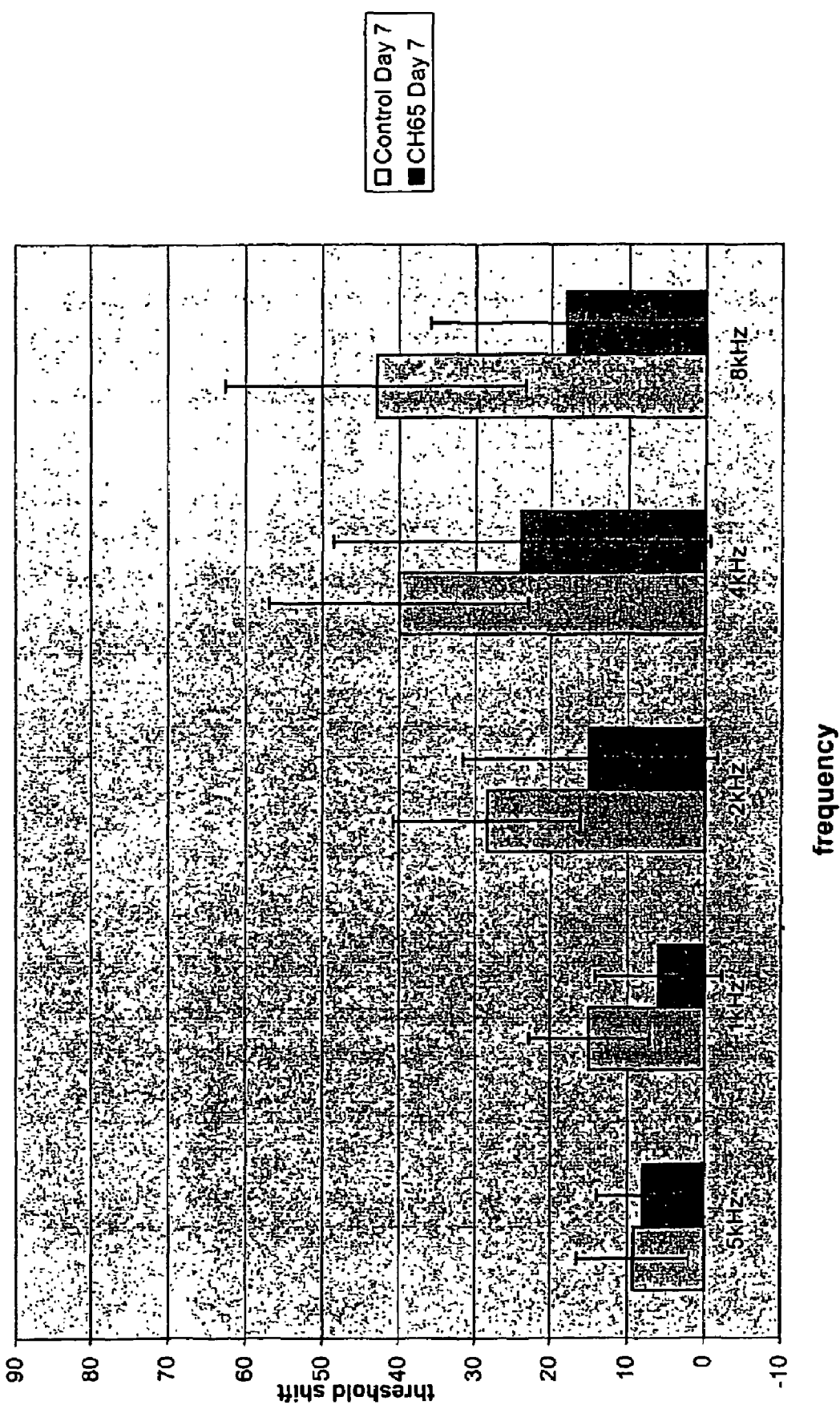
FIG. 16 is a graph showing average threshold shifts (dB) in chinchilla cochleas after exposure to 0.5 kHz, 1 kHz, 2 kHz, 4 kHz, and 8 kHz band noise on day 7 after experimental manipulation.
Figure 17:
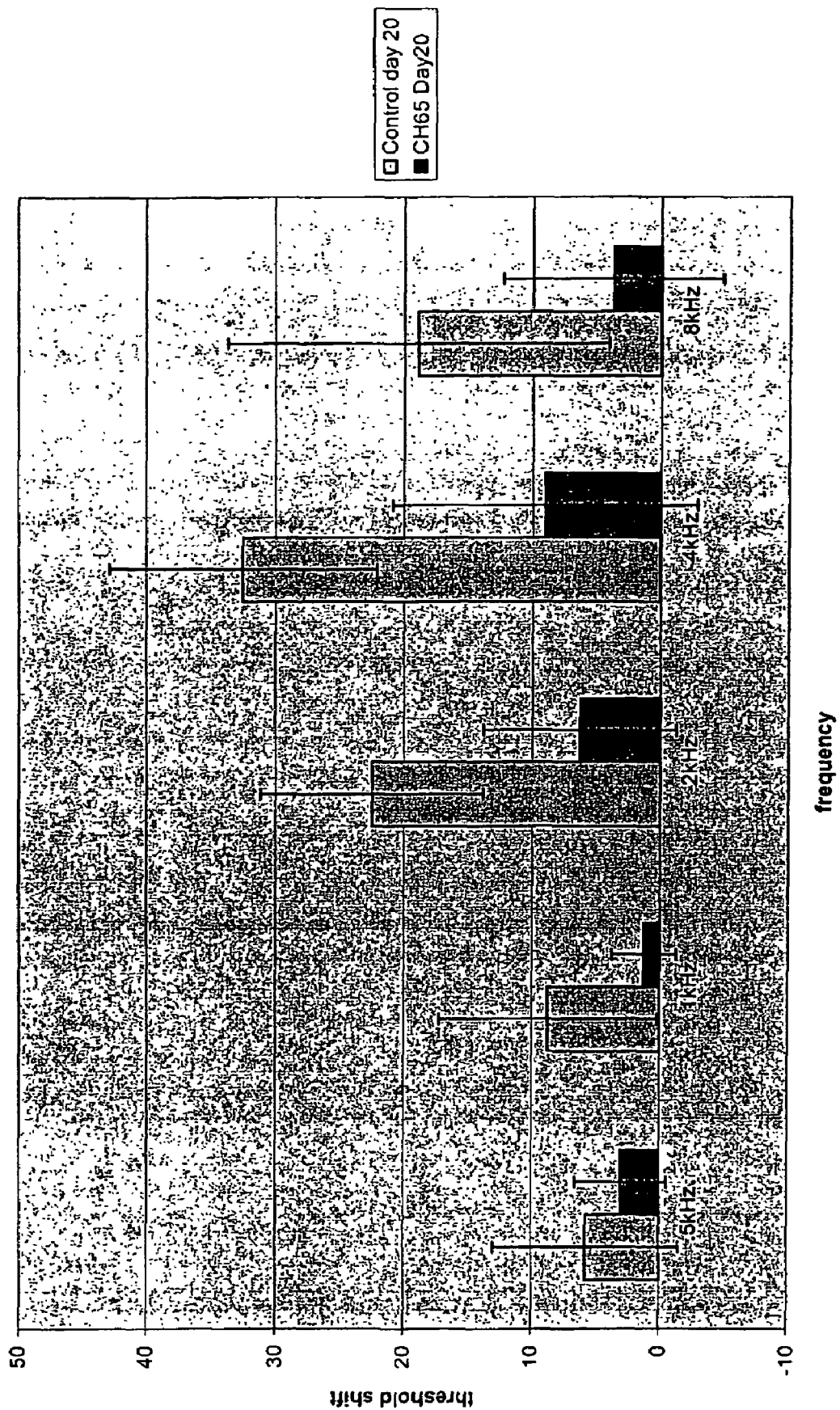
FIG. 17 is a graph showing average threshold shifts (dB) in chinchilla cochleas after exposure to 0.5 kHz, 1 kHz, 2 kHz, 4 kHz, and 8 kHz band noise on day 20 after experimental manipulation.
Figure 18:
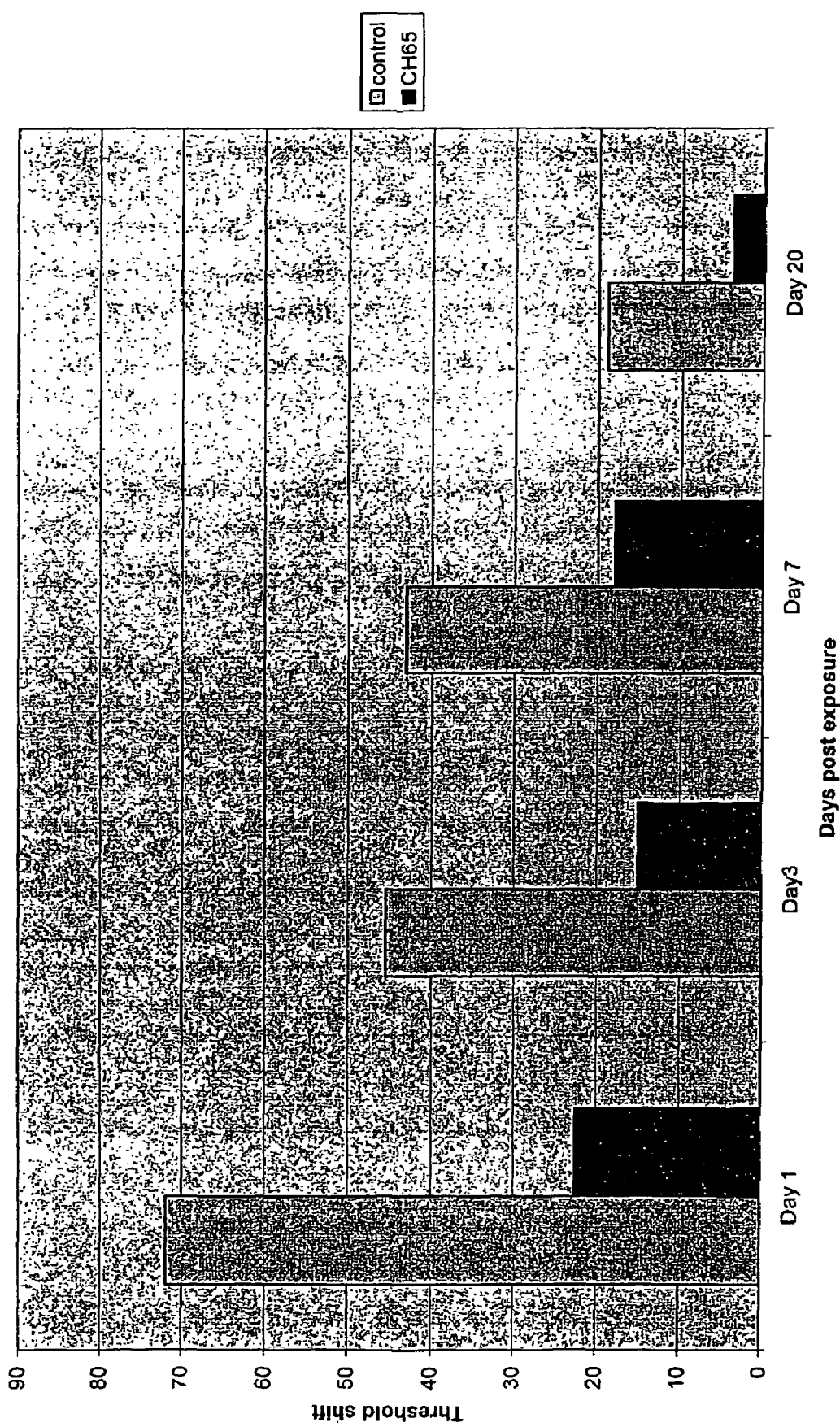
FIG. 18 is a graph showing average threshold shifts (dB) in chinchilla cochleas after exposure to 8000 Hz on day 1, day 3, day 7, and day 20.

FIGS. 13-18 show the average threshold shifts for animals treated with CH-65. In particular, FIG. 13 shows average threshold shifts after exposure to 0.5 kHz, 1 kHz, 2 kHz, 4 kHz, and 8 kHz band noise tested prior to experimental manipulation. FIG. 14 shows average threshold shifts after exposure to 0.5 kHz, 1 kHz, 2 kHz, 4 kHz, and 8 kHz band noise on day 1 after experimental manipulation. FIG. 15 shows average threshold shifts after exposure to 0.5 kHz, 1 kHz, 2 kHz, 4 kHz, and 8 kHz band noise on day 3 after experimental manipulation. FIG. 16 shows average threshold shifts after exposure to 0.5 kHz, 1 kHz, 2 kHz, 4 kHz, and 8 kHz band noise on day 7 after experimental manipulation. FIG. 17 shows average threshold shifts after exposure to 0.5 kHz, 1 kHz, 2 kHz, 4 kHz, and 8 kHz band noise on day 20 after experimental manipulation. FIG. 18 shows average threshold shifts after exposure to 8000 Hz on day 1, day 3, day 7, and day 20. As shown in FIGS. 14-18, the average dB threshold shifts for treated ears were lower, indicating less hearing loss.

As shown in FIGS. 6-18, both TOM 2-32 and CH-65 provided protection against the noise exposure. However, CH-65 provided the greatest level of protection. In particular, the PTK inhibitor treated ears had, on average, 15 to 25 dB less hearing loss than the control ears and the animals showed no side effects of the experimental manipulation.

Example 10

Inhibition of Noise-Induced Apoptosis in Cochlear Hair Cells Using Inhibitors of the PTKs Chinchillas (N=3) were exposed to 75-pairs of impulse noise at 155 dB pSPL. The animals were sacrificed 5 minutes after the noise exposure. The cochleas were examined for activation of the focal adhesion complex using an antibody against focal adhesion kinase, which is an intrinsic member of the complex.

FIGS. 19A-F show the effect of high level impulse noise on chinhilla cochleas without treatment with a PTK inhibitor. In particular, FIG. 19A is an electron micrograph which shows the cochlear damage following high level impulse noise (155 dB). FIG. 19A shows a spilt at the reticular lamina (S). The split appears to be between the second and third rows of outer hair cells. FIG. 19B depicts a cochlea stained immunohistochemcially for focal adhesion kinase (FAK) following a moderately high level octave band noise (105 dB). The staining observed in FIG. 19B is relatively low level and approximates that observed without noise. The staining appears to be localized primarily at the pharangeal processes of the Deiter cells and not at the hair cells. Upon elevating the noise level to 110 dB OBN, apoptotic cells appeared, as shown in FIG. 19C. These apoptotic cells are located in two regions of the upper left quadrant of the figure and the nuclei appear bright and highly condensed, whereas the normal nuclei are large and more diffuse in color. FIG. 19D is a photo of the same cells stained with focal adhesion kinase (FAK) antibody (as in FIG. 19B; however, here the pharangeal processes appear to surround a lesion where cells are missing). These lesions correspond to the areas in FIG. 19C where the cells underwent apoptosis. FIG. 19E shows the same region but at a lower vertical plane, demonstrating that the lesion extends well below the cuticular plate and into the cell body. FIG. 19F shows cochleas exposed to impulse noise at 155 dB SPL. The cochleas lost their integrity at the cuticular plate and were heavily stained throughout. Many dark areas are seen, which represent areas where hair cells have died.

Figure 20A:
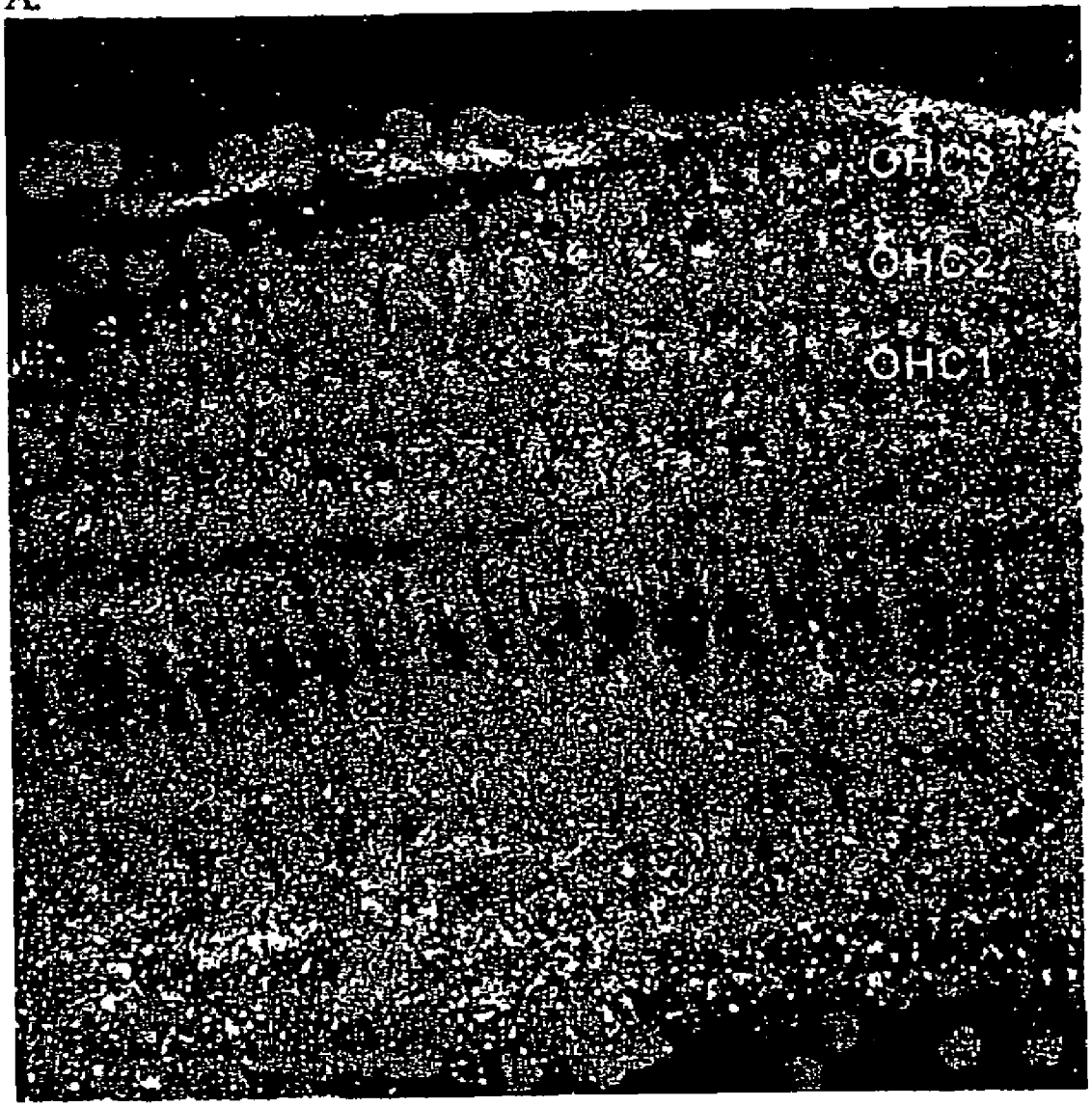
FIGS. 20A-B are confocal images of chinchilla cochleas exposed to high level noise.
Figure 20B:
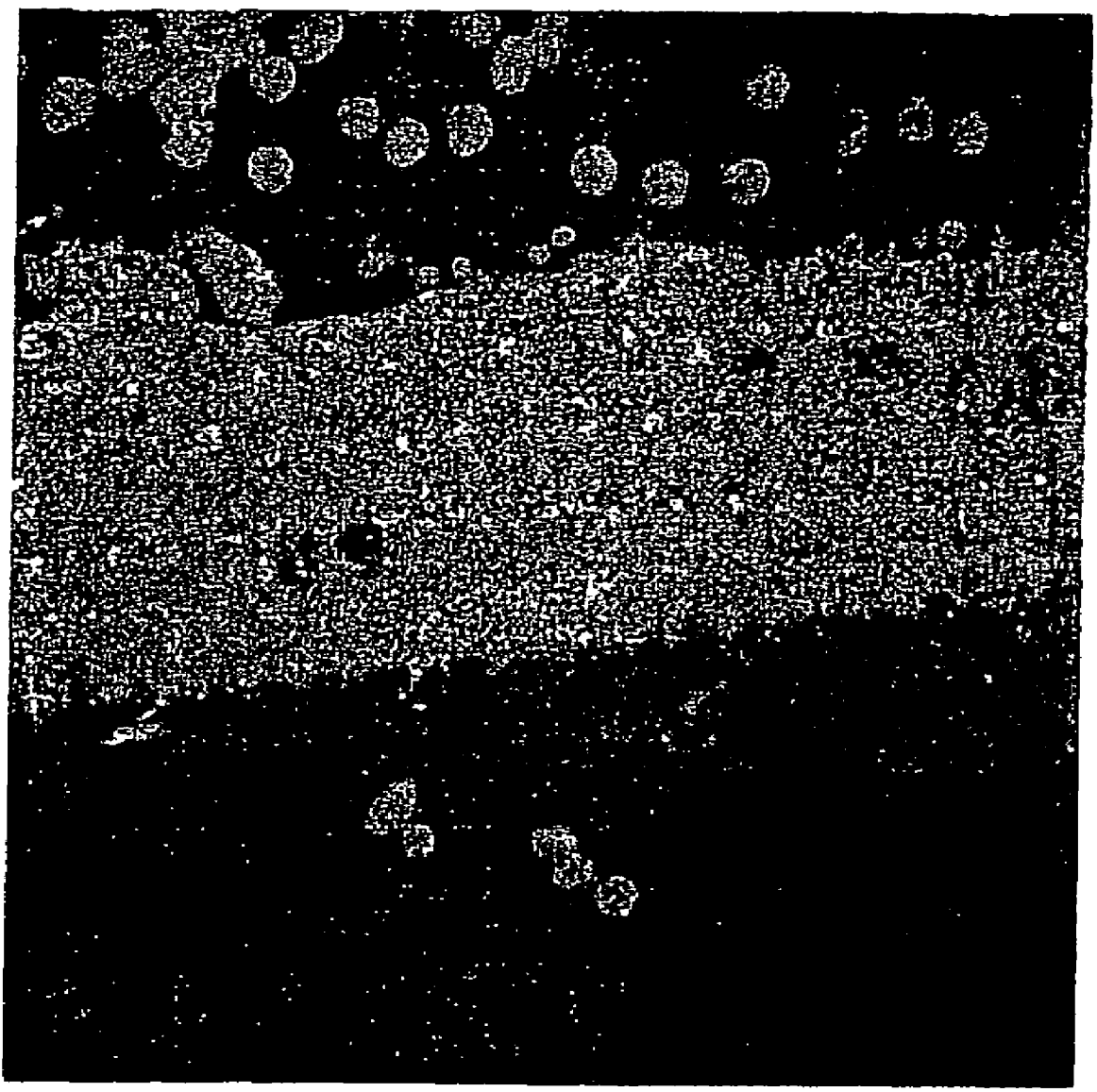

FIG. 20A shows a cochlea pretreated with CH-65, whereas FIG. 20B shows an untreated cochlea following exposure to high level noise (155 dB). In the treated cochlea (FIG. 20A), there is a high level of FAK staining that extends beyond the pharangeal processes of the Deiter cells and well into the cuticular plate. The punctate nature of the staining is indicative of the formation of focal adhesion complexes of which FAK is an intrinsic member. Furthermore, the three rows of hair cell nuclei (labeled OHC1-3) appear both in order and intact and without any indication of apoptosis taking place. Since FAK is known to be active within focal adhesion complexes, this data strongly suggests that FAK is active following a high noise exposure. It is hypothesized that it is the inhibition of the kinase function that is prevented through the treatment with CH-65 and results in the survival of cochlear hair cells.

In contrast to FIG. 20A, FIG. 20B demonstrates a somewhat lower level of FAK staining, but also shows a remarkably high level of cell death. In this figure, nearly half of the cells have died by apoptosis, as indicated by the number of condensed nuclei. This contrasts with FIG. 20A, where no apoptotic nuclei were observed with treatment. Since CH-65 can inhibit phosphorylation of several FAK substrates, including paxillin and pp130cas (see Example 7), it is believed that FAK kinase function in the cochlea is playing a protective role in response to high level noise exposure.

As described above, the PTK inhibitor treated ears showed less outer hair cell loss than controls. This indicates that anoikis (detachment from the cell's matrix, resulting in apoptosis) may play a significant role in noise-induced hair cell loss, and that blockage of apoptotic signals generated at the cell matrix can prevent hair cell loss.

More specifically, using the above chinchilla animal model, it has been demonstrated that focal adhesion complexes are formed in response to extremely high level noise. FAK is activated upon formation of these complexes and is known to initiate several signaling cascades, first through a series of autophosphorylation events and subsequently through phosphorylation of downstream peptide substrates. It has been demonstrated that apoptotic cells are seen within the lesion surrounded by focal adhesion complexes. Furthermore, addition of the $pp60^{c-src}$ inhibitor prevents the apoptotic response without preventing the formation of the focal adhesion complex. These data suggest that the downstream signaling through tyrosine phosphorylation by FAK may be an early step in the apoptotic signaling of hair cells. Since FAK is activated by shear stress in other organic systems, these observations may represent the first signaling pathway identified in the ear to be activated by mechanical stress.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

LITERATURE CITED

The following references which were cited herein, are hereby incorporated by reference in their entirety into this application:

Abate-Shen, C.; Shen, M. M. (2000) *Molecular Genetics of Prostate Cancer*. Genes & Dev., 14, 2410-2434.

Abram, C. L.; Courtneidge, S. A. (2000) *Src family tyrosine kinases and growth factor signaling*. Experimental Cell Research 254, 1-13.

Bakhtiar, R., Khemani, L., Hayes, M., Bedman, T., Tse, F. (2002) *Quantification of the anti-leukemia drug STI571 (Gleevec) and its metabolite (CGP79588) in monkey plasma using a semi-automated solid phase extraction procedure and liquid chromatography-tandem mass spectrometry*. J. Pharm. & Biomed. Anal., 2816, 1183-1194.

Barnekow, A.; Paul, E.; Schartl, M. (1987) *Expression of the c-src protooncogene in human skin tumors*. Cancer Res., 47, 235-240.

Biscardi, J. S., Tice, D. A.; Parsons, S. J. (1999) *c-Src, Receptor Tyrosine Kinases and Human Cancer*. Advances in Cancer Research, 61-119.

Biscardi, K. S., Ishizawar, R. C.; Silva, C. M.; Parsons, S. J. (2000) *Tyrosine kinase signaling in breast cancer: Epidermal growth factor receptor and c-Src interactions in breast cancer*. Breast Cancer Res. 2, 203-210.

Bjorge, J. D., O'Connor, T. J., Fujita, D. J. (1996) *Activation of human $pp60^{c-src}$*. Biochemistry & Cell Biology, 74, 477-484.

Bjelfman, C.; Hedborg, F.; Johansson, I.; Nordenskjold, M.; Pahlman, S. (1990) *Expression of the neuronal for of pp60c-src in neuroblastoma in relation to clinical stage and prognosis*. Cancer Res, 50, 6908-6914.

Blume-Jensen, P.; Hunter, T. (2001) *Oncogenic kinase signaling*. Nature 411, 355-365.

Bridges, A. J. (2001) *Chemical Inhibitors of Protein Kinases*. Chemical Reviews 101(8), 2542-2572.

Budde, R. J. A., McMurray, J. S., Saya, H., Gallick, G. E. & Levin, V. A. (1995) *Discovery, Development, and Testing of Substrates and Inhibitors of $pp60^{c-src}$*. International Journal of Pharmacognosy, 33, 27-34.

Burger, A. M., Kaur, G., Alley, M. C., Supko, J. G., Malspeis, L., Grever, M. R. & Sausville, E. A. (1995) *Tyrphostin AG17, [(3,5-Di-tert-butyl-4-hydroxybenzylidene)-malonitrile], inhibits cell growth by disrupting mitochondria*. Cancer Research, 55, 2794-2799.

Burke, T. R.; Lim, B.; Marquez, V. E.; Li, Z-H.; Bolen, J. B.; Stefanova, I.; Horak, I. D. (1993) J. Med. Chem. 36, 425.

Choi, S. (1999), Ph.D. Thesis SUNY at Buffalo, Buffalo, N.Y.

Courtneidge, S. A. (1994) *Protein tyrosine kinases, with emphasis on the Src family*. Seminars in Cancer Biology, 5, 239-246.

Cox, S., Radzio-Andzelm, E. & Taylor, S. S. (1994) *Domain movements in protein kinases*. Current Opinion in Structural Biology, 4(6), 893-901.

Davis, P. D.; Hill, C. H.; Keech, E.; Lawton, G.; Nixon, J. S.; Sedgwick, A. D.; Wadsworth, J.; Westmacott, D.; Wilkinson, S. E. (1989) FEBS Lett. 259(1), 61.

Davis, P. D.; Elliott, L. H.; Harris, W.; Hill, C. H.; Hurst, S. A.; Keech, E.; Kumar, M. K. H.; Lawton, G.; Nixon, J. S.; Wilkinson, S. E. (1992) J. Med. Chem. 35, 994.

Dorkin, T.; Neal, D. (1997) *Basic science aspects of prostate cancer*. Sem. in Cancer Biol., 8, 21-27.

Druker, B. J. (2000) *STI571 (Gleevec) as a paradigm for cancer therapy*. Trends in Molec. Med., 8(4 Suppl.), S14-18.

Ellis, L. M., Staley, C. A., Liu, W., Fleming, R. Y., Parikh, N. U., Bucana, C. D., & Gallick, G. E. (1998) *Down-regulation of vascular endothelial growth factor in a human colon carcinoma cell line transfected with an antisense expression vector specific for c-src*. Journal of Biological Chemistry 273 (2): 1052-1057.

Faltynek, C., et al. (1995) *Damnacanthal is a highly potent, selective inhibitor of p56lck tyrosine kinase activity*. Biochemistry 34, 12404-12410.

Faltynek, C. R.; Wang, S.; Miller, D.; Mauvais, P.; Gauvin, B.; Reid, J.; Xie, W.; Hoekstra, S.; Juniewicz, P.; Sarup, J.; Lehr, R.; Sawutz, D. G.; Murphy, D. J. (1995) Enzyme Inhibition 9, 111.

Fanning, P.; Bulovas, K.; Saini, K. S.; Libertino, J. A.; Joyce, A. D.; Summerhayes, I. C. (1992) *Elevated expression of pp60$^{c\text{-}src}$ in low grade human bladder carcinoma*. Cancer Research, 52, 1457-1462.

Frame, M. C. (2002) *Src in cancer: deregulation and consequences for cell behavior*. Biochemica et Biophysica Acta, 1602, 114-130.

Fretz, H.; Furet, P.; Garcia-Echeverria, C.; Rahuel, J.; Schoepfer, J. (2000) *Structure-based design of compounds inhibiting Grb2-SH2 mediated protein-protein interactions in signal transduction pathways*. Current Pharmaceutical Design, 6(18), 1777-1796.

Froyen, P. (1997) Tetrahedron Lett. 38(30), 5359.

Fry, D. W., Kraker, A. J., McMichael, A., Ambroso, L. A., Nelson, J. M. Leopold, W. R., Connors, R. W. & Bridges, A. J. (1994) *A Specific Inhibitor of the Epidermal Growth Factor Receptor Tyrosine Kinase*. Science, 265, 1093-1095.

Garcia-Echeverria, C.; Traxler, P.; Evans, D. B. (2000) *ATP Site-directed competitive and irreversible inhibitors of protein kinases*. Med. Res. Rev. 20(1), 28-57.

Garcia-Echeverria, C. (2001) *Antagonists of the SRC homology 2 (SH2) domains of Grb2, Src, Lck, and ZAP-70*. Current Medicinal Chemistry, 8(13), 1589-1604.

Hanks, S. K. & Hunter, T. (1995) *Protein kinases. 6. The eukaryotic protein kinase superfamily: Kinase (catalytic) domain structure and classification*. FASEB J., 9, 576-596.

Hanke, J. H., Gardner, J. P., Dow, R. L., Changelian, P. S., Brissette, W. H., Weringer, E. J., Pollok, B. A. & Connelly, P. A. (1996) *Discovery of a novel, potent, and Src family-selective tyrosine kinase inhibitor*. J. Biol. Chem., 271, 695-701.

Haskell, M. D.; Slack, J. K.; Parsons, J. Thomas; Parsons, S. J. (2001) *c-Src tyrosine phosphorylation of epidermal growth factor receptor, p-190 RhoGAP, and focal adhesion kinase regulates diverse cellular processes*. Chemical Reviews 101(8), 2425-2440.

Hisano, C., Nakano, S., Fujishima, H., Masumoto, N., Tatsumoto, T., & Niho. Y. (1997) *Src oncogene inhibits detachment-induced apoptosis through constitutive activation of p125FAK in HAG-1 human epithelial cells*. Proc. Annu. Meet. Am. Assoc. Cancer Res. 38:A1925.

Hsu, C-Y., J., Jacoski, M. V., Maguire, M. P., Spada, A. P. & Zilberstein, A. (1992) *Inhibition Kinetics and Selectivity of the Tyrosine Kinase Inhibitor Erbstatin and a Pyridone-based Analog*. Biochemical Pharmacology, 43, 241-2477.

Huang, C-K., Wu, F-Y., Ai, Y-X. (1995) *Polyhydroxylated 3-(N-phenyl)carbamoyl-2-iminochromene derivatives as potent inhibitors of tyrosine kinase p60c-src*. Bioorg. & Med. Chem. Lett., 5, 2423-2428.

Hubbard, S. R., Wei, L, Ellis, L, & Hendrickson, W. A. (1994) *Crystal structure of the tyrosine kinase domain of the human insulin receptor*, Nature, 372, 746-754.

Hubbard, S. R., Till, J. H. (2000) *Protein tyrosine kinase structure and function*, Ann. Rev. Biochem., 69, 373-398.

Hunter, T. (1987) *A thousand and one protein kinases*. Cell, 50, 823-829.

Hunter, T. (1994) *1001 protein kinases redux-towards 2000*. Seminars in Cell Biol., 5, 367-376.

Irby, R. B.; Yeatman, T. J. (2000) *Role of Src expression and activation in human cancer*. Oncogene 19, 5536-5642.

Karni, R., Jove R., & Levitzki A. (1999) *Inhibition of pp60c-src reduces Bcl-X expression and reverses the transformed phenotype of cells overexpressing EGF and HER-2 receptors*. Oncogene 18(33): 4654-4662.

Kelloff, G. J., Fay, J. R., Steele, V. E., Lubet, R. A., Boone, C. W., Crowell, J. A. (1996) *Epidermal growth factor receptor tyrosine kinase inhibitors as potential cancer chemopreventatives*. Cancer Epidemiology, Biomarkers & Prevention, 5, 657-666.

Knighton, D. R., Cadena, D. L., Zheng, J., Ten Eyck, L. F., Taylor, S. S. & Sowadski, J. M. (1993) *Structural features that specify tyrosine activity deduced from homology modeling of the epidermal growth factor receptor*. Proc. Natl. Acad. Sci. U.S.A., 90(11), 5001-5.

Kolibaba, K. S. & Druker, B. J. (1997) *Protein tyrosine kinases and cancer*. Biochimica et Biophysica Acta, 1333: F217-F248.

Lai, J. H., Marsilje, T. M., Choi, S., Nair, S. A., Hangauer, D. G. (1998) *The design, synthesis and activity of pentapeptide pp60c-src inhibitors containing L-phosphotyrosine mimics*. J. Peptide Res., 51, 271-281.

Lawrence, D. S. & Niu, J. (1998) *Protein Kinase Inhibitors: The Tyrosine-Specific Protein Kinases*. Pharmacol. Ther., 77(2), 81-114.

Levitzki, A. (1996a) *Targeting signal transduction for disease therapy*. Current Opinion in Cell Biology, 8, 239-244.

Levitzki, A. (1996b) *SRC as a target for anti-cancer drugs*. Anti-Cancer Drug Design, 11, 175-182.

Levitzki, A.; Gazit, A. (1995) *Tyrosine Kinase Inhibition: An Approach to Drug Development*. Science, 267, 1782-1788.

Luttrell, D. K.; Lee, A.; Lansing, T. J.; Crosby, R. M.; Jung, K. D.; Willard, D.; Luther, M.; Rodriguez, M.; Berman, J.; Gilmer, T. M. (1994) *Involvement of pp60$^{c\text{-}src}$ with two major signaling pathways in human breast cancer*. Proc. Natl. Acad. Sci. USA, 91, 83-87.

Lynch, S. A.; Brugge, J. S.; Fromowitz, F.; Glantz, L.; Wang, P.; Caruso, R.; Viola, M. V. (1993) *Increased expression of the src proto-oncogene in hairy cell leukemia and a subgroup of B-cell lymphomas*. Leukemia, 7, 1416-1422.

Madhusudan, Trafny, E. A., Xuong, N-H, Adams, J. A., Ten Eyck, L. F., Taylor, S. S. & Sowadski, J. M. (1994) *cAMP-dependent protein kinase: Crystallographic insights into substrate recognition and phosphotransfer*. Protein Science, 3, 176-187.

Mao, W. G., Irby, R., Coppola, D., Fu, L., Turner, J. (1997) *Activation of c-src by receptor tyrosine kinases in human colon cancer cells with high metastatic potential*. Oncogene, 15, 3083-3090.

Marsilje, T. H., Milkiewicz, K. L., & Hangauer, D. L. (2000) *The design, synthesis and activity of non-ATP competitive inhibitors of pp60c-src tyrosine kinase 1. Hydroxynaphthalene Derivatives*. Bioorganic and Medicinal Chemistry Letters, in press.

Martin, G. S. (2001) *TIMELINE: The hunting of the Src*. Nat. Rev. Mol. Cell Biol., 2, 467-475.

Mazurenko, N. N.; Kogen, E. A.; Zborovskaya, I. B.; Kisseljov, F. L. (1992) *Expression of pp60$^{c\text{-}src}$ in human small cell and non-small cell lung carcinomas*. European J. of Cancer, 28, 372-377.

Muller, G. (2001) *Peptidomimetic SH2 domain antagonists for targeting signal transduction*. Topics in Current Chemistry, 211, 17-59.

Park, B. K, Kitteringham, N. R., O'Neill, P. M. (2001) *Metabolism of Fluorine-Containing Drugs*. Ann. Rev. Pharmacol. Toxicol., 41, 443-470.

Parsons, J. T. & Parsons, S. J. (1997) *Src family protein tyrosine kinases: cooperating with growth factor and adhesion signaling pathways*. Current Opinion in Cell Biology, 9, 187-192.

Patrick, D. R. & Heimbrook, D. C. (1996) *Protein Kinase Inhibitors For The Treatment of Cancer*. Drug Discovery Today, 1, 325-330.

Posner, I., Engel, M., Gazit, A. & Levitzki, A. (1994) *Kinetics of Inhibition by Tyrphostins of the Tyrosine Kinase Activity of the Epidermal Growth Factor Receptor and Analysis by a New Computer Program*. Molecular Pharmacology, 45, 673-683.

Ramdas, L., Obeyesekere, N. U., McMurray, J. S., Gallick, G. E., Seifert, W. E. Jr. & Budde, R. J. (1995) *A tyrphostin-derived inhibitor of protein tyrosine kinases: isolation and characterization*. Archives of Biochemistry & Biophysics, 323, 237-242.

Ramdas, L., McMurray, J. S. & Budde, R. J. (1994) *The degree of inhibition of protein tyrosine kinase activity by tyrphostin 23 and 25 is related to their instability*. Cancer Research, 54, 867-869.

Rewcastle, G. W., Palmer, B. D., Thompson, A. M., Bridges, A. J., Cody, D. R., Zhou, H. Fry, D. W., McMichael, A. & Denny, W. A. (1996) *Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor*. J. Med. Chem., 39, 1823-1835.

Rudd, C. E.; Janssen, O.; Prasad, K. V. S.; Raab, M.; da Silva, A.; Telfer, J. C.; Yamamoto, M. (1993) *Src-related protein tyrosine kinases and their surface receptors*. Biochimica et Biophysica Acta, 1155, 239-266.

Saperstein, R., Vicario, P. P., Strout, H. V., Brady, E., Slater, E. E., Greenlee, W. J., Ondeyka, D. L., Patchett, A. A. & Hangauer, D. G. (1989) *Design of a selective insulin receptor tyrosine kinase inhibitor and its effect on glucose uptake and metabolism in intact cells*. Biochemistry, 28, 5694-5701.

Sawutz, D. G.; Bode, D. C.; Briggs, G. M.; Reid, J. R.; Canniff, P.; Caldwell, L.; Faltynek, C. R.; Miller, D.; Dunn, J. A.; Garavilla, L.; Guiles, J. W.; Weigelt, C.; Michne, W.; Treasurywala, A. M.; Silver, P. J. (1996) Biochem. Pharmacol. 51, 1631.

Sawyer, T.; Boyce, B.; Dalgarno, D.; Iulicci, J. (2001) *Src inhibitors: genomics to therapeutics*. Expert Opin. Investg. Drugs 10(7), 1327-1344.

Schlessinger, J. (2000) *New roles for Src kinases in control of cell survival and angiogenesis*. Cell 100, 293-296.

Schwartzberg, P. L., et al. (1997) *Rescue of osteoclast function by transgenic expression of kinase-deficient Src in Src-/- mutant mice*. Genes & Development 11: 2835-2844.

Sedlacek, H. H. (2000) *Kinase inhibitors in cancer therapy*. Drug, 59(3), 435-476.

Showalter, H. H. & Kraker, A. J. (1997) *Small molecule inhibitors of the platelet-derived growth factor receptor, the fibroblast growth factor receptor, and Src family tyrosine kinases*. Pharmacology & Therapeutics, 76, 55-71.

Sparks, A. B.; Quilliam, L. A.; Thorn, J. M.; Der, C. J.; Kay, B. K. (1994) *Identification and characterization of Src SH3 ligands from phage-displayed random peptide libraries*. Journal of Biological Chemistry, 269(30), 23853-6.

Sridhar, R.; Hanson-Painton, O.; Cooper, D. R. (2000) *Protein kinases as therapeutic targets*. Pharmaceutical Research 17(11), 1345-1353.

Stanwell, C., Burke, T. R. & Yuspa, S. H. (1995) *Erbstatin Analogue Methyl 2,5-dihydrocinnamate Cross-links Proteins and is Cytotoxic to Normal and Neoplastic Epithelial Cells by a Mechanism Independent of Tyrosine Kinase Inhibition*. Cancer Research, 55, 4950-4956.

Stanwell, C., Ye, B. & Burke, T. R. (1996) *Cell Protein Cross-linking by Erbstatin and Related Compounds*. Biochemical Pharmacology, 52, 475-480.

Stein, R. (1998). *SH2 and SH3 domains. Unraveling signaling networks with peptide antagonists*. Methods in Molecular Biology, 88, 187-195.

Susa, M., Teti, A. (2000) *Tyrosine kinase Src inhibitors: Potential Therapeutic Applications*. Drug News Perspect. 13(3), 169-175.

Susa, M., Missbach, M.; Green, J. (2000) *Src inhibitors: drugs for the treatment of osteoporosis, cancer of both?* TIPS 21, 489-495.

Takeshima, E.; Hamaguchi, M.; Watanbe, T.; Akiyama, S.; Kataoka, M.; Ohnishi, Y.; Xiao, H.; Hagai, Y., Taka, H. (1991) *Aberrant elevation of tyrosine-specific phosphorylation in human gastric cancer cells*. Japan J. Cancer Res., 82, 1428-1435.

Talamonti, M. S.; Roh, M. S.; Curley, S. A.; Gallick, G. E. (1993) *Increase in activity and level of $pp60^{c-src}$ in progressive stages of human colorectal cancer*. J. of Clinical Investigation, 91, 53-60.

Taylor, S. J., Shalloway, D. (1996) *Src and the control of cell division*. Bioessays, 18, 9-11.

Taylor, S. S., Knighton, D. R., Zheng, J., Sowadski, J. M., Gibbs, C. S. & Zoller, M. J. (1993) *A template for the protein kinase family*. Trends in Biochemical Sciences, 18(3), 84-9.

Tremblay, L.; Hauck, W.; Aprikian, A. G.; Begin, L. R.; Chapdelaine, A.; Chevalier, S. (1996) *Focal adhesion kinase (pp125FAK) expression, activation and association with paxillin and p50csk in human metastatic prostate carcinoma*. Int. J. Cancer, 68, 164-171.

Vu, C. B., (2000) *Recent advances in the design and synthesis of SH2 inhibitors of Src, Grb2 and ZAP-70*. Current Medicinal Chemistry, 7(10), 1081-1100.

Yamamoto, T. (1993) *Molecular Basis of Cancer: Oncogenes and Tumor Suppresor Genes*. Microbiol. Immunol. 37, 11-22.

What is claimed:

1. A method for protecting against or treating hearing loss in a subject comprising administering an effective amount of a protein tyrosine kinase inhibitor having the formula:

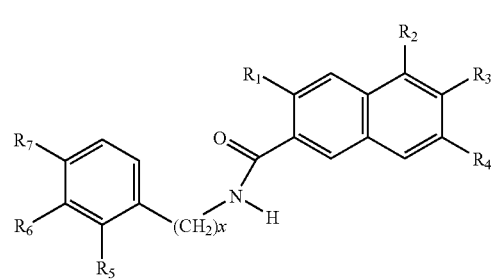

wherein $R_1$ through $R_7$ are each the same or different and are selected from the group consisting of H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and branched, cyclic, or unbranched alkyl;

wherein $R_a$, $R_b$, and $R_c$ can be the same or different and are selected from the group consisting of H, aryl, heteroaryl, biaryl, heterobiaryl, and branched, cyclic, or unbranched alkyl; and x is 0 or 1.

2. The method according to claim 1, wherein at least one of $R_1$ through $R_7$ is OH.

3. The method according to claim 1, wherein at least two of $R_1$ through $R_7$ are OH.

4. The method according to claim 1, wherein at least three of $R_1$ through $R_7$ are OH.

5. The method according to claim 1, wherein at least four of $R_1$ through $R_7$ are OH.

6. The method according to claim 1, wherein at least one of $R_1$ through $R_7$ is $OR_a$.

7. The method according to claim 6, wherein $R_a$ is branched, unbranched, or cyclic alkyl.

8. The method according to claim 7, wherein $R_a$ is methyl.

9. The method according to claim 1, wherein at least one of $R_1$, $R_2$, or $R_3$ is OH.

10. The method according to claim 1, wherein x is 1.

11. The method according to claim 1, wherein x is 0.

12. The method according to claim 1, wherein the protein tyrosine kinase inhibitor inhibits protein tyrosine kinase activity but does not inhibit ATP binding to the protein tyrosine kinase.

13. The method according to claim 12, wherein the protein tyrosine kinase inhibitor is a peptide substrate directed inhibitor.

14. The method according to claim 1, wherein the protein tyrosine kinase inhibitor is a SH2 inhibitor.

15. The method according to claim 1, wherein the protein tyrosine kinase inhibitor is a SH3 inhibitor.

16. The method according to claim 1, wherein the protein tyrosine kinase inhibitor is an allosteric inhibitor.

17. The method according to claim 1, wherein the protein tyrosine kinase inhibitor inhibits ATP binding to the protein tyrosine kinase.

18. The method according to claim 1, wherein the protein tyrosine kinase is a Src family protein tyrosine kinase.

19. The method according to claim 18, wherein the Src family protein tyrosine kinase is pp60[c-src] tyrosine kinase.

20. The method according to claim 1, wherein the protein tyrosine kinase is focal adhesion kinase.

21. The method according to claim 1, wherein the administering is carried out orally, parenterally, subcutaneously, intravenously, intramuscularly, intraperitoneally, by intranasal instillation, by intracavitary or intravesical instillation, intraauditorily, intraarterially, intralesionally, by metering pump, or by application to mucous membranes.

22. The method according to claim 1, wherein protein tyrosine kinase inhibitor is administered with a pharmaceutically acceptable carrier.

23. The method according to claim 1, wherein the protein tyrosine kinase inhibitor is administered before initiation of hearing loss.

24. The method according to claim 1, wherein the protein tyrosine kinase inhibitor is administered after initiation of hearing loss.

25. The method according to claim 1, wherein the protein tyrosine kinase inhibitor is selected from:

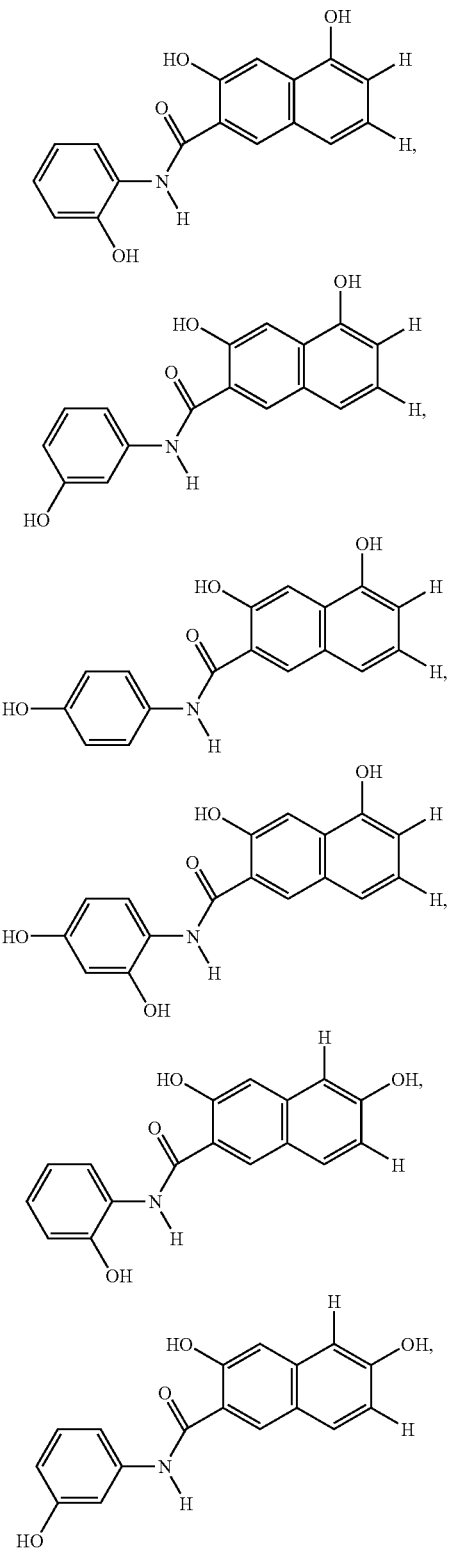

-continued
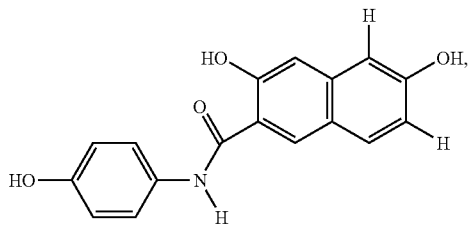
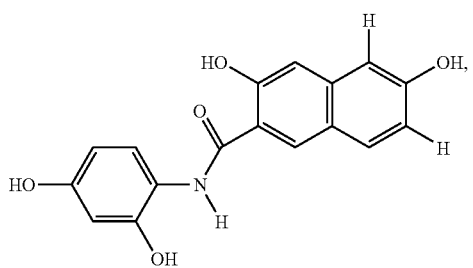
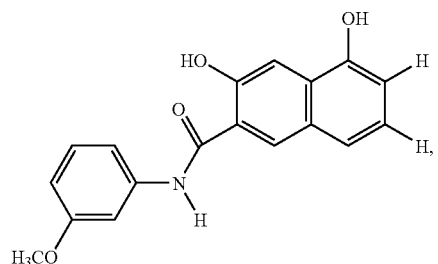
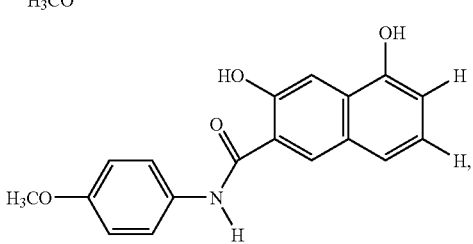
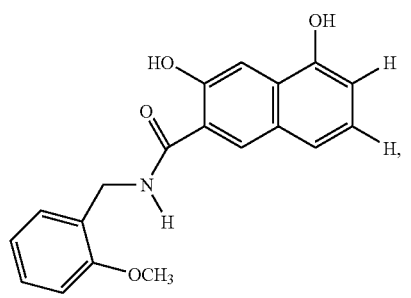
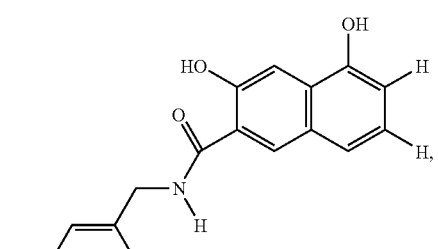
-continued
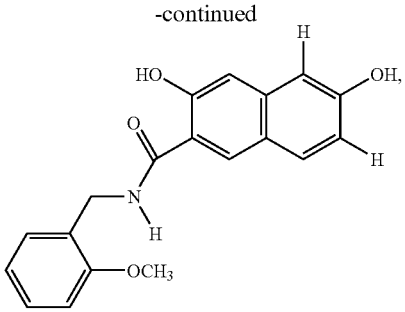
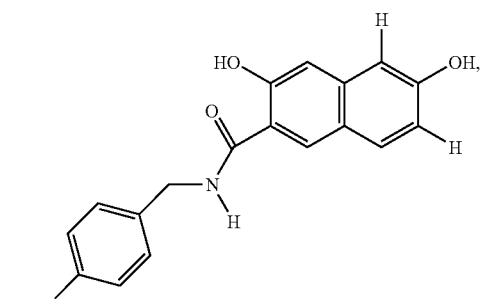
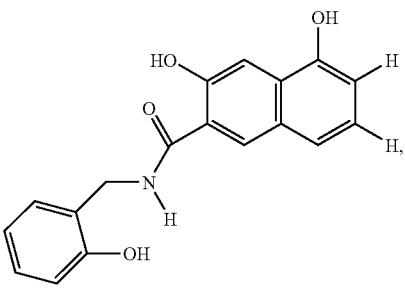
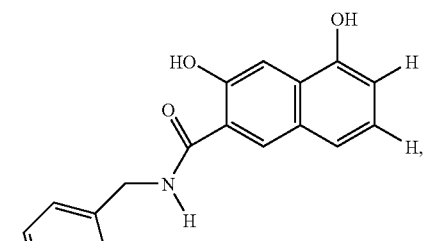
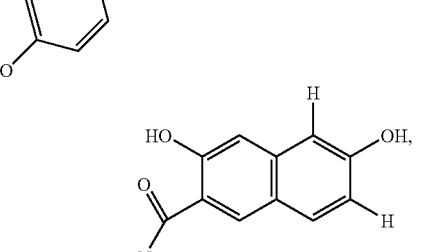

-continued
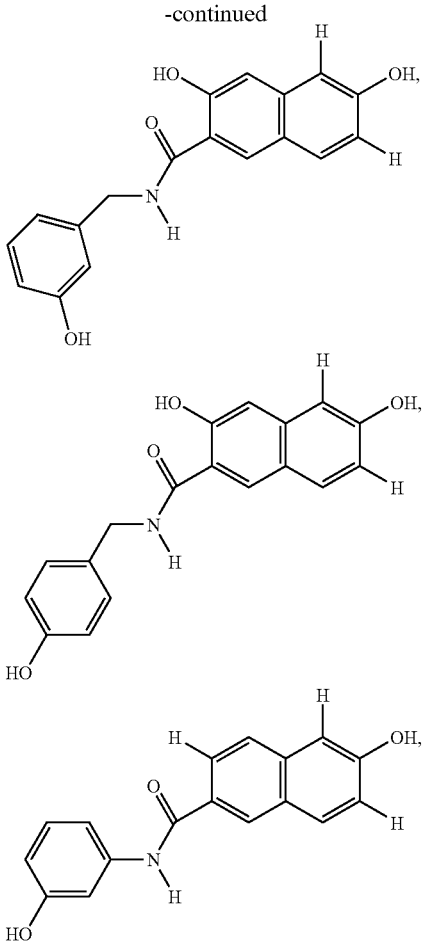
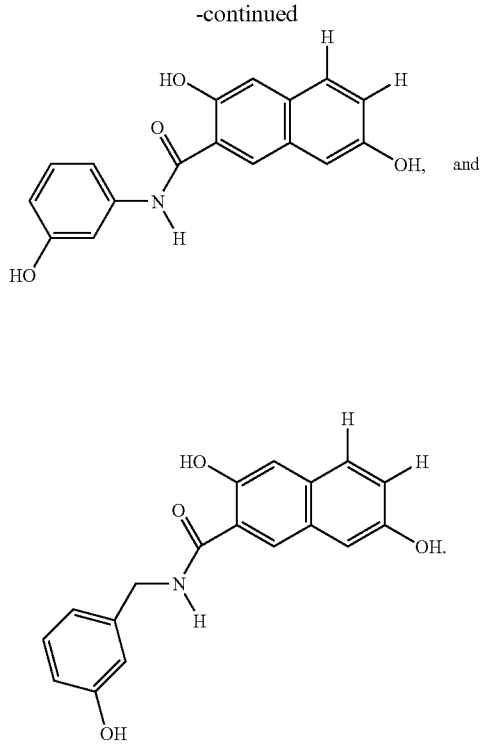
* * * * *